United States Patent
Machhammer et al.

(10) Patent No.: US 7,388,109 B2
(45) Date of Patent: Jun. 17, 2008

(54) PREPARATION OF ACROLEIN OR ACRYLIC ACID OR A MIXTURE THEREOF FROM PROPANE

(75) Inventors: Otto Machhammer, Mannheim (DE); Goetz-Peter Schindler, Mannheim (DE); Christoph Adami, Weinheim (DE); Claus Hechler, Ludwigshafen (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 437 days.

(21) Appl. No.: 11/131,248

(22) Filed: May 18, 2005

(65) Prior Publication Data

US 2006/0004226 A1    Jan. 5, 2006

Related U.S. Application Data

(60) Provisional application No. 60/662,804, filed on Mar. 18, 2005, provisional application No. 60/584,469, filed on Jul. 1, 2004.

(30) Foreign Application Priority Data

Jul. 1, 2004 (DE) .................. 10 2004 032 129
Mar. 18, 2005 (DE) .................. 10 2005 013 039

(51) Int. Cl.
    *C07C 51/16* (2006.01)
(52) U.S. Cl. ...................... 562/549; 562/545
(58) Field of Classification Search ...................... None
    See application file for complete search history.

(56) References Cited

U.S. PATENT DOCUMENTS

| | | | | |
|---|---|---|---|---|
| 5,705,684 | A | * | 1/1998 | Hefner et al. ............... 562/545 |
| 6,781,017 | B2 | * | 8/2004 | Machhammer et al. ..... 568/470 |
| 2003/0187299 | A1 | | 10/2003 | Machhammer et al. |
| 2004/0063988 | A1 | | 4/2004 | Hechler et al. |
| 2004/0063989 | A1 | | 4/2004 | Hechler et al. |
| 2005/0119515 | A1 | | 6/2005 | Machhammer et al. |

FOREIGN PATENT DOCUMENTS

| | | |
|---|---|---|
| DE | 102 11 275 A1 | 9/2003 |
| DE | 102 45 585 A1 | 4/2004 |
| DE | 102 46 119 A1 | 4/2004 |
| WO | WO 01/96270 A2 | 12/2001 |

* cited by examiner

*Primary Examiner*—Paul A Zucker
(74) *Attorney, Agent, or Firm*—Oblon, Spivak, McClelland, Maier & Neustadt, P.C.

(57) ABSTRACT

A process for preparing acrolein or acrylic acid or a mixture thereof from propane, in which the propane is initially dehydrogenated under heterogeneous catalysis to give propene, secondary components are removed and the remaining gas mixture, comprising propane and propene, is subjected to the heterogeneously catalyzed partial oxidation to acrolein or acrylic acid or a mixture thereof as the target product, target product is removed from the product gas mixture and the remaining residual gas, comprising excess oxygen and unconverted propane, is recycled into the propane dehydrogenation in such a way that the other propane fed to the dehydrogenation is at least partly converted under dehydrogenating conditions at the recycle point.

41 Claims, 1 Drawing Sheet

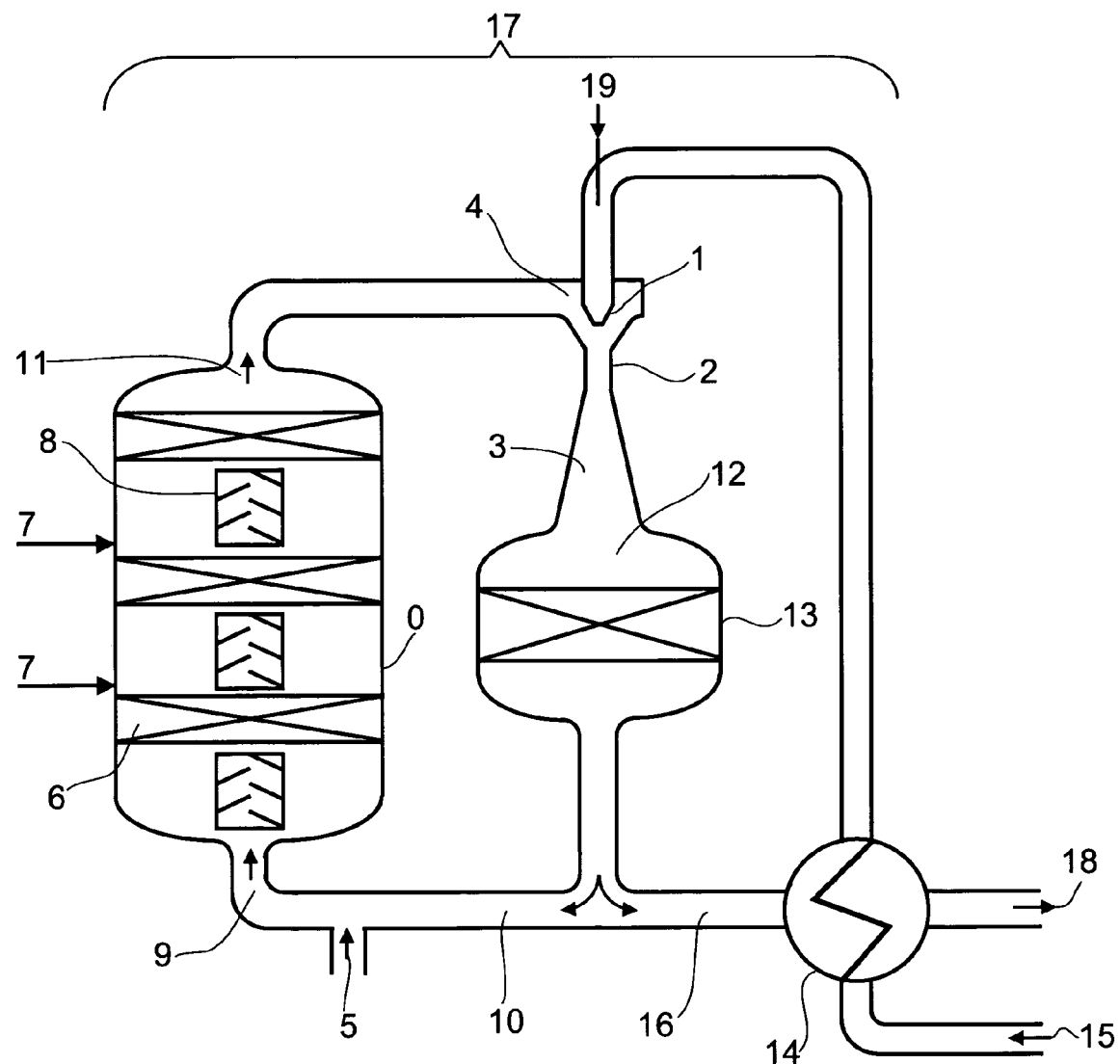

PREPARATION OF ACROLEIN OR ACRYLIC ACID OR A MIXTURE THEREOF FROM PROPANE

BACKGROUND OF THE INVENTION

1. Field of the Invention

The present invention relates to a process for preparing acrolein or acrylic acid or a mixture thereof from propane, by A) feeding to a first reaction zone A at least two gaseous, propane-containing feed streams, at least one of which comprises fresh propane, and, in reaction zone A, subjecting their propane fed in this way to a heterogeneously catalyzed dehydrogenation to obtain a product gas mixture A comprising propane and propylene, B) conducting product gas mixture A out of reaction zone A and, in a first separation zone A, removing at least a portion of the constituents, other than propane and propylene, present in product gas mixture A, and using remaining product gas mixture A' comprising propane and propylene C) in a second reaction zone B to charge at least one oxidation reactor and, in the at least one oxidation reactor, subjecting the propylene present in product gas mixture A' to a (selective) heterogeneously catalyzed gas phase partial oxidation with molecular oxygen to give a product gas mixture B comprising acrolein or acrylic acid or a mixture thereof as the target product and also excess molecular oxygen, D) conducting product gas mixture B out of reaction zone B and, in a second separation zone B, removing target product present in product gas mixture B, and, of the remaining residual gas comprising unconverted propane, molecular oxygen and any unconverted propylene, recycling at least a portion comprising unconverted propane, molecular oxygen and any unconverted propylene as one of the at least two propane-containing feed streams into reaction zone A.

2. Description of the Background

Acrylic acid is an important basic chemical whose uses include as a monomer for preparing polymers which are employed, for example, dispersed in aqueous medium, as a binder. Acrolein is an important intermediate, for example for the preparation of glutaraldehyde, methionine, folic acid and acrylic acid.

The process, described in the preamble of this document, for preparing acrolein or acrylic acid or a mixture thereof from propane is known (for example from WO 01/96270, US 2003/0187299 A1 and from the documents DE-A 10245585 and DE-A 10246119 and the prior art cited in these documents).

In the processes for removing target product present in product gas mixture B, the target product is transferred from the gaseous into the condensed phase, for example, by absorptive and/or condensative measures. Useful absorbents include, for example, water, aqueous solution and/or organic solvent. In the course of this "condensation" of the target product, a residual gas which is not transferred into the condensed phase normally remains and comprises the constituents of product gas mixture B which are comparatively difficult to condense. These are typically in particular those components whose boiling point at atmospheric pressure (1 bar) is $\leq -30°$ C. (their total content in the residual gas is generally $\geq 70\%$ by volume, frequently $\geq 80\%$ by volume and in many cases $\geq 90\%$ by volume). These include primarily unconverted propane, excess molecular oxygen remaining in reaction zone B and any unconverted propylene. In addition, the residual gas will generally contain inert diluent gases, e.g. $N_2$, $CO_2$, noble gases (He, Ne, Ar etc.), CO and also, to a small extent, acrylic acid, acrolein and/or $H_2O$ (the steam content in the residual gas may be up to 25% by volume, frequently up to 20% by volume or up to 10% by volume, but in many cases also below 10% by volume or below 5% by volume). This aforementioned residual gas forms (based on the amount of propane contained therein) the majority (normally at least 80%, or at least 90%, or at least 95%, or more) of the residual gas formed in separation zone B and is therefore also referred to in this document, inter alia, as main residual gas.

Especially when the condensation of the target product is effected by absorption by means of an organic solvent, at least one second residual gas comprising unconverted propane and any unconverted propylene is generally obtained in separation zone B (based on propane contained therein, its amount in comparison to the amount of main residual gas is normally substantially smaller). This can be attributed to the fact that, as the condensed phase forms, it also absorbs to a certain extent unconverted propane and any unconverted propylene. In the further course of the extractive, distillative, crystallizative and/or desorptive removal of the target product from the condensed phase, this unconverted propane and any propylene is normally recovered as a constituent of at least one further gas phase and preferably recycled into reaction zone A. This may be effected, for example, in a mixture with the main residual gas (in that case, referred to in this document as overall residual gas). However, it may also be effected in the form of independent gas streams to be recycled into reaction zone A. The latter may be oxygen-free or else oxygen-containing (secondary residual gas) (for example, when it is obtained by stripping by means of air or at the top of a rectification column flushed by means of air as a polymerization inhibitor).

In the context of this invention, main residual gas, overall residual gas and secondary residual gas are all residual gas comprising unconverted propane, molecular oxygen and any unconverted propylene which can be recycled into reaction zone A. According to the invention, molecular oxygen-free residual gas which is obtained in separation zone B and comprises unconverted propane and any unconverted propylene may be recycled into reaction zone A in a mixture with main residual gas and/or secondary residual gas (i.e., for example, as a constituent of overall residual gas) and/or else independently (in this case, it is residual gas which is not recycled into reaction zone A in the context of the invention). In the latter case, this recycling may be effected without any restriction, i.e., for example, even as a constituent of the starting reaction gas mixture of reaction zone A. Preference is given in the process according to the invention to recycling the entire amount of the gas streams comprising the unconverted propane and any unconverted propylene obtained in separation zone B into reaction zone A. Portions may (as will be explained in detail in the further course of the application), if appropriate, also be used for other purposes, for example for energy generation and/or synthesis gas production and/or as a diluent gas in reaction zone B.

In the aforementioned prior art documents, the recycling of residual gas comprising unconverted propane, molecular oxygen and any unconverted propylene into reaction zone A should be at the same point as the feed of the remaining propane-containing feed streams into reaction zone A (i.e. as the constituent of the starting reaction gas mixture; cf., for example, FIG. 6 in US-2003/0187299 A1). A disadvantage of this procedure is that the molecular oxygen present in the residual gas reduces the selectivity of propene formation in reaction zone A and increases the selectivity of by-product formation of the carbon oxides CO and $CO_2$ as a consequence of partial full combustion of propane and/or propylene. This is especially true when the residual gas to be recycled is main residual gas.

DE-A 10211275 attempts to remedy the aforementioned problem by proceeding as described above but simultaneously dividing the product gas mixture A formed in reaction zone A into two portions of identical composition and recycling one of the two portions into reaction zone A as the hydrogen source. However, a disadvantage is that the deactivation rate of the dehydrogenation catalysts in this procedure is not fully satisfactory.

SUMMARY OF THE INVENTION

It is therefore an object of the present invention to provide a process, improved over the aforementioned processes, for preparing acrolein or a acrylic acid or a mixture thereof from propane.

Accordingly, a process has been found for preparing acrolein or acrylic acid or a mixture thereof from propane, by
A) feeding to a first reaction zone A at least two gaseous, propane-containing feed streams, at least one of which comprises fresh propane, and, in reaction zone A, subjecting their propane fed in this way to a heterogeneously catalyzed dehydrogenation to obtain a product gas mixture A comprising propane and propylene (product gas mixture A will generally also comprise molecular hydrogen),
B) conducting product gas mixture A out of reaction zone A and, in a first separation zone A, removing at least a portion of the constituents, other than propane and propylene, present in product gas mixture A, and using remaining product gas mixture A' comprising propane and propylene
C) in a second reaction zone B to charge at least one oxidation reactor and, in the at least one oxidation reactor, subjecting the propylene present in product gas mixture A' to a (selective) heterogeneously catalyzed gas phase partial oxidation with molecular oxygen to give a product gas mixture B comprising acrolein or acrylic acid or a mixture thereof as the target product and also excess molecular oxygen,
D) conducting product gas mixture B out of reaction zone B and, in a second separation zone B, removing target product present in product gas mixture B, and, of the remaining (main and/or secondary or overall) residual gas comprising unconverted propane, molecular oxygen and any unconverted propylene, recycling at least a portion (preferably at least 50% by volume, or at least 75% by volume and most preferably the entirety (based in each case individually on the overall residual gas, the main residual gas and/or the secondary residual gas)) comprising unconverted propane, molecular oxygen and any unconverted propylene as one of the at least two propane-containing feed streams into reaction zone A, wherein this recycling into reaction zone A along the reaction path of the heterogeneously catalyzed dehydrogenation of propane in reaction zone A is effected such that, at the feed point, at least 5 mol % of the (total amount of) propane fed (beforehand) to reaction zone A via the other feed streams has already been converted under dehydrogenating conditions in reaction zone A (based on single pass through reaction zone A).

BRIEF DESCRIPTION OF THE DRAWING

FIG. 1 details a preferred embodiment of reaction zone A of the process according to the invention.

DETAILED DESCRIPTION OF THE INVENTION

When the entire amount of the (main and/or secondary or overall) residual gas obtained (overall) in separation zone B is not recycled into reaction zone A in the process according to the invention, this other portion, as already mentioned, may be used further, for example, for the purpose of energy or synthesis gas generation or as a diluent gas in reaction zone B. However, generally at least half or two thirds (i.e. 50% by volume or 66.6% by volume), preferably at least three quarters and most preferably the entire amount of the aforementioned (each individually with regard to the main and/or secondary or overall) residual gas obtained in separation zone B will be recycled into reaction zone A in accordance with the invention. If only one residual gas stream comprising unconverted propane, molecular oxygen and unconverted propylene is obtained in separation zone B (this is frequently the case), this is preferably, in accordance with the invention, recycled fully (if appropriate minus a portion of identical composition conducted as diluent gas into reaction zone B) into reaction zone A. However, it may also be divided into two portions of identical composition, and, as described above, only one portion may be recycled into reaction zone A and the other portion used further in another way. If more than one such residual gas stream is obtained in separation zone B, these residual gas streams (as already mentioned), in accordance with the invention, may be recycled together (for example combined together), or else only separately or individually into reaction zone A. The percentage recycling data relate in the case of residual gas in this document in particular to its total amount (i.e. to the sum of all residual gas streams). Normally, (especially main) residual gas consists (as already mentioned) to an extent of $\geq 70\%$ by volume, frequently to an extent of $\geq 80\%$ by volume and in many cases to an extent of $\geq 90$ mol %, usually to an extent of $\geq 95$ mol % or to an extent of $\geq 98$ mol %, of constituents whose boiling point at atmospheric pressure (1 bar) is $\leq -30°$ C. According to the invention, the recycling of (main and/or secondary or overall) residual gas obtained in separation zone B and comprising molecular oxygen into reaction zone A, along the reaction path of the catalytic dehydrogenation, may obviously be not only at one feed point, but also distributed over a plurality of feed points arranged in series.

In this document, fresh propane refers to propane which has not yet passed through reaction zone A. In general, it will be crude propane (which preferably fulfills the specifications of DE-A 10246119 and DE-A 10245585) which also contains small amounts of components other than propane.

The reaction path in reaction zone A refers in this document to the flow path of the propane fed to reaction zone A via the (other) feed streams other than the residual gas from separation zone B through reaction zone A as a function of the dehydrogenating conversion (the conversion in the heterogeneously catalyzed dehydrogenation) of this propane.

In this document, the starting reaction gas mixture or else charge gas mixture fed to reaction zone A will refer to the sum of all gases fed with the fresh propane at the same level on the reaction path in reaction zone A.

According to the invention, the (main and/or secondary or overall) residual gas along the reaction path in reaction zone A is recycled into reaction zone A such that, at the feed point, at least 10 mol % or at least 15 mol %, preferably at least 20 mol % or at least 25 mol % and even more preferably at least 30 mol % or at least 35 mol % and at best at least 35 mol % or at least 40 mol %, of the (total amount of) propane fed (beforehand) to reaction zone A via the other feed streams has already been converted (under dehydrogenating conditions) (conversion $Z_u$) in reaction zone A. In general, at the feed point of the recycling of the (main and/or secondary or overall) residual gas into reaction zone A in the process according to the invention, less than 70 mol %, frequently less than 60 mol % and in many cases $\leq 50$ mol %, of the propane fed to reaction zone A via the other feed streams has already been converted under dehydrogenating conditions in reaction zone A (conversion $Z_U$).

When, as recommended in DE-A 10211275, the product gas mixture A formed in reaction zone A is divided in the process according to the invention into two portions of identical composition and one of the two portions is recycled into reaction zone A (especially when this recycling is effected as a constituent of the starting reaction gas mixture fed to reaction zone A), the conversion numbers $Z_U^{Kr}$ defined hereinbelow preferably apply instead of all of the aforementioned conversion numbers $Z_U$:

$$Z_u^{Kr} = \frac{Z_U}{1 + KGV}.$$

KGV is the ratio of portion of the product gas mixture A recycled into reaction zone A to total amount of product gas mixture A formed in reaction zone A.

The molecular oxygen content of the (main and/or secondary or overall) residual gas which is obtained in separation zone B and recycled into reaction zone A in the process according to the invention will normally be from 0.5% by volume to 10% by volume, frequently from 1 to 8% by volume and in many cases from 2 to 5% by volume. It arises typically especially from the fact that an excess of molecular oxygen (based on the stoichiometry of the desired target reaction) in reaction zone B generally has an advantageous effect on the lifetime of the oxidation catalysts and on the kinetics of the selective heterogeneously catalyzed gas phase partial oxidation of propylene to acrolein or to acrylic acid or to a mixture thereof proceeding therein. In contrast to the conditions in the inventive reaction zone A, the thermodynamic conditions in reaction zone B are substantially not influenced by the molar reactant ratio, since the selective heterogeneously catalyzed gas phase partial oxidation of propylene to acrolein or to acrylic acid or to a mixture thereof is under kinetic control.

The ratio of the amount of propane which is fed to reaction zone A via the recycled (main and/or secondary or overall) residual gas stemming from separation zone B to the total amount of propane which is fed to reaction zone A via other propane-containing feed streams in the process according to the invention will generally be from 0.1 to 10, or from 0.5 to 5, preferably from 0.5 to 1.5 or from 3 to 5.

In one embodiment of the process according to the invention, only one stream of fresh crude propane (also contains small amounts of impurities in addition to propane) will be fed as only the second feed stream in reaction zone A in addition to the propane present in the recycled (main and/or secondary or overall) residual gas stemming from separation zone B. It is preferred in accordance with the invention that this crude propane (as is generally the case in this document) will have the specifications recommended in the documents DE-A 10245585 and DE-A 10246119. The same applies to the specification of the charge gas mixture of reaction zone B in the process according to the invention. However, it will be appreciated that it is also possible in the process according to the invention to use offgas streams comprising propane (and also, if appropriate, propylene) from processes other than the process according to the invention as feed streams into reaction zone A (cf. WO 02/00587; however, the gas stream from section c) of this WO cannot be fed until reaction zone B).

It is essential to the invention merely that, at the point (at the level) of reaction zone A at which the (main and/or secondary or overall) residual gas from separation zone B is fed into reaction zone A, at least 5 mol % of the propane fed to reaction zone A via all other feed streams has already been converted within the catalytic dehydrogenation which is to be implemented in reaction zone A. When the aforementioned condition is not fulfilled, the molar ratio of molecular hydrogen to molecular oxygen at the feed point is reduced, which either promotes the full combustion of the involved $C_3$ hydrocarbons and/or reduces the lifetime of the dehydrogenation catalyst used and/or inevitably makes it necessary to feed molecular hydrogen into reaction zone A from an external source. This can presumably be attributed to the fact that both the involved $C_3$ hydrocarbons and the dehydrogenation catalyst itself are better protected from full combustion and thermal (deactivating) decomposition on the dehydrogenation catalyst in an atmosphere having an elevated molar ratio of molecular hydrogen to molecular oxygen.

In contrast to the exothermic heterogeneously catalyzed oxydehydrogenation which is forced by oxygen present and in which free hydrogen is neither formed as an intermediate (the hydrogen pulled from the hydrocarbon to be dehydrogenated is pulled out directly as water ($H_2O$)) nor is detectable, the inventive heterogeneously catalyzed dehydrogenation refers to a ("conventional") dehydrogenation whose thermal character, in contrast to the oxydehydrogenation, is endothermic (an exothermic hydrogen combustion may be included in the process according to the invention as a subsequent step) and in which free molecular hydrogen is formed at least as an intermediate. This generally requires different reaction conditions and different catalysts to the oxydehydrogenation.

In other words, the process according to the invention proceeds normally under $H_2$ evolution and especially up to the recycling of the residual gas from separation zone B into reaction zone A, which is why the reaction gas mixture, at the corresponding feed point, based on the molar amount of propane contained therein, normally has a higher molar hydrogen content than the starting reaction gas mixture fed to reaction zone A.

In the process according to the invention, the latter preferably also applies to the reaction gas mixture which is formed at the feed point by combination of residual gas recycled into it and the reaction gas mixture present before this recycling at the feed point.

Apart from this, it has been found to be favorable for the process according to the invention when the molar ratio of propylene present in the reaction gas mixture within reaction zone A to molecular hydrogen present in the reaction gas mixture does not exceed the value of 10, preferably the value of 5, better the value of 3 and even better the value of 2. More preferably, the aforementioned ratio varies at values of from 0.5 or 1 to 2.

Otherwise, the principle of the heterogeneously catalyzed dehydrogenation in reaction zone A (and thus reaction zone A itself) in the process according to the invention may be as described in the documents WO 01/96270, DE-A 3313573, DE-A 10131297, DE-A 10245585, DE-A 10246119 and DE-A 10211275. In other words, based on single pass of the charge gas mixture fed to reaction zone A through reaction zone A, reaction zone A may be configured isothermally by controlled heat exchange with (fluid, i.e. liquid or gaseous) heat carriers conducted outside reaction zone A. However, it may also be performed adiabatically with the same reference basis, i.e. substantially without such controlled heat exchange with heat carriers conducted outside reaction zone A. In the latter case, the gross thermal character, based on single pass of the starting reaction gas mixture fed to reaction zone A through reaction zone A, may, by taking the measures recommended in the abovementioned documents and yet to be described hereinbelow, be made endothermic (negative) or autothermic (substantially zero) or exothermic (positive). In the inventive manner, it is additionally necessary merely that the recycling of residual gas stemming from separation zone B into reaction zone A is effected as required in accordance with the invention. Equally, the catalysts recommended in the aforementioned documents may be employed in the process according to the invention.

Typically, the heterogeneously catalyzed partial dehydrogenation of propane to propylene requires comparatively high reaction temperatures. The achievable conversion is normally restricted by the thermodynamic equilibrium. Typical reaction temperatures are from 300 to 800° C. or from 400 to 700° C. One molecule of hydrogen is generated per molecule of propane to be dehydrogenated to propylene.

High temperatures and removal of the $H_2$ reaction product shift the equilibrium position in the direction of the target product.

Since the heterogeneously catalyzed dehydrogenation reaction proceeds with increasing volume, the conversion may be increased by lowering the partial pressure of the products. This can be achieved in a simple manner, for example by dehydrogenating under reduced pressure and/or by adding substantially inert diluent gases, for example steam which normally constitutes an inert gas for the dehydrogenation reaction. As a further advantage, dilution with steam generally causes reduced carbonization of the catalyst used, since the steam reacts with carbon formed by the principle of coal gasification. Steam may also be used as a diluent gas in the downstream reaction zone B. However, steam can also be removed in a simple manner partly or fully from the product gas mixture of the dehydrogenation (product gas mixture A) (for example by condensing), which opens up the possibility of increasing the proportion of the $N_2$ diluent gas when the thus obtainable modified product gas mixture (product gas mixture A') is further used in reaction zone B. Further diluents suitable for the heterogeneously catalyzed propane dehydrogenation are, for example, CO, methane, ethane, $CO_2$, nitrogen and noble gases such as He, Ne and Ar. All diluents mentioned may be used alone or in the form of widely varying mixtures. It is advantageous that the diluents mentioned are generally also suitable diluents in reaction zone B. Generally, preference is given in the process according to the invention to diluents which behave inertly in the particular reaction zone (i.e. are chemically altered to an extent of less than 5 mol %, preferably to an extent of less than 3 mol % and even better to an extent of less than 1 mol %).

In principle, useful dehydrogenation catalysts for the heterogeneously catalyzed propane dehydrogenation are all dehydrogenation catalysts disclosed in the prior art. They can be divided roughly into two groups: into those which are of oxidic nature (for example chromium oxide and/or aluminum oxide) and into those which consist of at least one, generally comparatively noble, metal (for example platinum) deposited on a generally oxidic support. Among others, it is thus possible to use all dehydrogenation catalysts which are recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. Nos. 4,220,091, 5,430,220, 5,877,369, EP-A-0 117 146, DE-A 199 37 196, DE-A 199 37 105 and DE-A 199 37 107. In particular, it is possible to use the catalyst of Example 1, Example 2, Example 3 and Example 4 of DE-A 199 37 107.

These are dehydrogenation catalysts which contain from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group, of the Periodic Table of the Elements, lanthanum and/or tin, with the proviso that the sum of the percentages by weight is 100% by weight.

Also particularly suitable is the dehydrogenation catalyst used in the examples and comparative examples of this document.

Generally, the dehydrogenation catalysts may be catalyst extrudates (they are typically from 1 to 10 mm, preferably from 1.5 to 5 mm, in diameter; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm).

In general, the dehydrogenation catalysts (especially those used by way of example in this document and those recommended in DE-A 19937107 (especially the exemplary catalysts of this DE-A)) are such that they are capable of catalyzing both the dehydrogenation of propane and the combustion of molecular hydrogen. In the case of a competition situation on the catalysts, hydrogen combustion proceeds very much more rapidly in comparison to the dehydrogenation of propane.

To carry out the heterogeneously catalyzed propane dehydrogenation, useful reactor types and process variants are in principle all of those disclosed in the prior art. Descriptions of such process variants are contained, for example, in all prior art documents cited with regard to the dehydrogenation catalysts and the prior art cited at the outset of this document.

A comparatively comprehensive description of dehydrogenation processes which are suitable in accordance with the invention is also contained in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

It is characteristic of the partial heterogeneously catalyzed dehydrogenation of propane, as already stated, that it proceeds endothermically. This means that the heat (energy) required for the attainment of the required reaction temperature has to be supplied to the starting reaction gas mixture either before and/or in the course of the heterogeneously catalyzed dehydrogenation. If appropriate, the reaction gas mixture has to withdraw the heat of reaction required from itself.

In addition, it is typical of heterogeneously catalyzed dehydrogenations of propane, owing to the high reaction temperatures required, that small amounts of high molecular weight organic compounds having a high boiling point, up to and including carbon, are formed and are deposited on the catalyst surface, thus deactivating it. In order to minimize this disadvantageous accompanying phenomenon, the propane-containing reaction gas mixture which is to be passed at elevated temperature over the catalyst surface for the heterogeneously catalyzed dehydrogenation can be diluted with steam. Carbon which is deposited is partly or fully eliminated under the conditions given in this way by the principle of coal gasification.

Another means of eliminating deposited carbon compounds is to allow an oxygen-containing gas (appropriately in the absence of hydrocarbons) to flow through the dehydrogenation catalyst from time to time at elevated temperature and thus to effectively burn off the deposited carbon. However, substantial suppression of the formation of carbon deposits is also possible by adding molecular hydrogen to the propane to be dehydrogenated under heterogeneous catalysis before it is conducted over the dehydrogenation catalyst at elevated temperature.

It will be appreciated that the possibility also exists of adding a mixture of steam and molecular hydrogen to the propane to be dehydrogenated under heterogeneous catalysis. Addition of molecular hydrogen to the heterogeneously catalyzed dehydrogenation of propane also reduces the undesired formation of allene (propadiene), propyne and acetylene as by-products. Partial oxidation of hydrogen added in this way is likewise capable of supplying heat of reaction required.

A suitable reactor type for the heterogeneously catalyzed propane dehydrogenation in reaction zone A is the fixed bed tube or tube bundle reactor. This means that the dehydrogenation catalyst is disposed in one or in a bundle of reaction tubes as a fixed bed. According to the invention, a second tube may advantageously be centered within the catalyst tube and have outlet points at widely varying levels (or only at one level) (cf. WO 01/85333 and WO 01/85330), through which the residual gas from separation zone B can be supplied. Alternatively, the catalyst tubes integrated into catalyst tube plates may have interruption sections (spaces), into which the residual gas from separation zone B may be metered. The reaction tubes are heated by a gas, for example a hydrocarbon such as methane, being combusted in the space surrounding the reaction tubes. It is favorable to apply this direct form of catalyst tube heating only to the first about 20 to 30% of the fixed bed and to heat the remaining bed length to the required reaction temperature by the radiative heat released in the course of the combustion. In this way, an approximately isothermal reaction is achievable. Suitable reaction tube internal diameters are from about 10 to 15 cm. A typical dehydrogenation tube bundle reactor comprises from 300 to 1000 reaction tubes. The temperature in the reaction tube interior varies within the range from 300 to 700° C., preferably within the range from 400 to 700° C. Advantageously, the starting reaction gas mixture is fed to the tubular reactor preheated to the reaction temperature. It is possible that product gas mixture A leaves the reaction tube with a temperature which is from 50 to 100° C. lower. However, this outlet temperature may also be higher or at the same level. In the context of the aforementioned procedure, it is appropriate to use oxidic dehydrogenation catalysts based on chromium oxide and/or aluminum oxide. Frequently, no diluent gas will be used, but rather the starting materials used for the starting reaction gas will essentially be solely crude propane. The dehydrogenation catalyst too is usually employed undiluted.

On the industrial scale, a plurality of (e.g. three) such tube bundle reactors can be operated in parallel in reaction zone A. In this case, one (or two) of these reactors may, in accordance with the invention, if appropriate be in dehydrogenating operation, while the catalyst charge in a second (third) reactor is regenerated without the operation in reaction zone B suffering.

Such a procedure is appropriate, for example, in the BASF-Linde propane dehydrogenation process disclosed in the literature. However, it is significant for the invention that it is sufficient to use one such tube bundle reactor.

Such a procedure can also be employed in the "steam active reforming (STAR) process" which has been developed by Phillips Petroleum Co. (see, for example, U.S. Pat. Nos. 4,902,849, 4,996,387 and 5,389,342). The dehydrogenation catalysts used in the STAR process are advantageously platinum, comprising promoters, on zinc (magnesium) spinel as the support (see, for example, U.S. Pat. No. 5,073,662). In contrast to the BASF-Linde propane dehydrogenation process, the propane to be dehydrogenated is diluted with steam in the STAR process. A typical molar ratio of steam to propane is in the range from 4 to 6. The starting reactor pressure is frequently from 3 to 8 bar and the reaction temperature is appropriately selected at from 480 to 620° C. Typical catalyst (bed) hourly space velocities with propane are from 200 to 4000 $h^{-1}$ (GHSV).

The hourly space velocity on a catalyst bed, catalyzing a reaction step, of (starting) reaction gas mixture refers to the amount of (starting) reaction gas mixture in standard liters (=l (STP); the volume in liters that the appropriate amount of (starting) reaction gas mixture would take up under standard conditions, i.e. at 0° C. and 1 atm) which is conducted per hour through one liter of catalyst bed. The hourly space velocity may also be based only on one constituent of the (starting) reaction gas mixture. In that case, it is the amount of this constituent in l (STP)/l·h which is conducted per hour through one liter of the catalyst bed. Instead of l (STP)/l·h, "$h^{-1}$" is frequently written for short.

The heterogeneously catalyzed propane dehydrogenation in the process according to the invention may also be effected in a moving bed. For example, the moving catalyst bed may be accommodated in a radial flow reactor. In the reactor, the catalyst moves slowly from top to bottom while the reaction gas mixture flows radially. This procedure is employed, for example, in the UOP-Oleflex dehydrogenation process. Since the reactors in this process are operated quasi-adiabatically, it is appropriate to operate a plurality of reactors connected in series as a battery (typically up to four). Within the battery, the residual gas may be conducted out of separation zone B. This allows excessively large differences in the temperatures of the reaction gas mixture at the reactor inlet and at the reactor outlet to be avoided (in adiabatic mode, the starting reaction gas mixture functions as a heat carrier, upon whose heat content the drop in the reaction temperature is dependent) and nevertheless allows attractive overall conversions to be achieved.

When the catalyst bed has left the moving bed reactor, it is fed to the regeneration and subsequently reused. The dehydrogenation catalyst used for this process may be, for example, a spherical dehydrogenation catalyst which consists substantially of platinum on spherical alumina support. In the UOP variant, hydrogen is added to the propane to be dehydrogenated, in order to avoid premature catalyst aging. The working pressure is typically from 2 to 5 atm. The (molar) hydrogen to propane ratio is appropriately from 0.1 to 1. The reaction temperatures are preferably from 550 to 650° C. and the residence time of the catalyst in a reactor is selected at from about 2 to 10 h.

In the fixed bed processes described, the catalyst geometry may likewise be spherical, but also cylindrical (hollow or solid) or have a different geometry.

A further possible process variant for the heterogeneously catalyzed propane dehydrogenation in the process according to the invention, described by Proceedings De Witt, Petrochem. Review, Houston, Tex., 1992 a, N1, is the possibility of a heterogeneously catalyzed propane dehydrogenation in a fluidized bed.

According to the invention, it is possible, for example, for two fluidized beds to be operated in parallel, of which one may be in the state of regeneration from time to time without negative effects on the overall process. The active composition used is chromium oxide on alumina. The working pressure is typically from 1 to 2 bar and the dehydrogenation temperature is generally from 550 to 600° C. The heat required for the dehydrogenation is introduced into the reaction system by preheating the dehydrogenation catalyst to the reaction temperature. The above dehydrogenation method is known in the literature as the Snamprogetti-Yarsintez process.

Alternatively to the above-described procedures, the heterogeneously catalyzed propane dehydrogenation in the process according to the invention may also be realized by a process developed by ABB Lummus Crest (see Proceedings De Witt, Petrochem. Review, Houston, Tex., 1992, P1).

In both aforementioned processes, the inventive addition of residual gas can be effected as a simple feed stream at the point on the reaction path according to the claims.

Common to the heterogeneously catalyzed dehydrogenation processes of propane described hitherto is that they are operated at propane conversions of $\geq 30$ mol % (generally $\leq 60$ mol %) (based on single pass through the reaction zone and total amount of propane fed). However, it is advantageous in accordance with the invention that it is sufficient to achieve a propane conversion of from $\geq 5$ mol % to $\leq 30$ mol % or $\leq 25$ mol %. This means that the inventive heterogeneously catalyzed propane dehydrogenation in reaction zone A may also be operated at propane conversions of from 10 to 20 mol % (the conversions are based on single pass through reaction zone A). Among other factors, this is based on the remaining amount of unconverted propane functioning substantially as an inert diluent gas in the downstream reaction zone B and being able to be recycled in accordance with the invention as a constituent of the residual gas obtained in separation zone B substantially without loss into reaction zone A.

However, preference is given in accordance with the invention to increased propane conversions in reaction zone A, since this reduces propionic acid by-production in reaction zone B. Such advantageous propane conversions are, for example, from 30 or 40 to 50 or 60 mol % (based on single pass through reaction zone A and the total amount of propane fed).

For the realization of the aforementioned propane conversions, it is favorable to carry out the heterogeneously catalyzed propane dehydrogenation at a working pressure of from 0.3 to 3 bar. It is also favorable to dilute the propane to be dehydrogenated under heterogeneous catalysis with steam. Thus, the heat capacity of the water firstly enables a portion of the effect of the endothermicity of the dehydrogenation to be compensated for and, secondly, the dilution with steam reduces the partial reactant and product pressure, which has a favorable effect on the equilibrium position of the dehydrogenation. The use of steam, as already mentioned, also has an advantageous effect on the lifetime of noble metal-containing dehydrogenation catalysts. If required, molecular hydrogen may also be added as a further constituent. The molar ratio of molecular hydrogen to propane is generally $\leq 5$. The molar ratio of steam to propane at a comparative low propane conversion may be, for example, from $\geq 0$ to 30, appropriately from 0.1 to 2 and favorably from 0.5 to 1. An advantage of a procedure with low propane conversion is that, on single pass of the reaction gas through reaction zone A, only a comparatively small amount of heat is consumed and comparatively low reaction temperatures are sufficient to achieve the conversion.

As already stated, the propane dehydrogenation may also be carried out in accordance with the invention (quasi) adiabatically and endothermically. The starting reaction gas mixture is generally initially heated to a temperature of from 500 to 700° C. (or from 550 to 650° C.) (for example by direct firing of the wall surrounding it). On adiabatic pass through the at least one catalyst bed, the reaction gas mixture will then cool by from about 30° C. to 200° C. depending on conversion and dilution. Downstream of the inventive injection of the residual gas from separation zone B, there will be a certain degree of heating. The presence of steam as a heat carrier is also noticeably advantageous from the point of view of an adiabatic method. Lower reaction temperatures enable longer lifetimes of the catalyst bed used. Higher reaction temperatures promote increased conversions.

In principle, the heterogeneously catalyzed propane dehydrogenation in reaction zone A, irrespectively of whether conducted adiabatically or isothermally, can be carried out either in a fixed bed reactor or else in a moving bed or fluidized bed reactor.

Remarkably, as reaction zone A in the process according to the invention, even in adiabatic operation, a single shaft furnace reactor which is flowed through by the reaction gas mixture axially and/or radially can be sufficient as a fixed bed reactor.

In the simplest case, this is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and is substantially heat-insulated in adiabatic operation is flowed through axially by the hot, propane-containing reaction gas. The catalyst geometry may be either spherical or else annular or strand-shaped. The residual gas stemming from separation zone B may be injected via feed lines introduced into the catalyst bed. Since the reaction volume can be realized in this case by a very inexpensive apparatus, preference is to be given to all catalyst geometries which have a particularly low pressure drop. These are in particular catalyst geometries which lead to a large cavity volume or are structured, for example monoliths or honeycombs. To realize a radial flow of the propane-containing reaction gas, the reactor may, for example, consist of two concentric cylindrical grids disposed in a shell and the catalyst bed may be arranged in their annular gap. In the adiabatic case, the metal shell would in turn be thermally insulated if appropriate.

Useful inventive catalyst charges for a heterogeneously catalyzed propane dehydrogenation are especially the catalysts disclosed in DE-A 199 37 107, in particular all of those disclosed by way of example.

After a prolonged operating time, the aforementioned catalysts can be regenerated in a simple manner, for example, by initially passing air (preferably) diluted with nitrogen and/or steam in first regeneration stages over the catalyst bed at an inlet temperature of from 300 to 600° C., frequently from 400 to 550° C. The catalyst (bed) hourly space velocity of regeneration gas (for example air) may be, for example, from 50 to 10 000 h$^{-1}$ and the oxygen content of the regeneration gas may be from 0.1 or 0.5 to 20% by volume.

In subsequent further regeneration stages, the regeneration gas used under otherwise identical regeneration conditions may be air. Appropriately from an application point of view, it is recommended to flush the catalyst with inert gas (for example N$_2$) before it is regenerated.

It is generally to be recommended to subsequently regenerate with pure molecular hydrogen or with molecular hydrogen diluted with inert gas (preferably steam) (the hydrogen content should be $\geq$1% by volume) under otherwise identical conditions.

The heterogeneously catalyzed propane dehydrogenation with comparatively low propane conversion ($\leq$30 mol %) may in all cases be carried out at the same catalyst (bed) hourly space velocities (with regard both to the reaction gas overall and to the propane contained therein) as the variants with high propane conversion (>30 mol %). This hourly space velocity of reaction gas may be, for example, from 100 to 40 000 or to 10 000 h$^{-1}$, frequently from 300 to 7000 h$^{-1}$, i.e. in many cases from about 500 to 4000 h$^{-1}$.

Appropriately from an application point of view, reaction zone A in the process according to the invention can be realized as a tray reactor, which enables the metering of the residual gas from separation zone B between two trays in a particularly simple manner.

This comprises more than one catalyst bed catalyzing the dehydrogenation in spatial succession. The catalyst bed number may be from 1 to 20, appropriately from 2 to 8, or else from 3 to 6. Increased propane conversions can be achieved increasingly readily with increasing number of trays. The catalyst beds are preferably arranged in radial or axial succession. From an application point of view, it is appropriate to use the fixed bed catalyst type in such a tray reactor.

In the simplest case, the fixed catalyst beds in a shaft furnace reactor are arranged axially or in the annular gaps of concentric cylindrical grids. However, it is also possible to arrange the annular gaps in segments one above the other and to conduct the gas after it has passed radially through one segment into the next segment above it or below it.

Appropriately, the reaction gas mixture is subjected to intermediate heating in the tray reactor on its path from one catalyst bed to the next catalyst bed, for example by passing it over heat exchanger surfaces (e.g. ribs) heated by hot gases or by passing it through pipes heated by hot combustion gases.

When the tray reactor is otherwise operated adiabatically, it is sufficient for propane conversions of $\leq$30 mol %, in particular when using the catalysts described in DE-A 199 37 107, especially those of the exemplary embodiments, to conduct the reaction gas mixture into the dehydrogenation reactor preheated to a temperature of from 450 to 550° C. and to keep it within this temperature range inside the tray reactor. This means that the entire propane dehydrogenation can thus be realized at very low temperatures, which is found to be particularly favorable for the lifetime of the fixed catalyst beds between two regenerations. For higher propane conversions, the reaction gas mixture is appropriately conducted into the dehydrogenation reactor preheated to higher temperatures (these may be up to 700° C.) and kept within this elevated temperature range inside the tray reactor.

It is even more elegant to carry out the above-outlined intermediate heating in a direct way (autothermal method). To this end, a limited amount of molecular oxygen is added to the reaction gas mixture either before it flows through the first catalyst bed (in that case the starting reaction gas mixture should comprise added molecular hydrogen) and/or between the downstream catalyst beds. It is thus possible (generally catalyzed by the dehydrogenation catalysts themselves) to bring about a limited combustion of molecular hydrogen which is present in the reaction gas mixture, has been formed in the course of the heterogeneously catalyzed propane dehydrogenation and/or has been added to the reaction gas mixture (it may also be appropriate from an application point of view to insert catalyst beds in the tray reactor which are charged with catalyst which particularly specifically (selectively) catalyzes the combustion of hydrogen (examples of useful catalysts include those of the documents U.S. Pat. Nos. 4,788,371, 4,886,928, 5,430,209, 5,530,171, 5,527,979 and 5,563,314; for example, such catalyst beds may be accommodated in the tray reactor in alternation to the beds containing dehydrogenation catalyst). The heat of reaction released thus allows virtually isothermal operation of the heterogeneously catalyzed propane dehydrogenation in a virtually autothermal manner (the gross exothermicity is essentially zero). As the selected residence time of the reaction gas in the catalyst bed is increased, propane dehydrogenation is thus possible at decreasing or substantially constant temperature, which enables particularly long lifetimes between two regenerations.

In general, oxygen feeding as described above should be undertaken in accordance with the invention in such a manner that the oxygen content of the reaction gas mixture, based on the amount of molecular hydrogen contained therein, is from 0.5 to 50 or to 30% by volume, preferably from 10 to 25% by volume. Useful oxygen sources include both pure molecular oxygen and oxygen diluted with inert gas, for example CO, CO$_2$, N$_2$ and/or noble gases, but especially also air and nitrogen oxides. The resulting combustion gases generally have an additional diluting effect and thus promote heterogeneously catalyzed propane dehydrogenation.

In the context of the inventive procedure, the (main and/or secondary or overall) residual gas recycled from separation zone B into reaction zone A is a particularly rich source of molecular oxygen, which would be added in accordance with the invention to the reaction gas mixture in the tray reactor generally after the first catalyst bed has been passed through at the earliest.

The isothermicity of the heterogeneously catalyzed propane dehydrogenation can be further improved by incorporating closed (for example tubular) internals which have favorably, but not necessarily, been evacuated before filling in the spaces between the catalyst beds in the tray reactor. Such internals may also be placed into the particular catalyst bed. These internals contain suitable solids or liquids which evaporate or melt above a certain temperature, thereby consuming heat, and, when the temperature falls below this value, condense again and thereby release heat.

It will be appreciated that reaction zone A of the process according to the invention can also be realized as described in DE-A 10211275 (as a "loop variant"), which forms an integral part of this patent application.

In other words, one embodiment of the process according to the invention is a process in which at least three gaseous, propane-containing feed streams are fed to reaction zone A, of which at least one comprises fresh propane and at least one is (main and/or secondary or overall) residual gas which has been recycled from separation zone B into reaction zone A and comprises molecular oxygen, unconverted propane and any unconverted propylene (unconverted in reaction zone B), and their propane fed in this way is subjected in reaction zone A to a heterogeneously catalyzed (partial) dehydrogenation (in principle, all heterogeneously catalyzed dehydrogenation processes mentioned and detailed in this document are suitable) to obtain a product gas mixture A comprising propane and propylene, with the proviso that a) product gas mixture A is divided into two portions of identical composition and one of the two portions (as dehydrogenation cycle gas) is recycled into reaction zone A as one of the at least three propane-containing feed streams (preferably as a constituent of the charge gas mixture (starting reaction gas mixture) of reaction zone A) and of the other portion of product gas mixture A (preferably all of the other portion) is further treated in accordance with the invention in the first separation zone A, and b) the feeding of the (main and/or secondary or overall) residual gas from separation zone B into reaction zone A along the reaction path of the heterogeneously catalyzed dehydrogenation of propane is undertaken in such a way that, at the feed point, at least 5 mol %, or at least 10 mol %, preferably at least 15 mol %, or at least 20 mol %, more preferably at least 25 mol %, or at least 30 mol %, even more preferably at least 35 mol %, or at least 40 mol %, and at best at least 45 mol %, or at least 50 mol % (but generally less than 70 mol %, frequently less than 60 mol % and often $\geq 50$ mol %) of the (total amount of) propane fed to reaction zone A via the other feed streams has already been converted under dehydrogenating conditions in reaction zone A (particularly preferred process variants are in turn those in which the aforementioned conversion numbers $Z_U$ are each replaced by $Z_U^{Kr}=(Z_U/1+KGV)$). The feed of the (main and/or secondary or overall residual gas from separation zone B into reaction zone A may be at one point, or else distributed over a plurality of points in succession.

Appropriately, at least 10% by volume or 20% by volume of product gas mixture A will be recycled into reaction zone A. However, the amount of product gas mixture A recycled as cycle gas into reaction zone A will not be more than 90% by volume or 80% by volume of product gas mixture A. In other words, the portion of product gas mixture A recycled as cycle gas into reaction zone A may thus be, for example, from 20 to 80% by volume, or from 30 to 70% by volume, or from 40 to 60% by volume or else 50% by volume of product gas mixture A. Particularly advantageously, the proportion is from 50 to 70% by volume.

One means of heating the starting reaction gas mixture fed to reaction zone A to the reaction temperature required for the heterogeneously catalyzed propane dehydrogenation in reaction zone A is to add molecular hydrogen to it and combust it by means of molecular oxygen, for example over suitable specific combustion catalysts (for example those mentioned in this document) (for example by simply passing over and/or passing through), and bringing about the heating to the desired reaction temperature by means of the heat of combustion thus released. The resulting combustion products such as $CO_2$, $H_2O$ and the $N_2$ which if appropriate accompanies the molecular oxygen required for the combustion are advantageously inert diluent gases.

When, along the reaction path of the heterogeneously catalyzed dehydrogenation in reaction zone A, another molecular oxygen-containing gas is conducted into reaction zone A in advance of the recycling of the molecular oxygen-containing residual gas from separation zone B, irrespective of the specific configuration of reaction zone A, it is appropriate in accordance with the invention to make sure that such molecular oxygen added in advance does not too greatly reduce the hydrogen content in the reaction gas mixture in reaction zone A up to the feed point of the residual gas comprising molecular oxygen to be recycled from separation zone B.

According to the invention, the residual gas recycled from separation zone B into reaction zone A may also be the only molecular oxygen-containing gas fed to reaction zone A (irrespective of the specific configuration of reaction zone A). However, this is not the general case in the inventive procedure.

In an inventively elegant manner, reaction zone A will be configured and operated with the proviso that it consists of a first and of a second section (referred to hereinbelow as "two-section variant"), by I. feeding to the first section of reaction zone A at least one feed stream comprising gaseous propane, which comprises fresh propane, and, in this first section of reaction zone A, subjecting the propane fed to it in such a way to a heterogeneously catalyzed dehydrogenation to obtain a product gas mixture A* comprising propane, propylene and molecular hydrogen and which has been obtained by converting under dehydrogenating conditions (with heterogeneous catalysis) at least 5 mol %, or at least 10 mol %, advantageously at least 15 mol %, or at least 20 mol %, more advantageously at least 25 mol %, or at least 30 mol %, even more advantageously at least 35 mol %, or at least 40 mol %, and even better at least 45 mol %, or at least 50 mol % (but generally less than 70 mol %, or less than 60 mol %, or $\leq 50$ mol %) of the (total amount of) propane fed to the first section of reaction zone A in this first section (of reaction zone A) and which, based on the molar amount of propane contained therein, preferably contains a larger molar amount of molecular hydrogen than the starting reaction gas mixture fed to the first section of reaction zone A;

II. subsequently feeding (main and/or secondary or overall) residual gas, comprising molecular oxygen, unconverted propane and any unconverted propylene (unconverted in reaction zone B), from separation zone B (advantageously in accordance with the invention at least half, preferably at least two thirds or three quarters and most preferably the entire amount (if appropriate minus a portion which is recycled as diluent gas into reaction zone B and is of identical composition) of the aforementioned residual gas obtained in separation zone B (in each case individually based on the main and/or secondary or overall residual gas)) to product gas mixture A* and feeding the resulting reaction gas mixture A* to the second section of reaction zone A, and III. in this second section of reaction zone A, with formation of product gas mixture A comprising propane and propylene, combusting molecular oxygen present in reaction gas mixture A* with molecular hydrogen present in reaction gas mixture A* under heterogeneous catalysis to give water (advantageously at least 25 mol %, preferably at least 50 mol %, more preferably at least 75 mol %, better at least 90 mol % and at best at least 95 mol % of the amount of molecular oxygen present in reaction gas mixture A*) and dehydrogenating propane present in reaction gas mixture A*, if appropriate under heterogeneous catalysis, to give propylene (generally less than 40 mol % or less than 30 mol %, usually less than 20 mol %, frequently less than 10 mol % and often less than 5 mol %, of the propane present in reaction gas mixture A*). The aforementioned ratios may be controlled by adjusting the dimensions of the accompanying catalyst bed;

IV. product gas mixture A is then conducted out of reaction zone A and treated further as described in accordance with the invention in the first separation zone A of the process according to the invention (any product gas mixture A not conducted into the first separation zone A may be combusted, for example, for energy generation and/or for the generation of synthesis gas, etc.).

Useful catalysts for the second section of reaction zone A are all of those catalysts which are also recommended in this document for the heterogeneously catalyzed dehydrogenation and are especially suitable also for the first section of reaction zone A, since, as already mentioned at the outset of this document, they are generally also capable of catalyzing the combustion of molecular hydrogen (this is especially true of the catalysts of DE-A 19937107 (especially those listed by way of example); in a competition situation between heterogeneously catalyzed propane dehydrogenation and heterogeneously catalyzed hydrogen combustion, the latter generally proceeds substantially more quickly and dominates the former). It will be appreciated that useful catalysts for the second section of reaction zone A are also those which are tailored specifically to the selective combustion of molecular hydrogen. Such catalysts are, for example, those of the documents U.S. Pat. Nos. 4,788,371, 4,886,928, 5,430,203, 5,530,171, 5,527,979 and 5,563,314.

In principle, the first section of reaction zone A may be configured either isothermally or adiabatically. In the latter case, preference is given to an endothermal to autothermal gross thermal character over the first reaction section of reaction zone A based on single pass of the starting reaction gas mixture added (fed) to the first section of reaction zone A through the first section of reaction zone A.

The reaction conditions in the second section of reaction zone A (reaction temperature (for example from 400 or 500 to 800 or 700° C.), reaction pressure (for example from 1 to 10 or to 5 or to 3 bar) and hourly space velocity on the catalyst bed of reaction gas mixture (for example 500 (or less) to 80 000 (or more) l (STP)/l·h) may in principle be selected similarly to in the first section of reaction zone A.

In principle, the second section of reaction zone A may also be configured isothermally or adiabatically. In the latter case, preference is given to an exothermic gross thermal character over the second reaction section of reaction zone A based on single pass of the starting reaction gas mixture (reaction gas mixture A*) added (fed) to the second section of reaction zone A through the second section of reaction zone A.

Preference is given in accordance with the invention to both the first and the second section of reaction zone A being configured adiabatically, and particular preference is given to the combination of "endothermic to autothermal gross thermal character" in the first reaction section and "exothermic gross thermal character" in the second reaction section.

Particularly advantageous is a configuration of the first section of reaction zone A in tray structure which is operated preferably in accordance with the invention endothermally to autothermally in adiabatic configuration. The tray structure comprises one or more spatially successive catalyst beds charged with dehydrogenation catalyst. The number of catalyst beds may be from 1 to 20, appropriately from 2 to 8, in particular from 3 to 6 (for high dehydrogenation conversions in the first section of reaction zone A, a large number of catalyst beds is advantageous).

The catalyst beds are flowed through preferably radially or axially by reaction gas.

In the simplest case, the fixed catalyst beds are arranged successively in a reactor axially or in the annular gaps of concentric cylindrical grids. The reactor may be, for example, a shaft furnace. The execution of the first section of reaction zone A in a single shaft furnace is just as possible as the realization of the entire reaction zone A in one tray reactor.

If no molecular oxygen-containing gas were to be added to the reaction gas at any point before and/or after entry into the first section of reaction zone A, the reaction gas would appropriately be subjected to intermediate heating in the first section, structured in trays, of reaction zone A on its path from one catalyst bed to the next catalyst bed, for example by passing it over heat exchanger surfaces heated with hot gases, for example heat exchanger ribs, or by passing it through internals heated with hot combustion gases, for example tubes.

In the context of the process according to the invention, the above-outlined intermediate heating is, however, preferably carried out at least partly by a direct route. To this end, a limited amount of a molecular oxygen-containing gas (preferably air or mixtures of oxygen and inert gases such as $CO_2$, $N_2$ and noble gases, or pure $O_2$) is added to the reaction gas either before it flows through the first catalyst bed and/or between the downstream catalyst beds.

At one, or at a plurality of, or if appropriate at all, catalyst beds, a limited amount of molecular hydrogen added beforehand to the reaction gas and/or formed in the course of the dehydrogenation is combusted. The heat of reaction released thus enables, in the case of adiabatic configuration, a substantially autothermal operating mode of the first section of reaction zone A. Based on the amount of molecular hydrogen present in the reaction gas, the amount of molecular oxygen added should be from 0.5 to 50 or to 30% by volume (preferably from 10 to 25% by volume). Owing to the high heat of combustion of the hydrogen, a partial combustion of comparatively small amounts thereof is generally sufficient for the aforementioned purpose.

In one embodiment of the invention, oxygeneous gas is, if appropriate, fed intermediately upstream of each tray of the tray reactor. In a further embodiment of the process according to the invention, oxygeneous gas is fed upstream of each tray except for the first tray. In a further embodiment of the process according to the invention, a bed of specific oxidation catalyst suitable for the purposes of $H_2$ oxidation is present downstream of each oxygen feed point, followed by a bed of dehydrogenation catalyst. If required, external molecular hydrogen (in pure form or diluted with inert gas) may if appropriate additionally be fed upstream of each tray. In a less preferred embodiment, the catalyst beds may also comprise mixtures of dehydrogenation and $H_2$ oxidation catalysts.

However, it is essential to the invention that no feeding of external molecular hydrogen is necessarily required in the process according to the invention. The dehydrogenation temperature in the tray structure (in the tray reactor) is generally from 400 to 800° C., the pressure is generally from 0.2 to 10 bar, preferably from 0.5 to 4 bar and more preferably from 1 to 3 bar. The overall gas hourly space velocity (GHSV) is generally from 500 to 10 000 $h^{-1}$, even up to 80 000 $h^{-1}$ in the case of high-load operation, regularly from 30 000 to 40 000 $h^{-1}$.

Presence of steam promotes the catalyst lifetime.

Partial pressure reduction of the reactants by pressure reduction, combustion of hydrogen formed in the dehydrogenation and/or inert dilution, high temperatures and a large number of trays promotes the conversion of the dehydrogenation within the first section of reaction zone A.

For the second section of reaction zone A, preference is given to employing the same reactor type as for the first section of reaction zone A. However, it generally contains only one catalyst bed. Preference is given to using simple shaft furnaces in both sections.

The molar ratio of molecular oxygen to molecular hydrogen (in reaction gas mixture A*) in the second section of reaction zone A may be from 1:2 to 1:10, preferably from 1:2 to 1:4. In other words, in the second section of reaction zone A, substantially all of the molecular oxygen present in reaction gas mixture A* may be combusted with molecular hydrogen to give water, so that the product gas mixture A formed is substantially free of molecular oxygen. For example, the thus formed product gas mixture A may contain less than 5% by volume, or less than 3% by volume, or less than 1% by volume, in many cases even less than 0.5 or less than 0.2% by volume of molecular oxygen. Preference is given to a negligible content of molecular oxygen.

The first section of reaction zone A and the second section of reaction zone A may be accommodated either in separate reactors or in a single reactor (for example in a tray reactor, for example in shaft furnace design).

In an even more elegant manner in accordance with the invention, reaction zone A can be configured and operated as a combination of the above-described "loop variant" and the "two-section variant" as follows.

In this case, the product gas mixture A formed in the second section of reaction zone A in the "two-section variant" as described above will additionally be divided into two portions of identical composition and one of the two portions (as dehydrogenation cycle gas) will be recycled as a further propane-containing feed stream into the first section of reaction zone A (preferably as a constituent of the starting reaction gas mixture of the first section of reaction zone A) and of the other portion of product gas mixture A (preferably the entire other portion) will be further treated in accordance with the invention in the first separation zone A.

The recycling of product gas mixture A into the first section of reaction zone A is advantageous in accordance with the invention in that the product gas mixture A formed in the second section of reaction zone A, owing to the combustion of molecular oxygen with molecular hydrogen, firstly normally has (at least in the case of adiabatically exothermic operation of the second section of reaction zone A) an elevated temperature and secondly, likewise owing to the oxygen combustion, a low oxygen content and a significant steam content. The hydrogen contents are generally likewise low. Especially at relatively low dehydrogenation conversions in the first section of reaction zone A, it is possible to supplement reaction gas mixture A* before it is fed into the second section of reaction zone A by adding to it external molecular hydrogen (this is molecular hydrogen which is itself neither a constituent of cycle gas recycled into reaction zone A nor is formed in reaction zone A (or in one of the other reaction/separation zones of the process according to the invention)), in order then to attain, for example, the desired temperature of reaction gas mixture A (and elimination of molecular oxygen therein) in the second section of reaction zone A.

According to the above, such product gas mixture A recycled into the first section of reaction zone A as a constituent of the starting reaction gas mixture is particularly suitable to heat the starting reaction gas mixture fed to the first section of reaction zone A to reaction temperature without simultaneously burdening the starting reaction gas mixture thermodynamically with molecular hydrogen already present or kinetically by molecular oxygen present. The steam present in the recycled product gas mixture A additionally promotes the heterogeneously catalyzed dehydrogenation in the first section of reaction zone A and makes a separate feed of external steam generally superfluous.

In other words, one notable feature of the inventive procedure is that it enables an inventive operating mode with sufficient on-stream time without any of the reaction or separation zones requiring the feed of external steam (this is steam which is not formed in any of the reaction/separation zones of the process according to the invention).

The portion, conducted into the first separation zone A, of the product gas mixture A formed in the second section of reaction zone A is, owing to its elevated temperature, simultaneously outstandingly suitable for warming (substantially to the desired reaction temperature) both initially the fresh propane fed to reaction zone A and the residual gas recycled from separation zone B into reaction zone A (or only one of the two gases) by indirect heat exchange in a gas cooler, while itself simultaneously being cooled in a manner advantageous for the requirements in the first separation zone A.

Appropriately in accordance with the invention, at least 10% by volume or 20% by volume of the product gas mixture A formed in the second section will be recycled into the first section of reaction zone A. Advantageously in accordance with the invention, the portion of product gas mixture A recycled as cycle gas into the first section of reaction zone A will, however, not be more than 90% by volume or 80% by volume. In other words, the portion, recycled as cycle gas into the first section of reaction zone A, of product gas mixture A may in the aforementioned procedure, for example, be from 20 to 80% by volume, or from 30 to 70% by volume, or from 40 to 60% by volume, or else 50% by volume, of the product gas mixture A formed. A particularly advantageous (dehydrogenation) cycle gas proportion is from 50 to 70% by volume.

In a very particularly elegant manner, the recycling of aforementioned product gas mixture A into the first section of reaction zone A can be configured as follows.

Initially, the (main and/or secondary or overall) residual gas, comprising molecular oxygen, propane and any unconverted propylene (unconverted in reaction zone B), from separation zone B will be fed to product gas mixture A by the principle of a jet pump operated with this residual gas as the driving jet (FIG. 1 of DE-A 10211275 illustrates this principle; in this document, it should also include the principle of the ejector jet nozzles), and the conveying direction of the driving jet decompressed through a driving nozzle (1) via a mixing zone (2) and a diffuser (3) points into the second section of reaction zone A, and the sucking action (sucking direction) of the sucking nozzle (4) points in the direction of the first section of reaction zone A, and the "sucking nozzle-mixing zone-diffuser" connection forms the sole connection between the two sections of reaction zone A.

This causes the generation of reduced pressure in the sucking nozzle, by which product gas mixture A* is sucked in from the first section of reaction zone A and, while simultaneously mixing with the driving jet, is transported as reaction gas mixture A* through the mixing zone (the mixing tube) via the diffuser and released into the second section of reaction zone A (the numerical addresses relate to FIG. 1 of this document).

The pressure of the driving jet will necessarily be selected (the pressure setting will normally be effected by means of a radial compressor or (in relatively rare cases) by means of a blower (normally an axial compressor with lower pressure ratio of final pressure to starting pressure)) in such a way that the pressure of the product gas mixture A forming in the second section of reaction zone A is above the pressure of the product gas mixture A* which forms in the first section of reaction zone A. A simple tube connection between the outlet of the second section of reaction zone A and the inlet into the first section of reaction zone A, which will appropriately be designed as a T-piece with quantitative divider, in order to pass a portion of product gas mixture A into the first separation zone A, is normally sufficient to generate a cycle flow (a type of natural circulation), recycling (following the pressure gradient) into the first section of reaction zone A, of the other portion of product gas mixture A.

A very particularly preferred embodiment of reaction zone A of the process according to the invention is therefore configured as follows and is illustrated schematically in FIG. 1 of this document, to which all numerical addresses relate.

Reaction zone A (17) is configured and operated, as already described, as a combination of the above-described "loop variant" and "two-section variant", and the following measures are additionally fulfilled:

I. at least one feed stream comprising gaseous propane, which comprises fresh propane (5), is fed to the first section (0) of reaction zone A, and, in this first section of reaction zone A, the propane fed to it is subjected to a heterogeneously catalyzed (partial) dehydrogenation to obtain a product gas mixture A* which comprises propane, propylene and molecular hydrogen and which has been obtained by converting under dehydrogenating conditions at least 5 mol %, or at least 10 mol %, advantageously at least 15 mol %, or at least 20 mol %, more advantageously at least 25 mol %, or at least 30 mol %, very particularly advantageously at least 35 mol %, or at least 40 mol %, and even better at least 45 mol %, or at least 50 mol % (but generally less than 70 mol %, or less than 60 mol %, or $\leq$50 mol %) of the (total amount of) propane fed to the first section of reaction zone A in this first section (in the case of loop operation in reaction zone A, preferred process variants are in turn those in which the aforementioned conversion numbers $Z_U$ are each replaced by $Z_U^{Kr}=(Z_U/1+KGV)$);

the first section of reaction zone A is operated substantially adiabatically (i.e. heat is essentially neither (deliberately) fed to nor removed from the first section of reaction zone A via heat carriers disposed outside the first section of reaction zone A);

based on single pass of the charge gas mixture of the first section of reaction zone A through the first section of reaction zone A, the gross thermal character over the first section of reaction zone A is endothermic (negative) to autothermic (essentially zero);

the first section of reaction zone A is preferably configured in tray structure;

the tray structure (6) preferably contains from 2 to 20, more preferably from 2 to 10 and most preferably from 2 to 6 catalyst beds which are preferably arranged axially (for example in a shaft furnace) or radially (for example in the annular gaps of concentric cylindrical grids) and are correspondingly flowed through axially or radially by reaction gas;

the tray structure may be realized, for example, in a single reactor or in a series connection of reactors;

the catalyst beds are preferably charged with catalysts (for example those of DE-A 19937107, especially those listed by way of example) in such a way that when the catalyst bed is flowed through by a reaction gas whose composition permits a competition reaction between heterogeneously catalyzed hydrogen combustion and heterogeneously catalyzed propane dehydrogenation, in flow direction, the heterogeneously catalyzed hydrogen combustion initially proceeds more rapidly;

preference is given to feeding to the starting reaction gas mixture fed to the first section of reaction zone A neither external molecular oxygen nor external molecular hydrogen nor external molecular steam (in this document, gas fed externally at any point in reaction zone A (or another reaction/separation zone of the process according to the invention) refers generally to gas which is itself formed neither in reaction zone A (nor in one of the other reaction/separation zones of the process according to the invention) nor is recycled in cycle mode, emerging from reaction zone A, directly and/or indirectly into reaction zone A);

preference is given to adding to the (starting) reaction gas mixture (of the first section of reaction zone A), after it has passed through the first catalyst bed in flow direction, before each pass through a catalyst bed, downstream of the first catalyst bed in flow direction, of the first section of reaction zone A, a limited amount of a molecular oxygen-containing gas, and the amount of oxygen fed in each case to the reaction gas mixture is restricted in each case in such a way that the resulting oxygen content of the reaction gas mixture, based on the hydrogen present therein, is from 0.5 to 50 or to 30% by volume, preferably from 10 to 25% by volume;

preference is given to using air (7) as such an oxygen-containing gas; however, it is also possible to use pure oxygen or a mixture of oxygen and inert gases such as $CO_2$, $N_2$ and/or noble gases or nitrogen oxide;

after the oxygen-containing gas has been added, the reaction gas preferably also passes through a static mixer (8) before it enters the relevant catalyst bed;

the temperatures within the first section of reaction zone A are preferably kept at from 400 to 700° C.;

the working pressure within the first section of reaction zone A is preferably from 0.5 to 10 bar;

the starting reaction gas mixture (9) fed to the first section of reaction zone A (its temperature is preferably from 400 to 700° C. (e.g. 560° C.), its pressure is preferably from 0.5 to 10 bar) preferably has the following contents:

from 10 to 35 (e.g. 19 or 28)% by volume of propane,
from 3 to 10 (e.g. 7.5 or 5.5)% by volume of propene,
from 5 to 20 (e.g. 9 or 12)% by volume of steam,
from 0.01 to 6 (e.g. 3.9 or 4.3)% by volume of molecular hydrogen and
from 0 to 0.02% by volume of molecular oxygen;

the hourly space velocity on the catalyst beds of reaction gas is frequently from 250 to 5000 $h^{-1}$ (in high-load operation even up to 40 000 $h^{-1}$), preferably from 10 000 to 25 000 l (STP)/l·h, more preferably from 15 000 to 20 000 l (STP)/l·h;

in order to heat the fresh propane fed to the first section of reaction zone A to the reaction temperature, it is advantageously conducted in indirect heat exchange (in a gas cooler of customary design) to the hot product gas mixture A conducted out of the second section of reaction zone A into separation zone A;

apart from those already mentioned in this document, preference is given to feeding no further external gases to the first section of reaction zone A;

The product gas mixture A* formed in the first section of reaction zone A preferably has the following contents:

from 8 to 32% by volume (e.g. 16 or 24% by volume) of propane, from 3 to 12% by volume (e.g. 9 or 6% by volume) of propene, from 5 to 23% by volume (e.g. 11 or 15% by volume) of steam, from 0.1 to 6% by volume (e.g. 1 or 3% by volume) of molecular hydrogen, and from 0 to 0.05% by volume of molecular oxygen;

it preferably has a temperature of from 500 to 750° C. (e.g. 580° C.) and advantageously a working pressure of from 0.05 to 10 bar.

II. (main and/or secondary or overall) residual gas, comprising molecular oxygen, propane and any unconverted propylene (unconverted in reaction zone B), from separation zone B is subsequently fed to product mixture A* (advantageously in accordance with the invention at least half, preferably at least three quarters and most preferably the entire amount of the aforementioned residual gas obtained in separation zone B) and the resulting reaction gas mixture A* is fed to the second section of reaction zone A;

the residual gas fed to product gas mixture A* contains generally from 0.5% by volume to 10% by volume, frequently from 1 to 8% by volume and preferably from 2 to 5% by volume of molecular oxygen;

the contents of the (main and/or secondary or overall) residual gas fed to product gas mixture A* are preferably as follows:

from 10 to 40% by volume (e.g. 15 or 32% by volume) of propane, from 0 to 1% by volume of propene, from >0 to 5% by volume (e.g. 3 or 4% by volume) of molecular oxygen, from 1 to 10% by volume (e.g. 2% by volume) of steam, and from 0 to 0.5% by volume (e.g. from 0 to 0.3 or from 0 to 0.1% by volume) of molecular hydrogen;

preference is given to feeding the residual gas to product gas mixture A* in such amounts that the oxygen content of the resulting reaction gas mixture A*, based on the hydrogen present therein, is from 15 to 50% by volume, advantageously from 25 to 50% by volume and more advantageously from 30 or 40 to 50% by volume;

reaction gas mixture A* (12) preferably has the following contents:

from 10 to 38% by volume (e.g. 16 or 28% by volume) of propane, from 3 to 10% by volume (e.g. 5% by volume) of propene, from 0 to 0.05% by volume of molecular oxygen, from 3 to 20% by volume (e.g. 7 or 12% by volume) of steam, and from 0.1 to 6% by volume (e.g. 4% by volume) of molecular hydrogen;

the temperature of reaction gas mixture A* is advantageously from 300 to 600° C. (e.g. from 400 to 500° C.), the pressure of reaction gas mixture A* is advantageously from 0.5 or 0.6 to 12 bar;

the (main and/or secondary or overall) residual gas from separation zone B is preferably fed to product gas mixture A* (11) by the principle of a jet pump operated with this residual gas as the driving jet, and the conveying direction of the driving jet decompressed through a driving nozzle (1) via a mixing zone (2) and a diffuser (3) points into the second section of reaction zone A (13) and the sucking direction (the sucking action) of the sucking nozzle (4) points in the direction of the first section of reaction zone A and the "sucking nozzle-mixing zone-diffuser" connection forms the sole connection between the first and the second section of reaction zone A;

the driving jet preferably has a temperature of from 400 or 500 to 600° C. and a pressure of from 3 to 6 bar (preferably from 4 to 5 bar);

the residual gas (15) conducted out of separation zone B into reaction zone A is preferably heated to this temperature by indirect heat exchange (14) with hot product gas mixture A (16) conducted into separation zone A (preferably after the fresh propane has already been heated with this product gas mixture A);

the residual gas conducted out of separation zone B into reaction zone A is preferably compressed to the aforementioned pressure by means of a radial or axial compressor;

apart from the gas streams mentioned in this document, reaction gas mixture A* preferably does not contain any further added gas streams;

III. in the second section of reaction zone A, with formation of product gas mixture A comprising propane and propylene, molecular oxygen present in reaction gas mixture A* is combusted with molecular hydrogen present therein under heterogeneous catalysis to give water (advantageously at least 25 mol %, preferably at least 50 mol %, more preferably at least 75 mol %, better at least 90 mol % and at best at least 95 mol %, of the amount of molecular oxygen present in reaction gas mixture A*) and any propane present in reaction gas mixture A* is dehydrogenated under heterogeneous catalysis to give propylene (generally less than 40 mol % or less than 30 mol %, usually less than 20 mol %, frequently less than 10 mol % and often less than 5 mol %, of the propane present in reaction gas mixture A*);

the second section of reaction zone A is operated substantially adiabatically (i.e. heat is neither (deliberately) fed to nor withdrawn from the second section of reaction zone A via heat carriers disposed outside the second section of reaction zone A);

based on single pass of reaction gas mixture A* through the second section of reaction zone A, the gross thermal character over the second section of reaction zone A is exothermic (in order to ensure this positive thermal character, it may be appropriate, especially in the case of comparatively small dehydrogenation conversions, in the first section of the reaction zone, to increase the hydrogen content of reaction gas mixture A* by feeding external hydrogen; appropriately from an application point of view, this feed of molecular hydrogen will advantageously be undertaken into product gas mixture A*, but it may also be into the recycled residual gas (19) or into the resulting reaction gas mixture A*);

apart from those already mentioned in this document, preferably no further external gases are fed to the second section of reaction zone A;

the temperatures within the second section of reaction zone A are preferably kept at from 400 to 750° C. (or from 500 to 700° C.);

the working pressure within the second section of reaction zone A is preferably from 0.5 to 12 bar;

for the second section of reaction zone A, suitable catalysts are, for example, those which have also been recommended in this document as being suitable for the heterogeneously catalyzed dehydrogenation in the first section of reaction zone A, since, as already mentioned at the outset of this document, they are generally also capable of catalyzing the combustion of molecular hydrogen (this is especially true of the catalysts of DE-A 19937107 (especially those listed by way of example), which is why these catalysts are used with very particular preference in both sections of reaction zone A; in a competition situation between heterogeneously catalyzed propane dehydrogenation and heterogeneously catalyzed hydrogen combustion, the latter generally proceeds substantially more rapidly over the catalysts mentioned and dominates the former); however, it will be appreciated that useful catalysts for the second section of reaction zone A are also those which are tailored specifically to the selective combustion of molecular hydrogen; such catalysts are, for example, those of the documents U.S. Pat. Nos. 4,788, 371, 4,886,928, 5,430,203, 5,530,171, 5,527,979 and 5,563,314;

useful reactors for the second section of reaction zone A are in principle the same as for the first section of reaction zone A;

the reactor for the second section of reaction zone A preferably does not contain a multitude of catalyst beds, but rather only one catalyst bed;

appropriately from an application point of view, this one catalyst bed is accommodated in a simple shaft furnace and is flowed through axially or radially;

the hourly space velocity on the aforementioned catalyst bed of reaction gas mixture A* is generally from 500 to 80 000 l (STP)/l·h, preferably from 10 000 to 50 000 l (STP)/l·h, more preferably from 20 000 to 40 000 l (STP)/l·h (at only low dehydrogenation conversions in the second section of reaction zone A and predominantly exclusive combustion of molecular oxygen with molecular hydrogen, the aforementioned hourly space velocity may even be up to 200 000 l (STP)/l·h);

advantageously, the first and second section of reaction zone A are accommodated in one and the same reactor;

advantageously from an application point of view, the second section of reaction zone A is a tray filled with catalyst in a tray reactor, whose remaining trays are assigned to the first section of reaction zone A;

the product gas mixture A formed in the second section of reaction zone A preferably has the following contents:

from 7 to 30% by volume (e.g. 12 or 24% by volume) of propane, from 3 to 12% by volume (e.g. 6 or 8% by volume) of propene, from 0 to 0.05% by volume of molecular oxygen, from 5 to 22% by volume (e.g. 10 or 13% by volume) of steam and from 0.1 to 6% by volume (e.g. 4% by volume) of molecular hydrogen.

The temperature of product gas mixture A is advantageously from 400 to 700° C.; the pressure of the reaction gas mixture is advantageously from 0.4 to 10 bar and is preferably simultaneously above the pressure of product gas mixture A*;

IV. the product gas mixture A formed in the second section of reaction zone A is divided into two portions of identical composition and one of the two portions (10) is recycled into the first section of reaction zone A as a further feed stream comprising propane (as dehydrogenation cycle gas) (preferably as a constituent of the starting reaction gas mixture of the first section of reaction zone A and preferably in natural circulation following the pressure gradient existing to the pressure at the outlet of the first section of reaction zone A; the mixing with fresh propane is preferably effected by means of a static mixer upstream of the first catalyst bed, in flow direction, of the first section of reaction zone A) and the other portion (18) of product gas mixture A (preferably the entire other portion) is further treated in accordance with the invention in the first separation zone A;

preference is given to conducting the other portion (18) of product gas mixture A via an indirect heat exchanger (14) into separation zone A in order to heat therein the fresh propane and/or the residual gas from separation zone B (to the desired temperature).

The product gas mixture A formed in reaction zone A in the context of the inventive heterogeneously catalyzed propane dehydrogenation comprises, in the process according to the invention, generally propane, propene, molecular hydrogen, $N_2$, $H_2O$, methane, ethane, ethylene, butene-1, other butenes (e.g. isobutene) and other $C_4$-hydrocarbons (n-butane, isobutane, butadiene, etc.), CO and $CO_2$, but generally also oxygenates such as alcohols, aldehydes and carboxylic acids (normally having $\leq 9$ carbon atoms). In addition, small amounts of constituents stemming from the residual gas may be present, for example secondary components which are formed in reaction zone B, but also absorbent used in separation zones A and/or B. It will generally be at a pressure of from 0.3 to 10 bar and frequently have a temperature of from 400 to 650 or to 500° C., in favorable cases from 450 to 500° C.

While EP-A 117 146, DE-A 3 313 573 and U.S. Pat. No. 3,161,670 recommend the use of the product gas mixture A formed in the heterogeneously catalyzed propane dehydrogenation as such to charge reaction zone B, it is necessary in accordance with the invention to remove at least a portion of the constituents, other than propane and propylene, present therein as a secondary component discharge before it is further used to charge reaction zone B. In this context, the requirements of DE-A 10211275 should be noted. When product gas mixture A still contains significant amounts of molecular hydrogen, the aforementioned removal will generally be accompanied by at least a partial removal of the hydrogen or such a hydrogen removal will advantageously be carried out beforehand.

The latter may be effected, for example, by passing product gas mixture A, if appropriate after it has been cooled beforehand in an indirect heat exchanger (appropriately, as already mentioned, the heat removed is used in reaction zone A to heat a feed gas required for the process according to the invention), through a membrane which generally has a tubular shape (but a plate or wound module are also possible) and which is permeable only to the molecular hydrogen. The thus removed molecular hydrogen may, if required, be partly recycled into the heterogeneously catalyzed dehydrogenation of propane (i.e. into reaction zone A) and/or fed to another utilization. For example, it may be combusted in fuel cells.

Alternatively, a partial or complete hydrogen removal may also be undertaken by partial condensation, adsorption and/or rectification (preferably under pressure). The partial or full removal of molecular hydrogen from product gas mixture A may also be undertaken in the process according to the invention by selective (for example heterogeneously catalyzed) combustion to be undertaken outside reaction zone A. The water of reaction which is formed may either be removed partly or fully or left in the gas mixture, since it is capable of functioning as an inert diluent gas in reaction zone B. Catalysts which are suitable in this regard are disclosed, for example, by U.S. Pat. Nos. 4,788,371, 4,886, 928, 5,430,209, 5,553,0171, 5,527,979 and 5,563,314.

Appropriately in accordance with the invention, at least 10 mol %, or at least 25 mol %, frequently at least 35 mol %, or at least 50 mol %, in many cases at least 75 mol % and often the entire amount of the molecular hydrogen present in the product gas mixture A conducted out of reaction zone A will be removed beforehand and/or concomitantly before the remaining product gas mixture A' is used to charge reaction zone B. However, it is a very particularly advantageous feature of the latter above-described, very particularly preferred operating mode of reaction zone A, i.e. the combination of "loop variant" and "two-section variant", with adiabatically endothermic configuration of the first section and adiabatically exothermic configuration of the second section (each of reaction zone A), that product gas mixture A is obtained there already substantially free of molecular hydrogen, the molecular hydrogen formed within reaction zone A is advantageously still utilized virtually quantitatively in reaction zone A and the steam formed as a constituent of the portion, recycled into the first section of reaction zone A, of product gas mixture A is likewise fed to an advantageous utilization. If required, it is also possible to partly or fully remove (for example by condensing out) from product gas mixture A any water present therein before it is further processed in reaction zone B. It will be appreciated that, if required, it is also possible in the context of the removal of molecular hydrogen and/or steam, to undertake a removal of other constituents, other than propane and propylene, of product gas mixture A.

A simple means to this end is, for example, to contact (for example by simply passing through) the preferably cooled (preferably to temperatures of from 10 to 100 or 70° C.) product gas mixture A, for example at a pressure of from 0.1 to 50 bar, preferably from 5 to 15 bar and a temperature of, for example, from 0 to 100° C., preferably from 20 to 40° C., with a (preferably high-boiling) organic solvent (preferably hydrophobic) in which propane and propylene (appropriately preferentially over the other constituents of product gas mixture A) are absorbed. Subsequent desorption, rectification and/or stripping with a gas which behaves inertly with regard to reaction zone B and/or is required as a reactant in this reaction zone (for example air or another mixture of molecular oxygen and inert gas) recover the propane and propylene in a mixture in purified form which are then used to charge reaction zone B (the procedure is preferably as described in comparative example 1). The offgas, in some cases comprising molecular hydrogen, of the absorption may, for example, be subjected again to a membrane separation and then, if required, the hydrogen removed may also be used in the heterogeneously catalyzed propane dehydrogenation in reaction zone A.

However, the C3 hydrocarbons/C4 hydrocarbons separation factor in the above separation process is comparatively limited and frequently insufficient for the needs described in DE-A 10245585.

As an alternative for the separation step via absorption described, preference is therefore frequently given to a pressure swing adsorption or a pressure rectification for the inventive purposes.

Suitable absorbents for the above-described absorptive removal are in principle all absorbents which are capable of absorbing propane and propylene. The absorbent is preferably an organic solvent which is preferably hydrophobic and/or high-boiling. Advantageously, this solvent has a boiling point (at a standard pressure of 1 atm) of at least 120° C., preferably of at least 180° C., preferentially of from 200 to 350° C., in particular from 250 to 300° C., more preferably from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not contain any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols containing from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyldiphenylmethane and its isomers, 2-methyl-2'-benzyldiphenylmethane, 2-methyl-4'-benzyldiphenylmethane and 4-methyl-2'-benzyldiphenylmethane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example from Bayer Aktiengesellschaft). Frequently, this solvent mixture comprises a solvent such as dimethyl phthalate added in an amount of from 0.1 to 25% by weight based on the entire solvent mixture. Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent $\leq 300$ g/mol. Also suitable are the paraffin oils, described in DE-A 33 13 573, having from 8 to 16 carbon atoms. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type.

The performance of the absorption is subject to no particular restrictions. It is possible to use all common processes and conditions known to those skilled in the art. Preference is given to contacting the gas mixture with the absorbent at a pressure of from 1 to 50 bar, preferably from 2 to 20 bar, more preferably from 5 to 15 bar, and a temperature of from 0 to 100° C., in particular from 20 to 50 or 40° C. The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000, or to 750 $m^2/m^3$, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and the propylene may be removed from the absorbent by stripping, flash evaporation (flashing) and/or distillation.

The propane and propylene are preferably removed from the absorbent by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 30 to 50° C. An example of a gas suitable for the stripping is steam, but preference is given in particular to oxygen/nitrogen mixtures, for example air. When air or oxygen/nitrogen mixtures are used in which the oxygen content is above 10% by volume, it may be sensible to add a gas before and/or during the stripping process which reduces the explosion range. Particularly suitable for this purpose are gases having a specific heat capacity of $\geq 29$ J/mol·K at 20° C., for example methane, ethane, propane, propene, benzene, methanol, ethanol, and ammonia, carbon dioxide and water. However, preference is given in accordance with the invention to avoiding C4 hydrocarbons as such additives. Particularly suitable for the stripping are also bubble columns with and without internals.

The propane and propylene may also be removed from the absorbent by a distillation or rectification, in which case the columns which are familiar to those skilled in the art and have structured packings, random packings or appropriate internals can be used. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to charge reaction zone B, a gas mixture obtained from the absorbent by stripping may be fed to a further process stage, in order, for example, to reduce the losses of entrained absorbent (for example separation in demisters and/or depth filters) and to thus simultaneously protect reaction zone B from absorbent or in order to further improve the separating action between C3/C4 hydrocarbons. Such removal of the absorbent may be effected by all process steps known to those skilled in the art. In the context of the process according to the invention, an example of a preferred embodiment of such a removal is the quenching of the outlet stream from the stripping apparatus with water. In this case, the absorbent is washed out of this laden outlet stream with water and the outlet stream is simultaneously laden with water. This scrubbing or the quenching may be effected, for example, at the top of a desorption column using a liquid collecting tray by counterspraying of water or in a dedicated apparatus.

To support the separating effect, it is possible to install internals which increase the quench surface area in the quench chamber, as are known to those skilled in the art from rectifications, absorptions and desorptions.

Water is a preferred scrubbing agent in that it normally does not interfere in the downstream at least one partial zone. After the water has washed the absorbent out of the outlet stream laden with propane and propylene, the water/absorbent mixture may be fed to a phase separation and the treated outlet stream fed directly to reaction zone B.

Both the absorbent stripped to substantially free it of C3 and the absorbent recovered in the phase separation may be reused for the absorption task.

The gas mixture which comprises propane and propene and is obtained in a removal which can be carried out as described by way of example can thus be used in a manner known per se to charge a heterogeneously catalyzed gas phase partial oxidation of propylene to acrolein and/or acrylic acid, as described, for example, in WO 01/96270 and in the documents DE-A 10245585, DE-A 10246119, DE-A 10313210, DE-A 10313214, DE-A 10313213, DE-A 10313212, DE-A 10308824, DE-A 10313208 and DE-A 10211275. The oxidizing agent added may be pure molecular oxygen, air, oxygen-enriched air or any other mixture of oxygen and inert gas.

In the process according to the invention, the composition of the charge gas mixture (cf. DE-A 10245585 and DE-A 10246119) for reaction zone B will be adjusted in such a way that the following molar ratios are fulfilled:

Propane:propene:$N_2$:$O_2$:$H_2O$:others=0.5 to 20:1:0.1 to 40:0.1 to 10:0 to 20:0 to 1.

Advantageously, the aforementioned molar ratios are, in accordance with the invention, =1 or 2 to 10:1:0.5 to 20:0.5 to 5:0.01 to 10:0 to 1.

It is also favorable when the aforementioned molar ratios are, in accordance with the invention, =3 to 6:1:1 to 10:1 to 3:0.1 to 2:0 to 0.5.

In a manner known per se, the heterogeneously catalyzed gas phase partial oxidation of propylene to acrylic acid with molecular oxygen proceeds in two steps successive along the reaction coordinate, the first of which leads to acrolein, and the second from acrolein to acrylic acid.

This reaction sequence in two steps successive in time opens up the possibility in a manner known per se of implementing reaction zone B of the process according to the invention in this case in two stages, i.e. in two oxidation zones arranged in series, in which case the oxidic catalyst to be used in each of the two oxidation zones can be optimized (the reaction may also be terminated at the stage of acrolein). For instance, for the first oxidation zone (propylene→acrolein), preference is generally given to a catalyst based on multimetal oxides comprising the Mo—Bi—Fe element combination, while preference is normally given for the second oxidation zone (acrolein→acrylic acid) to catalysts based on multimetal oxides containing the Mo—V element combination.

Corresponding multimetal oxide catalysts for both oxidation zones have been described many times before and are well known to those skilled in the art. For example, EP-A 253 409 on page 5 refers to corresponding US patents.

Favorable catalysts for the two oxidation zones are also disclosed by DE-A 4 431 957, DE-A 102004025445 and DE-A 4431949. This is especially true of those of the general formula I in both aforementioned documents. Particularly advantageous catalysts for both oxidation zones are disclosed by the documents DE-A 10325488, DE-A 10325487, DE-A 10353954, DE-A 10344149, DE-A 10351269, DE-A 10350812, DE-A 10350822.

The aforementioned documents also disclose gas phase partial oxidation processes suitable in accordance with the invention.

For the first step of the partial oxidation, the heterogeneously catalyzed gas phase partial oxidation of propylene to acrolein, useful multimetal oxide compositions are, as already stated, in principle all multimetal oxide compositions containing Mo, Bi and Fe.

These are in particular the multimetal oxide active compositions of the general formula I of DE-A 19955176, the multimetal oxide active compositions of the general formula I of DE-A 19948523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168 and also the multimetal oxide active compositions specified in EP-A 700714.

Also suitable for this oxidation step are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This applies in particular to the exemplary embodiments in these documents, and among these particular preference is given to those of EP-A 15565, EP-A 575897, DE-A 19746210 and DE-A 19855913. Particular emphasis is given in this context to a catalyst according to example 1c from EP-A 15565 and also to a catalyst to be prepared in a corresponding manner but whose active composition has the composition $Mo_{12}Ni_{6.5}Zn_2Fe_2Bi_1P_{0.0065}K_{0.06}O_x \cdot 10SiO_2$. Emphasis is also given to the example having the serial number 3 from DE-A 19855913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein can be encompassed by the general formula IV $$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4023239) and are customarily shaped in substance to give spheres, rings or cylinders or else used in the form of coated catalysts, i.e. preshaped inert support bodies coated with the active composition. It will be appreciated that they may also be used as catalysts in powder form.

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

It will be appreciated that the pulverulent active composition or its pulverulent precursor composition which is yet to be calcined and/or partially calcined may also be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is appropriately moistened and dried again after application, for example by means of hot air. The coating thickness of the powder composition applied to the support body is appropriately selected within the range from 10 to 1000 µm, preferably within the range from 50 to 500 µm and more preferably within the range from 150 to 250 µm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length× internal diameter). It will be appreciated that the fineness of the catalytically active oxide compositions to be applied to the surface of the support body is adapted to the desired coating thickness (cf. EP-A 714 700).

Multimetal oxide active compositions to be used for the step from propylene to acrolein are also compositions of the general formula V $$[Y^1_a Y^2_b O_x]_p [Y^3_c Y^4_d Y^5_e Y^6_f Y^7_g Y^2_h O_y]_q \quad (V)$$

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10,
comprising three-dimensional regions of the chemical composition $Y^1_a Y^2_b O_{x'}$ which are delimited from their local environment owing to their different composition from their local environment, and whose maximum diameter (longest direct line passing through the center of the region and connecting two points on the surface (interface) of the region) is from 1 nm to 100 µm, frequently from 10 nm to 500 nm or from 1 µm to 50 or 25 µm.

Particularly advantageous inventive multimetal oxide compositions V are those in which $Y^1$ is only bismuth.

Among these, preference is given in turn to those of the general formula VI $$[Bi_{a''} Z^2_{b''} O_{x''}]_{p''} [Z^2_{12} Z^3_{c''} Z^4_{d''} Fe_{e''} Z^5_{f''} Z^6_{g''} Z^7_{h''} O_{y''}]_{q''} \quad (VI)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h''=from 0 to 1,
x'',y''=numbers which are determined by the valency and frequency of the elements in VI other than oxygen,
p'',q''=numbers whose p''/q'' ratio is from 0.1 to 5, preferably from 0.5 to 2,
and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably 100 mol %) of the total proportion of $[Y^1_a Y^2_b O_{x'}]_p ([Bi_a Z^2_{b''} O_{x''}]_{p''})$ of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_a Y^2_b O_{x'} [Bi_{a''} Z^2_{b''} O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide active compositions V is described, for example, in EP-A 575897 and also in DE-A 19855913.

The inert support materials recommended above are also useful, inter alia, as inert materials for the dilution and/or delimitation of the appropriate fixed catalyst beds, or as a preliminary bed which protects them and/or heats the gas mixture.

It should be mentioned at this point that all catalysts and multimetal oxide compositions which have been recommended as suitable for the step from propylene to acrolein are in principle also suitable for the partial ammoxidation of propylene to acrylonitrile.

For the second step, the heterogeneously catalyzed gas phase partial oxidation of acrolein to acrylic acid, useful active compositions are, as already stated, in principle all multimetal oxide compositions containing Mo and V, for example those of DE-A 10046928.

A multitude thereof, for example those of DE-A 19815281, can be encompassed by the general formula VII

  (VII)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII

  (VIII)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 4335973 or in EP-A 714700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. It will be appreciated that the unsupported catalyst may also have spherical geometry, in which case the spherical diameter may be from 2 to 10 mm (e.g. 8.2 mm or 5.1 mm).

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2909671, EP-A 293859 or by EP-A 714700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Favorable multimetal oxide active compositions to be used for the "acrolein→acrylic acid" step are also compositions of the general formula IX $$[D]_p[E]_q \quad (IX)$$

in which the variables are each defined as follows:
$D=Mo_{12}V_{a''}Z^1_{b''}Z^2_{c''}Z^3_{d''}Z^4_{e''}Z^5_{f''}Z^6_{g''}O_{x''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or $B^1$,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a"=from 1 to 8,
b"=from 0.2 to 5,
c"=from 0 to 23,
d"=from 0 to 50,
e"=from 0 to 2,
f"=from 0 to 5,
g"=from 0 to 50,
h"=from 4 to 30,
i"=from 0 to 20 and
x",y"=numbers which are determined by the valency and frequency of the elements in IX other than oxygen and
p,q=numbers other than zero whose p/q ratio is from 160:1 to 1:1,
and which are obtainable by separately preforming a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the above-mentioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668104, DE-A 19736105, DE-A 10046928, DE-A 19740493 and DE-A 19528646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 19815281, especially having multimetal oxide active compositions of the general formula I of this document.

Advantageously, unsupported catalyst rings are used for the step from propylene to acrolein and coated catalyst rings for the step from acrolein to acrylic acid.

The first step of the partial oxidation, from propylene to acrolein, may be carried out with the catalysts described, for example, in a single-zone multiple catalyst tube fixed bed reactor, as described by DE-A 4431957.

The oxidant used is oxygen. When $N_2$ is selected as the inert diluent gas, the use of air as the oxygen source is found to be particularly advantageous.

Frequently, a propylene:oxygen:inert gas (including steam) volume (l (STP)) ratio of 1:(1.0 to 3.0):(5 to 25), preferably 1:(1.7 to 2.3):(10 to 15) is used. The reaction pressure is typically in the range from 1 to 3 bar and the overall space velocity is preferably from 1500 to 4000 or 6000 l (STP)/l·h or more. The propylene loading is typically from 90 to 200 l (STP)/l·h or to 300 l (STP)/l·h or more.

The flow to the single-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Example 1 of DE-A 10046957 or according to Example 3 of DE-A 10046957 and the inert material used is steatite rings having the geometry 7 mm×7 mm×4 mm (external diameter×height×internal diameter). With regard to the salt bath temperature, the statements of DE-A 4431957 apply.

However, the first step of the partial oxidation, from propylene to acrolein, may also be carried out with the catalysts described, for example, in a two-zone multiple catalyst tube fixed bed reactor as described by DE-A 19910506. In both of the above-described cases, the propene conversion achieved on single pass is normally at values of $\geq 90$ mol %, or $\geq 95$ mol %. The performance of the second step of the partial oxidation, from acrolein to acrylic acid, may be carried out with the catalysts described, for example, in a single-zone multiple catalyst tube fixed bed reactor as described by DE-A 4431949.

In general, the product mixture of the propylene partial oxidation to acrolein is conducted as such (if appropriate on completion of intermediate cooling thereof), i.e. without secondary component removal, into the acrolein oxidation to acrylic acid.

The oxygen required for the second step of the partial oxidation is preferably added in the form of air and is generally added directly to the product gas mixture of the propylene partial oxidation (however, it may also already be present in the starting reaction gas mixture for the propylene partial oxidation).

In general, the charge gas mixture of such an acrolein partial oxidation then has the following composition: acrolein:oxygen:steam:inert gas volume ratio (1 (STP)) of 1:(1 to 3):(0 to 20):(3 to 30), preferably of 1:(1 to 3):(0.5 to 10):(7 to 18).

Here too, the reaction pressure is generally from 1 to 3 bar and the overall space velocity is preferably from 1000 to 3800, or to 4800 l (STP)/l·h or more. The acrolein loading is typically from 80 to 190, or to 290 l (STP)/l·h or more.

The flow to the one-zone multiple catalyst tube fixed bed reactor of the charge gas mixture is preferably likewise from above. The heat exchange medium used in the second stage is appropriately also a salt melt, preferably consisting of 60% by weight of potassium nitrate ($KNO_3$) and 40% by weight of sodium nitrite ($NaNO_2$) or of 53% by weight of potassium nitrate ($KNO_3$), 40% by weight of sodium nitrite ($NaNO_2$) and 7% by weight of sodium nitrate ($NaNO_3$). Viewed over the reactor, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes from bottom to top as follows:

first, to a length of from 50 to 80 or to 70% of the catalyst tube length, either only catalyst or a mixture of catalyst and inert material, the latter, based on the mixture, making up a proportion by weight of up to 20% by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case in the heterogeneously catalyzed gas phase partial oxidation of acrolein to acrylic acid (especially at high acrolein hourly space velocities on the catalyst bed and high steam contents of the charge gas mixture), section B may also consist of two successive catalyst dilutions (for the purpose of minimizing hotspot temperature and hotspot temperature sensitivity). From bottom to top initially with up to 20% by weight of inert material followed by from >20% by weight to 50 or to 40% by weight of inert material. In that case, section C is preferably undiluted.

For flow to the catalyst tubes from bottom to top, the catalyst tube charge is appropriately reversed.

The aforementioned charge variant is especially appropriate when the catalysts used are those according to Preparation Example 5 of DE-A 10046928 or those according to DE-A 19815281 and the inert material used is steatite rings having the geometry 7 mm×7 mm×4 mm or 7 mm×7 mm×3 mm (each external diameter×height×internal diameter). With regard to the salt bath temperature, the statements made in DE-A 44 319 49 apply. It is generally selected such that the acrolein conversion achieved on single pass is normally $\geq 90$ mol %, or $\geq 95$ mol % or $\geq 99$ mol %.

However, the second step of the partial oxidation, from acrolein to acrylic acid, may also be carried out with the catalysts described, for example, in a two-zone multiple catalyst tube fixed bed reactor as described in DE-19910508. For the acrolein conversion, the same applies as was stated above. Also in the case that this second step is carried out in a two-zone multiple catalyst tube fixed bed reactor, the charge gas mixture will appropriately be generated by directly using (as has been described above) the product gas mixture of a partial oxidation directed to the first step (if appropriate on completion of intermediate cooling thereof). The oxygen required for the second step of the partial oxidation is preferably added in the form of air and is added directly in the second case to the product gas mixture of the first step of the partial oxidation.

In the case of a two-stage method with direct further use of the product gas mixture of the first step of the partial oxidation to charge the second step of the partial oxidation, two one-zone multiple catalyst tube fixed bed reactors (in the case of high reactant hourly space velocity on the catalyst bed, as is quite generally the case, preference is given to a cocurrent method between reaction gas and salt bath (heat carrier) viewed over the tube bundle reactor) of the two two-zone multiple catalyst tube fixed bed reactors will generally be connected in series. A mixed series connection (one-zone/two-zone or vice versa) is also possible.

Between the reactors may be disposed an intermediate cooler which may if appropriate contain inert beds which may exert a filter function. The salt bath temperature of multiple catalyst tube reactors for the first step of the partial oxidation from propylene to acrylic acid is generally from 300 to 400° C. The salt bath temperature of multiple catalyst tube reactors for the second step of the partial oxidation from propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their inlet and their outlet temperature is generally $\leq 5°$ C. However, as already mentioned, both steps of the partial oxidation of propylene to acrylic acid may also be implemented in one reactor over one charge as described in DE-A 10121592.

It should also be mentioned once more that a portion of the charge gas mixture for the first step ("propylene→acrolein") may be cycle gas coming from the partial oxidation (residual gas).

This is, as already stated, a molecular oxygen-containing gas which remains after the target product removal (acrolein and/or acrylic acid removal) from the product gas mixture of the partial oxidation and can be recycled partly as inert diluent gas into the charge for the first and/or any second step of the partial oxidation of propylene to acrolein and/or acrylic acid.

However, preference is given to recycling such cycle gas comprising propane, molecular oxygen and any unconverted propylene (residual gas) exclusively in the inventive manner into reaction zone A of the process according to the invention.

It should also be mentioned that an inventive partial oxidation may be carried out in such a way that a reaction gas mixture which does not comprise any oxygen is initially passed over the catalyst charge. In this case, the oxygen required for the partial oxidation is provided as lattice oxygen. In a subsequent regeneration step with an oxygen-containing gas (for example air, oxygen-enriched air or oxygen-depleted air), the catalyst bed is regenerated in order subsequently in turn to be available for an oxygen-free reaction gas mixture, etc.

In summary, a tube bundle reactor within which the catalyst charge changes appropriately along the individual catalyst tubes with completion of the first reaction step (such propylene partial oxidations suitable in accordance with the invention as reaction zone B are taught, for example, by EP-A 911313, EP-A 979813, EP-A 990636 and DE-A 2830765) once again forms the simplest realization form of two oxidation zones for the two steps of the partial oxidation of propylene to acrylic acid. If appropriate, the charge of the catalyst tubes with catalyst is interrupted by an inert bed.

However, preference is given to realizing the two oxidation zones in the form of two tube bundle systems connected in series. These may be disposed in one reactor, in which case the transmission from one tube bundle to the other tube bundle is formed by an (appropriately accessible) bed of inert material which is not accommodated in the catalyst tube. While the catalyst tubes are generally flowed around by a heat carrier, this does not reach an inert bed accommodated as described above. Advantageously, the two catalyst tube bundles are therefore accommodated in spatially separate reactors. In general, there is an intermediate cooler between the two tube bundle reactors in order to reduce any acrolein postcombustion occurring in the product gas mixture which leaves the first oxidation zone. Instead of tube bundle reactors, it is also possible to use plate heat exchanger reactors with salt and/or evaporative cooling, as described, for example, in DE-A 19 929 487 and DE-A 19 952 964.

The reaction temperature in the first oxidation zone is generally from 300 to 450° C., preferably from 320 to 390° C. The reaction temperature in the second oxidation zone is generally from 200 to 370° C., frequently from 220 to 330° C. The reaction pressure in both oxidation zones is appropriately from 0.5 to 5 bar, advantageously from 1 to 3 bar. The hourly space velocity (l (STP)/l·h) on the oxidation catalysts of reaction gas in both oxidation zones is frequently from 1500 to 2500 $h^{-1}$ or to 4000 $h^{-1}$. The hourly space velocity of propylene may be from 100 to 200 or 300 and more l (STP)/l·h.

In principle, the two oxidation zones in the process according to the invention may be configured as described, for example, in DE-A 19 837 517, DE-A 19 910 506, DE-A 19 910 508 and DE-A 19 837 519. Typically, the external heating in the two oxidation zones, if appropriate in multi-zone reactor systems, is adjusted in a manner known per se to the specific reaction gas mixture composition and catalyst charge.

In the case of a two-stage propylene partial oxidation to acrylic acid, it is possible to add the entire amount of molecular oxygen required as an oxidant for the reaction zone B required in accordance with the invention in advance to the charge gas mixture of the propylene oxidation stage in its entirety. However, it will be appreciated that it is also possible to supplement with oxygen after the propylene oxidation stage. Preference is given to the latter in the case of acrylic acid preparation.

In the first oxidation zone (propylene→acrolein), preference is given to setting a molar propylene: molecular oxygen ratio of 1:1 to 3, frequently 1:1.5 to 2. Similar numerical values are suitable for the molar acrolein:molecular oxygen ratio in the second oxidation stage (1:0.5 to 1.5 would be preferred) for the partial oxidation of acrolein to acrylic acid.

In both oxidation zones, an excess of molecular oxygen generally has an advantageous effect on the kinetics of the gas phase oxidation. In contrast to the conditions in reaction zone A of the process according to the invention, the thermodynamic conditions in reaction zone B are substantially not influenced by the molar reactant ratio, since the heterogeneously catalyzed gas phase partial oxidation of propylene to acrylic acid is subject to kinetic control. In principle, it is therefore possible, for example, even to initially charge the propylene in molar excess compared to the molecular oxygen in the first oxidation zone. In this case, the excess propylene actually assumes the role of a diluent gas.

However, the heterogeneously catalyzed gas phase partial oxidation of propylene to acrylic acid can in principle also be realized in a single oxidation zone. In this case, both reaction steps proceed in an oxidation reactor which is charged with a catalyst which is capable of catalyzing the reaction of both reaction steps. It will be appreciated that the catalyst charge may also change continuously or abruptly along the reaction coordinate within the oxidation zone. Of course, it is possible if required in one embodiment of the at least one partial oxidation to be employed in accordance with the invention in the form of two oxidation zones connected in series to partly or fully remove, from the product gas mixture which leaves the first oxidation zone, carbon oxide and steam which are present therein and are formed as a by-product in the first oxidation zone before it is passed on into the second oxidation zone. Preference is given in accordance with the invention to selecting a procedure which does not require such a removal.

Useful sources for the molecular oxygen which is required in the at least one partial oxidation and is added, for example, to product gas mixture A' before it is used to charge reaction zone B are both pure molecular oxygen and molecular oxygen diluted with inert gas such as $CO_2$, CO, noble gases, $N_2$ and/or saturated hydrocarbons, or nitrogen oxide.

Appropriately, at least part of the requirement for molecular oxygen will be covered by using air as the oxygen source.

Metering of cold air to hot product gas mixture A' may also bring about cooling thereof by a direct route in the context of the process according to the invention.

In the long-term operation of the two reaction zones A, B, there will normally be a reduction in the catalyst quality (especially activity and selectivity) of the catalysts employed in the two reaction zones. One way of counteracting this is to regenerate the particular catalyst bed from time to time (to this end, it is also possible in the oxidation zones, for example, to conduct residual gas over the particular catalyst bed of the oxidation catalysts at elevated temperature), as described, for example, in the documents DE-A 10351269, DE-A 10350812 and DE-A 10350822. It is also possible to increase the reaction temperature over the operating time in order to compensate for reduced catalyst activity. However, it has surprisingly been found to be advantageous to increase, in both reaction zones A, B, the particular working pressure in the gas phase, based on identical hourly space velocity on the particular catalyst bed of reaction gas mixture in l (STP)/l·h, during the operating time of the catalyst bed in order to further counteract the deactivation of the catalyst beds, as described, for example, in DE-A 102004025445. For this purpose, it is possible, for example, to mount a pressure regulating device (in the simplest case a throttle device, for example a throttle valve or a vane regulator) downstream of each of the reaction and separation zones to be employed in the process according to the invention (for example partial permeable perforated diaphragms whose holes may successively be partly or fully closed). It will be appreciated that such a pressure regulating device may also be disposed only downstream of one of the zones mentioned. In other words, it is in principle entirely sufficient to introduce the pressure regulating device somewhere in the further flow path of the reaction gas, from where the pressure increase can be propagated into the reaction zones as a result of back pressure. Typical aforementioned pressure increases (which may be undertaken continuously in accordance with deactivation as it proceeds, or else discontinuously) may be up to 3000 mbar and more in the course of the operating time.

The product gas mixture B leaving the reaction zone B to be employed in accordance with the invention is, in the case of a preparation of acrolein and/or acrylic acid, generally substantially composed of the target product, acrolein or acrylic acid or a mixture thereof with acrolein, unconverted molecular oxygen, propane, unconverted propylene, molecular nitrogen, steam formed as a by-product and/or used as a diluent gas, carbon oxides as a by-product and/or used as a diluent gas, and small amounts of other lower aldehydes, lower alkanecarboxylic acids (e.g. acetic acid, formic acid and propionic acid) and also maleic anhydride, benzaldehyde, aromatic carboxylic acids and aromatic carboxylic anhydrides (e.g. phthalic anhydride and benzoic acid), in some cases further hydrocarbons, for example C4 hydrocarbons (e.g. butene-1 and possibly other butenes), and other inert diluent gases.

The target product may be removed from product gas mixture B in a manner known per se in a separating zone B (for example by partial or complete and, if appropriate, fractional condensation of acrylic acid or by absorption of acrylic acid in water or in a high-boiling hydrophobic organic solvent or by absorption of acrolein in water or in aqueous solutions of lower carboxylic acids and subsequent workup of the condensates and/or absorbates; preference is given in accordance with the invention to fractionally condensing product gas mixture B; cf., for example, EP-A 1388533, EP-A 1388532, DE-A 10235847, EP-A 792867, WO 98/01415, EP-A 1015411, EP-A 1015410, WO 99/50219, WO 00/53560, WO 02/09839, DE-A 10235847, WO 03/041833, DE-A 10223058, DE-A 10243625, DE-A 10336386, EP-A 854129, U.S. Pat. No. 4,317,926, DE-A 19837520, DE-A 19606877, DE-A 190501325, DE-A 10247240, DE-A 19740253, EP-A 695736, EP-A 982287, EP-A 1041062, EP-A 117146, DE-A 4308087, DE-A 4335172, DE-A 4436243, DE-A 19 924 532, DE-A 10332758 and DE-A 19 924 533). An acrylic acid removal may also be undertaken as in EP-A 982287, EP-A 982289, DE-A 10336386, DE-A 101 15277, DE-A 19606877, DE-A 19740252, DE-A 19627847, DE-A 10053086 and EP-A 982288. Preference is given to removing as in FIG. 7 of WO/0196271 or in the working examples of the present application.

A common feature of the aforementioned separation processes is (as already mentioned at the outset) that, at the top of the particular separating column comprising separating internals into whose lower section product mixture B is fed, normally after preceding direct and/or indirect cooling, a residual gas stream (main residual gas) normally remains and comprises substantially those constituents of product gas mixture B whose boiling point at standard pressure (1 bar) is ≦−30° C. (i.e. the constituents which are difficult to condense or else are volatile).

In the lower section of the separating column, the less volatile constituents of product gas mixture B, including the particular target product, are normally obtained in a condensed phase.

The residual gas constituents are primarily propane, any propylene unconverted in reaction zone B, molecular oxygen and frequently the inert diluent gases also used in reaction zones A, B, preferably especially nitrogen and carbon dioxide. Depending on the separating process employed, steam may be present only in traces or in amounts of up to 20% by volume or more.

Of this (main) residual gas, at least a portion (which preferably has (main) residual gas composition and) comprises propane, molecular oxygen and any unconverted propylene (unconverted in reaction zone B) (preferably the entirety, but in some cases also only half, or two thirds, or three quarters of this entirety) is recycled in accordance with the invention into reaction zone A as a propane-containing feed stream. However, (main) residual gas portions may also, as already described, be recycled into reaction zone B and/or be combusted for the purpose of energy generation.

In the workup of the condensed phase (for the purpose of removing the target product), it is possible in accordance with the invention (as already mentioned) that further residual gases are obtained, since an attempt is normally made to recycle the entire amount of unconverted propane present in product gas mixture A into reaction zone A and to recover it in the context of target removal. Although these generally contain propane and in some cases propylene, they frequently no longer contain any molecular oxygen (when they do still contain molecular oxygen, they are referred to in this document as secondary residual gases). They may therefore if appropriate be recycled into the inventive reaction zone A combined with the main residual gas to give an overall residual gas. However, it is also possible to separately utilize such further residual gases. For example, they may, as long as they are free of molecular oxygen, generally after compression, also be recycled into reaction zone A as a constituent of the starting reaction gas mixture of reaction zone A. It is also possible to recycle them into reaction zone A at another point when they are substantially free of molecular oxygen.

The preferably complete recycling of the (main and/or secondary or overall) residual gas from separation zone B, which may comprise a connection of a plurality of separating columns and, if appropriate, further separating apparatus other than columns, into reaction zone A, when the process according to the invention is performed continuously, thus results in continuous conversion of propane to acrylic acid and/or acrolein.

It is essential to the invention that the inventive recycling of the (main and/or secondary or overall) residual gas from separation zone B into reaction zone A can achieve a conversion of propane to propylene in the latter with virtually one hundred percent selectivity.

The inventive procedure is advantageous both at low (≦30 mol %) and at high (≦30 mol %) dehydrogenation conversions (based on single pass of the reaction gas mixture through reaction zone A). This is essentially because high dehydrogenation conversions in reaction zone A are generally associated with high propylene fractions in product gas mixture A and, resulting therefrom, also increased propylene streams in the charge gas mixture of reaction zone B. The latter normally leads to increased residual oxygen streams in the (main) residual gas which are in turn suitable for combusting the increased amounts of hydrogen associated with the increased dehydrogenation conversions in reaction zone A. In other words, the process according to the invention advantageously comprises a control mechanism which is thus self-optimizing. However, lower overall gas hourly space velocities on the catalyst charge in reaction zone B are possible with higher propane conversions. Generally, it is favorable in accordance with the invention when the hydrogen stream in the reaction gas mixture of reaction zone A at the feed point for the residual gas to be recycled into reaction zone A is in an at least stoichiometric ratio to the oxygen stream in the recycled residual gas.

The process according to the invention can be employed in a corresponding manner when a partial ammoxidation of propene to acrylonitrile is carried out in reaction zone B. It can also be employed correspondingly when the propane is replaced with isobutane in reaction zone A and the resulting isobutene is partially oxidized in a corresponding manner in reaction zone B to methacrolein and/or methacrylic acid.

COMPARATIVE EXAMPLES AND EXAMPLES

Comparative Example 1

A) Configuration of Reaction Zone A (of the Dehydrogenation Stage)

The dehydrogenation stage consisted of three identical tubular reactors which were connected in series and charged in an identical manner with dehydrogenation catalyst.

The individual tubular reactor was a steel tube (stainless steel of DIN materials no. 1.4841) of length 1300 mm, wall thickness 3.6 mm and internal diameter 53.1 mm. The tubular reactors were each flowed through by reaction gas mixture from top to bottom.

At the lower end of each tubular reactor was disposed a support grating made of the same stainless steel. On the support grating was disposed, from bottom to top, the following charge:

175 mm bed length of steatite spheres (diameter 4-5 mm) of steatite C-220 from CeramTec;
21 mm bed length of steatite spheres (diameter 1.5-2.5 mm) of steatite C-220 from CeramTec;
210 mm bed length of dehydrogenation catalyst (Pt/Sn alloy which had been promoted with the elements Cs, K and La in oxidic form and which had been applied to the outer and inner surface of $ZrO_2 \cdot SiO_2$ mixed oxide support extrudates (average length (having a Gaussian distribution in the range from 3 mm to 12 mm with a maximum at approx. 6 mm); diameter: 2 mm) in the elemental stoichiometry (mass ratios including support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in Example 4 of DE-A 10 219 879).
21 mm bed length of steatite spheres (diameter 1.5-2.5 mm) of steatite C-220 from CeramTec; and
finally, the remaining length of the tubular reactor, again a bed of steatite spheres (diameter 4-5 mm) of steatite C-220 from CeramTec.

The exterior of each of the tubular reactors was inserted, for the purposes of a preheating zone, for the first 500 mm of tube length from top to bottom (toward the support grating) into two half-shells made of copper (coating thickness=200 mm) which ensure uniform distribution of the amount of heat supplied and were electrically heated by means of a heating sleeve (from Horst, Heidelberg, Germany, length 500 mm, internal diameter 100 mm) which fully surrounded them.

From bottom to top, each of the tubular reactors, for the purposes of an adiabatic zone, was inserted for a length of 600 mm into in each case two pairs of thermally insulating half-shells (thickness of one half-shell=25 mm) made of MPS-Super G from Microtherm in Germany, which were mounted one on top of the other offset by 90° from one another. The insulating half-shells were in turn surrounded by a cylindrical envelope made of stainless steel (external diameter=173 mm, internal diameter=167 mm), to which was applied, for the purpose of trace heating, a heating sleeve (length=675 mm, internal diameter=173 mm) from Horst, Heidelberg, Germany. In this manner, it was possible in the adiabatic zone to minimize the heat flux from the environment into the reaction tube and out of the reaction tube into the environment.

Into each reaction tube was additionally inserted centrally a 1370 mm-long thermowell (external diameter: 6 mm, internal diameter: 4 mm), into which a multithermoelement (a total of 10 measurement points every 4 cm from the lower end of the reactor upward, thickness 3.2 mm) had been inserted.

Upstream of each individual tubular reactor was connected a steel tube, filled with steatite rings (made of steatite C-220 from CeramTec and of geometry 7 mm×3 mm×3 mm=external diameter×internal diameter×height), of length 1300 mm as a heater. In this tube, the reaction gas mixture was in each case preheated to the inlet temperature of the downstream tubular reactor and simultaneously mixed in an ideal manner. For this purpose, the heater tubes (stainless steel of DIN materials no. 1.4841, wall thickness 3.6 mm, internal diameter 53.1 mm) were electrically heated for the central 1200 mm length of the tube by means of heating sleeves from Horst, Heidelberg, Germany applied to them. The connection between heaters and tubular reactors was brought about by stainless steel tubes (stainless steel of DIN materials No. 1.4841, external diameter 21.3 mm, internal diameter 16.1 mm, length approx. 700 mm) thermally insulated with customary heat insulation materials.

Upstream of the inlet of the reaction gas mixture into the particular heater was mounted a feed tap, through which compressed air could in each case be supplied to the reaction gas mixture. The steady state is described hereinbelow.

To the first dehydrogenation reactor was fed a starting reaction gas mixture composed of 395 g/h of crude propane (first propane-containing feed stream), 500 g/h of water and 3649 g/h of (overall) residual gas as cycle gas (second propane-containing feed stream) at a temperature of 400° C. and a pressure of 2.8 bar.

The crude propane contained:

|  | % by vol. |
| --- | --- |
| Methane | 0 |
| Ethane | 0.31 |
| Ethene | 0.004 |
| Propane | 96.29 |
| Propene (Propylene) | 0.05 |
| $H_2$ | 0 |
| $O_2$ | 0 |
| $N_2$ | 0.94 |
| CO | 0 |
| $CO_2$ | 0 |
| Isobutane | 1.84 |
| n-Butane | 0.56 |
| trans-Butene | 0.0003 |
| Isobutene | 0 |
| cis-Butene | 0.0014 |
| 1-Butene | 0.004 |
| Butadiene | 0 |

The (overall) residual gas (cycle gas) contained:

|  | % by vol. |
| --- | --- |
| Methane | 0.002 |
| Ethane | 0.083 |
| Ethene | 0.021 |
| Propane | 26.56 |
| Propene | 0.129 |
| $H_2$ | 0.033 |
| $O_2$ | 3.01 |
| $N_2$ | 67.38 |
| CO | 0.47 |
| $CO_2$ | 1.92 |
| Isobutane | 0.31 |
| n-Butane | 0.065 |
| trans-Butene | 0 |
| Isobutene | 0.0004 |
| cis-Butene | 0.0014 |
| 1-Butene | 0.0003 |
| Butadiene | 0 |

The composition of the crude propane and all other gas compositions were determined by gas chromatography [HP 6890 with Chem-Station, detectors: FID, TCD, separating columns: $Al_2O_3$/KCL (Chrompak), Carboxen 1010 (Supelco)]. In the case of steam-containing gas mixtures, the steam was condensed out in a water separator by cooling and decompression if appropriate before the gas chromatography analysis. The uncondensed gas was analyzed and all data relates to this gas on a dry basis (i.e. the amount of steam present in the gas mixture which was actually to be analyzed was not taken into account).

The starting reaction gas mixture was generated in an evaporator which was connected upstream of the first heater. The evaporator itself was likewise designed as a heater. To it were fed 395 g/h of gaseous crude propane (65° C., 5 bar), 3649 g/h of (overall) residual gas (cycle gas) (50° C., 2.8 bar) and 500 g/h of water (20° C., 3 bar). The heating of the evaporator was controlled to a gas mixture outlet temperature of 200° C. The evaporator was connected to the first heater in a manner corresponding to that in which the reactors were connected to the heaters.

The heating of the first heater was controlled in such a way that the gas mixture passed from the evaporator into the first heater left the first heater at a temperature of 400° C. (the wall temperature required for this purpose was approx. 440° C.). The starting reaction gas mixture was then conducted into the first tubular reactor and heated further in the preheating zone thereof to a reaction zone inlet temperature of 423.3° C.

When it passed through the first tubular reactor, the temperature of the reaction gas mixture passed through a maximum (known as hotspot temperature) of 549.1° C. (the quantitative data reported here relate to the operating state after 200 operating hours; in the further course of operation, the different temperatures were adjusted such that the conversion based on single pass and the space-time yield remained substantially constant; the corresponding procedure was also used in the first 200 operating hours), which migrated in flow direction in the course of the continuous operation of the experimental plant owing to gradual catalyst deactivation (the migration rate was approx. 0.03 mm/h).

The reaction gas mixture leaving the first dehydrogenation reactor had the following contents:

|  | % by vol. |
| --- | --- |
| Methane | 0.010 |
| Ethane | 0.103 |
| Ethene | 0.023 |
| Propane | 27.2 |
| Propene | 3.05 |
| $H_2$ | 3.3 |
| $O_2$ | 0 |
| $N_2$ | 62.2 |
| CO | 0.053 |
| $CO_2$ | 3.36 |
| Isobutane | 0.34 |
| n-Butane | 0.077 |
| trans-Butene | 0.050 |
| Isobutene | 0.001 |
| cis-Butene | 0.004 |
| 1-Butene | 0.0004 |
| Butadiene | 0.0015 |

Its temperature was 509.1° C. and its pressure was 2.55 bar.

Before entry into the downstream heater, 130 l (STP)/h of compressed air were metered to the reaction gas mixture (23° C., 4.2 bar).

The reaction gas mixture was then heated to 477° C. (2nd reaction zone inlet) by means of the electrical heating means of the heater (wall temperature approx. 540° C.) and the preheating zone of the downstream (second) reaction tube (wall temperature approx. 560° C.). The pressure of the reaction gas mixture at this point was 2.55 bar.

When it passed through the second tubular reactor, the temperature of the reaction gas mixture passed through a maximum of 515.5° C. which migrated in flow direction in the course of the continuous operation of the experimental plant owing to gradual catalyst deactivation (the migration rate was approx. 0.1 mm/h). The reaction gas mixture leaving the second dehydrogenation reactor had the following contents:

|  | % by vol. |
| --- | --- |
| Methane | 0.015 |
| Ethane | 0.11 |
| Ethene | 0.023 |
| Propane | 24.0 |
| Propene | 4.78 |
| $H_2$ | 3.40 |
| $O_2$ | 0 |

-continued

|  | % by vol. |
| --- | --- |
| $N_2$ | 63.84 |
| CO | 0.068 |
| $CO_2$ | 3.29 |
| iso-Butane | 0.28 |
| n-Butane | 0.062 |
| trans-Butene | 0.084 |
| iso-Butene | 0.001 |
| cis-Butene | 0.007 |
| 1-Butene | 0.0003 |
| Butadiene | 0.0016 |

Its temperature was 493.8° C. and its pressure was 2.5 bar.

Before entry into the downstream heater, 195 l (STP)/h of compressed air were metered to the reaction gas mixture (23° C., 4.2 bar).

The reaction gas mixture was then heated to 464° C. (3rd reaction zone inlet) by means of the electrical heating means of the heater (wall temperature approx. 480° C.) and the preheating zone of the downstream (third) reaction tube (wall temperature approx. 480° C.). The pressure of the reaction gas mixture at this point was 2.5 bar.

When it passed through the third tubular reactor, the temperature of the reaction gas mixture passed through a maximum of 492.8° C. which migrated in flow direction in the course of the continuous operation of the experimental plant owing to gradual catalyst deactivation (the migration rate was approx. 0.1 mm/h). The reaction gas mixture leaving the third dehydrogenation reactor had the following contents:

|  | % by vol. |
| --- | --- |
| Methane | 0.020 |
| Ethane | 0.11 |
| Ethene | 0.027 |
| Propane | 22.76 |
| Propene | 5.33 |
| $H_2$ | 2.48 |
| $O_2$ | 0 |
| $N_2$ | 65.5 |
| CO | 0.042 |
| $CO_2$ | 3.25 |
| Isobutane | 0.26 |
| n-Butane | 0.056 |
| trans-Butene | 0.093 |
| Isobutene | 0.001 |
| cis-Butene | 0.008 |
| 1-Butene | 0.0003 |
| Butadiene | 0.002 |

Its temperature was 480.4° C. and its pressure was 2.45 bar.

This resulted in an overall dehydrogenation conversion of the propane over the dehydrogenation stage, based on single pass of the starting reaction gas mixture, of 19.83 mol %.

In the event of advanced deactivation of the dehydrogenation catalyst beds, the process was interrupted and the dehydrogenation catalyst beds were regenerated as described in DE-A 10028582. This was essentially always the case when the hotspot temperature in all three tubular reactors was approx. 580° C.

Surprisingly, the deactivation of the dehydrogenation catalyst beds progressed more slowly at elevated working pressure.

B) Configuration of Separation Zone A

Direct cooling with sprayed cooled water (T=20° C.) cooled the product gas mixture leaving the third dehydrogenation reactor (product gas mixture A) to 40° C. in a direct cooler (quench) in cocurrent (the remaining gaseous mixture was conducted out of the water quench in the opposite direction to the product gas inflow direction). About 75% by weight of the steam present in the product gas mixture (steam was added to the starting reaction gas mixture of the reaction zone A and was formed in the dehydrogenation stage as a result of combustion of hydrogen and also possibly hydrocarbon with atmospheric oxygen; the heat of combustion substantially maintained the reaction temperature in the reaction gas mixture of reaction zone A) condensed out in the course of direct cooling. The condensate which formed was conducted out of the water quench and fed to its disposal by means of level control. Otherwise, the water used for direct cooling was circulated (by pumping), recooled by indirect heat exchange and sprayed again for the purpose of direct cooling.

Instead of the direct cooling with water described, the product gas mixture from the dehydrogenation stage may also initially be cooled by heating the starting reaction gas mixture to be fed to the dehydrogenation stage (to 400° C.) with the product gas mixture in an indirect heat exchanger (for example in a tube bundle heat exchanger in cocurrent or in countercurrent). This cools the product gas mixture of the dehydrogenation stage from about 500° C. to from approx. 200 to 300° C.

A further cooling of the product gas mixture of the dehydrogenation stage can be effected by using it in an indirect heat exchanger to heat the starting gas mixture for the partial oxidation, still to be described hereinbelow, of the propane generated in the dehydrogenation stage, and/or by using it to balance the absorber offgas cooling, still to be described below, in the preferably two-stage expansion thereof by means of expansion turbines, or to compensate for it by advance incipient heating.

Afterward, the product gas mixture is at a temperature of about 180° C. Subsequently, it is possible to cool it to a temperature in the range from 30° C. to 60° C. by means of air and/or surface water coolers.

Droplet separators integrated into the coolers or downstream thereof collect the water condensed out in the course of cooling and feed it to disposal under level control.

The thus cooled and steam-deburdened product gas mixture of the dehydrogenation stage, having a pressure of about 2 bar, was subsequently compressed to a pressure of from 10 to 13 bar.

In an appropriate manner from an application point of view, the compression was carried out in two stages in order to avoid excessively high compression temperatures (this purpose was also served by the cooling carried out in advance; the steam separation additionally deburdens the compressor output to be expended). In the first stage, compression was effected to a pressure of from 4 to 4.5 bar. The outlet temperature of the gas mixture on leaving the compressor was about 115° C.

In a downstream indirect heat exchanger (air cooler or surface water cooler), the gas mixture was cooled again to from 40 to 60° C., in the course of which further steam condensed. Droplet separators collected the condensate and discharged it under level control.

In the second compressor stage, compression was effected starting from a pressure of about 4 bar to an end pressure of from 10 to 13 bar. The outlet temperature on leaving the compressor was about 126° C.

In two further downstream indirect heat exchangers (initially an air cooler (is normally a tube bundle heat exchanger; the gas to be cooled appropriately flows through the tube interior) and then a surface water cooler), the compressed gas mixture was cooled initially to from 40 to 60° C. and then to 30° C. Water which condensed out was again separated and conducted out by means of droplet separators. When it leaves the second compressor, the gas mixture only contains 0.2% by weight of water. The low water content prevents biphasicity in the downstream absorption and the high pressure reduces the amount of absorbent required for the purpose of absorption.

While turbocompressors (non-oil-lubricated, dry-running, contactless compressors) are used on the industrial scale for the purpose of compression (for example of the 12 MH 4B type from Mannesmann DEMAG, Germany), MV 3459 II membrane compressors from Sera were used here. In principle, the compressors may be driven either by electrical motors or by vapor or gas turbines. Frequently, driving by vapor turbines is the most economic. The gas mixture, cooled and compressed as described, was fed to an absorption column directly above the bottom (approx. 4220 g/h). It had the following contents:

|  | % by vol. |
| --- | --- |
| Nitrogen | 64.39 |
| Oxygen | 0.27 |
| Propane | 23.21 |
| Propene | 5.08 |
| Methane | 0.02 |
| Ethane | 0.11 |
| n-Butane | 0.06 |
| Isobutane | 0.17 |
| n-Butene | 0.04 |
| Isobutene | 0.10 |
| 1,3-Butadiene | 0.00 |
| Hydrogen | 3.32 |
| Carbon monoxide | 0.04 |
| Carbon dioxide | 3.16 |

The absorption column consisted of 1.4571 stainless steel. The column internal diameter was 80 mm, the wall thickness 4 mm and the column length 1.70 m.

About 70% of the volume of the absorption column was filled with Montz packing elements (Montz BSH-750, specific surface area 750 m$^2$/m$^3$) as separating internals. The packing elements were directly adjacent and began at the height of ⅕ of the column length from below. The absorption column was neither cooled nor heated externally. At the top of the column, technical-grade tetradecane from Haltermann, Germany, of the PKWF 4/7 AF type was introduced at an introduction temperature of 30° C. as an absorbent (gas chromatography analysis by means of FID detection gave the following GC area % composition at the start (fresh):
n-Tridecane 7.6%,
n-Tetradecane 47.3%,
n-Pentadecane 7.0%,
n-Hexadecane 3.2%,
n-Heptadecane 14.1% and
residual sum 20.7%;
this composition changed in the course (after approx. 3000 h$^{-1}$) of continuous process operation to the following values:
n-Tridecane 2.6%,
n-Tetradecane 39.5%,
n-Pentadecane 9.4%,
n-Hexadecane 4.8%,
n-Heptadecane 23.4% and
residual sum 20.3%.

The trickle density was 15 m$^3$ of absorbent per m$^2$ of free cross-sectional area and hour (=25 kg/h of tetradecane).

The offgas stream conducted from the absorption column to the combustion still contained 1700 ppm by volume of propane and 400 ppm by volume of propene. On the industrial scale, this offgas stream is conducted via an expander (for example an expansion turbine) into the combustion, in order to recover the majority of the compression output expended in the two-stage compression and to recycle it into the two-stage compression. Appropriately, the expansion is also carried out in two stages in order to prevent undesired condensation. The mechanical energy obtained in the decompression may be utilized either directly as a secondary or main drive for one of the compressors and/or to generate electricity.

Before the decompressed absorber offgas is conducted to the combustion, it may be appropriate on the industrial scale to remove the hydrogen present therein. This may be effected, for example, by passing the offgas through a membrane, generally shaped to a tube, which is permeable only to the molecular hydrogen. The thus removed molecular hydrogen may be recycled, for example, into the heterogeneously catalyzed dehydrogenation or fed to another utilization (for example in fuel cells).

In principle, the hydrogen removal may also be undertaken by partial condensation, adsorption and/or rectification (preferably under pressure, for example as a pressure swing adsorption). On the industrial scale, it is additionally generally appropriate to conduct the absorber offgas through the acid water yet to be described below in order to concentrate it.

The absorbate contained the following contents (% by weight based on the weight of the absorbate):

|  | % by weight |
| --- | --- |
| Nitrogen | 0.094 |
| Propane | 2.65 |
| Propene | 0.55 |
| Ethane | 0.006 |
| n-Butane | 0.009 |
| Isobutane | 0.024 |
| n-Butenes | 0.006 |
| Isobutene | 0.014 |
| Carbon dioxide | 0.074 |
| Ethene | 0.001 |
| Tetradecane | approx. remainder up to 100% by weight |

Before the absorbate was conducted to the top of the downstream desorption column, it was heated to from 36 to 37° C. in an indirect heat exchanger. The heat carrier used was the liquid effluent from the desorption column which had a temperature of 37° C.

Subsequently, the absorbate (this may be performed, for example, in an inverse pump or by means of a valve) was decompressed to a pressure of from 2.5 to 3 bar (the mechanical energy released in the case of the inverse pump is appropriately also used to recompress absorbent freed in the desorption column) and the biphasic mixture thus generated was conducted into the desorption column at the top.

Air was conducted at a pressure of 3 bar into the desorption column (internal diameter=80 mm, length=1.70 m, wall thickness=4 mm) from the bottom in countercurrent to the absorbate descending from the desorption column head (1340 l (STP)/h). The amount of absorbate introduced at the top was 35 l/h. The absorbent which was conducted out of the desorption column at the bottom and had been substantially freed of desorbed components was cooled by indirect heat exchange with absorbate, compressed to the pressure required in the absorption column, cooled to 30° C. by another indirect heat exchange (appropriately on the industrial scale with surface water) and then recycled to the top of the absorption column. As separating internals, the desorption column comprised structured sheet metal packings from Montz (Montz BSH-750, specific surface area 750 m$^2$/m$^3$). In order to retain absorbent, the gas stream conducted out of the desorption column (if appropriate through a mechanical droplet separator) was washed with water. In other words, it was conducted through a packing element from Montz (Montz BSH-750, specific surface area 750 m$^2$/m$^3$), to which water (70 l/h) was introduced in countercurrent at a temperature of 18° C. Below the packing was mounted a collecting tray (chimney tray), from which the aqueous phase could be conducted out. In a phase separator, separation was effected into an aqueous phase and into an organic phase. The very small amount of organic phase was combined with the absorbent stream recycled to the top of the absorption column. The aqueous phase was recooled and introduced back to the packing element supplemented with fresh water (in order to compensate for evaporation losses). The washing was effected attached to the desorption column.

From the wash section, the washed gas stream was conducted out via mechanical droplet separators (separated liquid phase is recycled into the wash) with the following contents (when the dehydrogenation conversion in reaction zone A is selected at a higher value, the subsequent propene content may also be from 8 to 12% by volume; for example, the washed gas stream may also have 15% by volume of propane, 10% by volume of propene and 14.5% by volume of $O_2$):

|  | % by vol. |
|---|---|
| Nitrogen | 48.11 |
| Oxygen | 12.20 |
| Propane | 30.53 |
| Propene | 6.68 |
| Ethane | 0.09 |
| n-Butane | 0.08 |
| Isobutane | 0.21 |
| n-Butenes | 0.05 |
| Isobutene | 0.13 |
| Hydrogen | 0.04 |
| Carbon monoxide | 0.00 |
| Carbon dioxide | 0.85 |
| Water | 1.00 |
| Ethene | 0.02 |

The temperature of the gas mixture was increased to 250° C. by indirect heat exchange and the gas mixture with the aforementioned composition was conducted in an amount of 2260 l (STP)/l·h and an inlet pressure of 2.1 bar as a new starting reaction gas mixture into the downstream partial oxidation apparatus.

C) Configuration of Reaction Zone B (the Partial Oxidation Stage)

1. First Fixed Bed Reactor for the Step of Partial Oxidation of the Propene (Propylene) to Acrolein

| | |
|---|---|
| Heat exchange medium used: | salt melt consisting of 53% by weight of potassium nitrate, 40% by weight of sodium nitrite and 7% by weight of sodium nitrate. |
| Dimension of the catalyst tube: | total length 4200 mm, internal diameter 26 mm, external diameter 30 mm, wall thickness 2 mm. |
| Reactor: | Consists of a jacketed cylinder made of stainless steel (cylindrical guide tube surrounded by a cylindrical outer vessel). The wall thicknesses were universally from 2 to 5 mm. The internal diameter of the outer cylinder was 168 mm. The internal diameter of the guide tube was approx. 60 mm. At the top and bottom, the jacketed cylinder was completed by a lid and bottom respectively. The catalyst tube was mounted, conducted through the cylindrical guide tube, in the cylindrical vessel such that it projected at the top and bottom end thereof (with sealing) through the lid and bottom respectively in each case by 250 mm. The heat exchange medium was enclosed in the cylindrical vessel. In order to ensure very uniform thermal boundary conditions at the outer wall of the catalyst tube over the entire catalyst tube length within the cylindrical vessel (3700 mm), the heat exchange medium was circulated by sparging nitrogen in the cylindrical vessel. By means of the rising nitrogen, the heat exchange medium was conveyed from bottom to top in the cylindrical guide tube in order then to flow back downward in the intermediate space between cylindrical guide tube and cylindrical outer vessel (circulation of equal goodness can also be achieved by pumped circulation (for example propeller pumps)). Electrical heating mounted on the outer jacket controlled the temperature of the heat exchange medium to the desired level. Otherwise, there was air cooling. |
| Reactor charge: | Viewed over the reactor, salt melt and reaction gas mixture were conducted in countercurrent. The reaction gas mixture entered the reactor at the top. It was conducted into each reaction tube at a temperature of 250° C. |

| | |
|---|---|
| | The salt melt entered the cylindrical guide tube at the bottom at a temperature $T^{in}$ = 320° C. and left the cylindrical guide tube at a temperature $T^{out}$. The difference between $T^{in}$ and $T^{out}$ was about 2° C.<br>$T^{average}$ = ($T^{in}$ + $T^{out}$)/2. |
| Catalyst tube charge: (from top to bottom) | Section A: length 50 cm<br>Preliminary bed of steatite rings (steatite C 220 from CeramTec) of geometry 7 mm × 7 mm × 4 mm (external diameter × length × internal diameter).<br>Section B: length 100 cm<br>Catalyst tube charge with a homogeneous mixture of 30% by weight of steatite rings (steatite C 220 from CeramTec) of geometry 5 mm × 3 mm × 2 mm (external diameter × length × internal diameter) and 70% by weight of unsupported catalyst from Section C.<br>Section C: length 170 cm<br>Catalyst charge of annular (5 mm × 3 mm × 2 mm = external diameter × length × internal diameter) unsupported catalyst according to Example 1 of DE-A 10046957.<br>Section D: length 50 cm<br>Downstream bed of steatite rings (steatite C 220 from CeramTec) of geometry 7 mm × 7 mm × 4 mm (external diameter × length × internal diameter). |

2. Intermediate Cooling and Intermediate Oxygen Feeding

The product gas mixture leaving the first fixed bed reactor was conducted for the purpose of intermediate cooling (indirectly by means of air) through a connecting tube (length=400 mm, internal diameter=26 mm, wall thickness=2 mm, material=stainless steel) which, mounted centrally for a length of 200 mm, was charged with an inert bed of steatite spheres (Steatite from CeramTec) of diameter from 5 to 6 mm and flanged directly onto the catalyst tube of the first fixed bed reactor.

The gas mixture entered the connecting tube at a temperature of more than 310° C. and left it at a temperature of about 140° C. Subsequently, 290 l (STP)/h of compressed air as an oxygen source were mixed with the gas mixture.

The resulting charge gas mixture mixed on a static mixer was fed at a temperature of 220° C. to the fixed bed reactor for the step of partial oxidation of acrolein to acrylic acid.

3. Second Fixed Bed Reactor for the Step of Partial Oxidation of Acrolein to Acrylic Acid A fixed bed reactor was used which was of identical design to that for the first step. Salt melt and reaction gas mixture were conducted in cocurrent viewed over the reactor. The salt melt entered at the bottom, the reaction gas mixture likewise.

The catalyst tube charge (from bottom to top) was:

Section A: length 20 cm
Preliminary bed of steatite rings (steatite C 220 from CeramTec) of geometry 7 mm×7 mm×4 mm (external diameter×length×internal diameter).
Section B: length 100 cm
Catalyst charge of a homogeneous mixture of 30% by weight of steatite rings (steatite C 220 from CeramTec) of geometry 7 mm×3 mm×4 mm (external diameter×length×internal diameter) and 70% by weight of coated catalyst from Section C.
Section C: length 200 cm
Catalyst charge of annular (7 mm×3 mm×4 mm=external diameter×length×internal diameter) coated catalyst according to Preparation Example 5 of DE-A 10046928 (at this point, it is also possible to use analogous coated catalysts and those prepared in a corresponding manner, but whose active composition has a stoichiometry of $Mo_{12}V_{2.8}W_{1.2}Cu_{2.4}O_x$ or $Mo_{12}V_{3.5}W_{1.3}Cu_{2.4}O_x$).
Section D: length 50 cm
Downstream bed of steatite rings (steatite C 220 from CeramTec) of geometry 7 mm×7 mm×4 mm (external diameter×length×internal diameter).

The second reactor was charged with approx. 3850 g/h of charge gas mixture. $T^{average}$ is as defined for the first fixed bed reactor and was 274° C.

The propene conversion in the first reactor was 97.7 mol % and the acrolein conversion in the second reactor was 99.4 mol %.

The contents of the product gas mixture leaving the second fixed bed reactor at a temperature of 283° C. and a pressure of 1.8 bar (product gas mixture B) were:

| | % by vol. |
|---|---|
| Nitrogen | 52.87 |
| Oxygen | 3.03 |
| Propane | 27.48 |
| Propene | 0.14 |
| Methane | 0 |
| Ethane | 0.07 |
| n-Butane | 0.08 |
| Isobutane | 0.34 |
| n-Butenes | 0 |
| Isobutene | 0 |
| 1,3-Butadiene | 0 |
| Hydrogen | 0.03 |
| Carbon monoxide | 0.42 |
| Carbon dioxide | 1.85 |
| Water | 7.92 |
| Acrolein | 0.03 |
| Acrylic acid | 5.3 |
| Acetic acid | 0.18 |
| Formic acid | 0.01 |
| Formaldehyde | 0.17 |
| Benzaldehyde | 0 |
| Maleic anhydride | 0.04 |
| Ethene | 0.02 |

The catalysts used in the two reaction stages may also be replaced by the catalysts used in the examples of DE-A 10351269. The catalyst of the first reaction stage may also be replaced by the catalysts of the examples and comparative examples of DE-A 10344149. The catalyst of the second reaction stage may also be replaced by the catalysts of the examples of DE-A 10360057 and DE-A 10360058.

D) Configuration of Separation Zone B (Removal of the Acrylic Acid Target Product from the Product Gas Mixture of the Partial Oxidation)

In a direct cooler, the hot product gas mixture (product gas mixture B) was cooled to approx. 180° C. by spraying in a quench liquid (containing 57.4% by weight of diphenyl ether, 20.7% by weight of diphenyl and 20% by weight of o-dimethyl phthalate) of temperature from 140 to 150° C. which was also used as the absorbent. In the lower section of the direct cooler, the quench liquid was collected, withdrawn and resprayed into the upper section of the quench vessel via a heat exchanger in which it was recooled. The product gas mixture was fed to the direct cooler immersed into the collected quench liquid. The cooled product gas mixture then flowed into the downstream absorption column. In the quench circuit, high-boiling by-products accumulated and had to be discharged. From the quench circuit, a portion of 1 kg of quench liquid was therefore discharged discontinuously once per day into a vessel which was worked up discontinuously with the aid of a rotary evaporator. The purified absorbent was conducted back into the quench circuit and the losses of absorbent were supplemented with a mixture of diphenyl ether, diphenyl and o-dimethyl phthalate.

The cooled product gas mixture was conducted into the absorption column above the bottom. The absorption column was 5200 mm long, had an internal diameter of 50 mm and contained Kuehni (Switzerland) Rombopak 9M packings. The absorption column was manufactured from glass and, for reasons of heating, had a segmented glass jacket. Above the first packing, viewed from below, was installed a pressure decoupling valve (adjustable throttle), with the aid of which a pressure drop over the absorption column (as would occur on the industrial scale) of 100 to 300 mbar was simulated. The absorption column was operated at a top pressure of 1.35 bar. The glass jacket was divided into five separate segments, which were used to impose the desired temperature profile.

From bottom to top, the segments had the following temperatures (thermostatting by means of water pumped by circulation):

1st segment, length 1020 mm, 90-115° C.;
2nd segment, length 1250 mm, 88° C.;
3rd segment, length 950 mm, approx. 60° C.;
4th segment, length 950 mm, 50-55° C.;
5th segment, length 1250 mm, 18° C.

Below the uppermost packing was a collecting tray from which water-rich condensate (acid water) was drawn off. It was cooled to 20° C. using a heat exchanger and recycled into the absorption column via the uppermost packing, and the excess amount (the water of reaction) was discharged under level control. The amount of acid water discharged was fed to a phase separator. The organic phase was recycled into the absorption column via the second packing; the aqueous phase was disposed of. Immediately below the collecting tray, 3.5 l/h of absorption liquid were introduced at a temperature of 40° C.

The (main) residual gas discharged at the top of the absorption column (T=18° C., P=1.35 bar) had the following contents:

|  | % by vol. |
| --- | --- |
| Nitrogen | 61.17 |
| Oxygen | 3.51 |
| Propane | 31.80 |
| Propene | 0.16 |
| Methane | 0 |
| Ethane | 0.09 |
| n-Butane | 0.09 |
| Isobutane | 0.39 |
| n-Butenes | 0 |
| Isobutene | 0 |
| Butadienes | 0 |
| Hydrogen | 0.04 |
| Carbon monoxide | 0.49 |
| Carbon dioxide | 2.12 |
| Water | 0.09 |
| Acrolein | 0.03 |
| Acrylic acid | 0 |
| Formic acid | 0 |
| Formaldehyde | 0 |
| Benzaldehyde | 0 |
| Maleic anhydride | 0 |
| Ethene | 0.02 |

Indirect heat exchange heated the (main) residual gas to 40° C. (in order to rule out undesired condensation) which was compressed to 2.75 bar by means of a KNF Neuberger PM 17739-1200 compressor (on the industrial scale, a turbocompressor driven by an electrical motor, for example of the 12 MH4B type from Mannesmann DEMAG, Germany) and recycled as the cycle gas fraction (as the first fraction of the (overall) residual gas) into reaction zone A to charge the first dehydrogenation reactor.

From the bottom of the absorption column, 3.9 l/h of bottom liquid were drawn off under level control. A second, smaller stream of approx. 0.5 l/h was recycled into the direct cooler for the hot product gas mixture.

The bottom effluent (which may initially also be subjected to a stripping, as described in DE-A 10336386, with a portion of residual gas (preferably washed beforehand to substantially free it of acrylic acid); the laden stripping gas may then be recycled into the absorption column as described in DE-A 10336386) was conducted to the top of a stripping column (internal diameter 50 mm, length 2000 mm, made of glass, jacket for the purpose of heating (150° C.), 20 sieve trays (hole diameter 6.5 mm, triangular pitch). All low boilers (especially propane and propene), the majority of the acrylic acid, medium boilers (for example acetic acid) and a portion of the absorbent evaporated off there at about 200 mbar and 150° C. From the bottom of the stripping column, a circulation stream (200 l/h) was withdrawn by means of a pump (hermetic, 500 l/h) and recycled into the stripping column (at 190° C.) via a heat exchanger (forced-circulation flash evaporator). The stream of solvent which was descending at the bottom and had a low degree of loading went back to the acrylic acid absorption column and was fed back below the collecting tray at which the water of reaction (acid water) was discharged.

The vapors leaving the stripping column were conducted into a column free of internals in order to allow them to ascend in their condensate. The latter was withdrawn from the bottom of this column in an amount of 100 l/h, conducted through a heat exchanger in which the heat of condensation was removed and subsequently recycled at a temperature of 20° C. at the top of this column.

From the bottom of this column, 600 ml/h were also withdrawn (contains the acrylic acid target product, water and also residual absorbent), from which the acrylic acid can be removed in a manner known per se if required. At the top of the column free of internals, an acid water quench was again attached and was separated from the column by a collecting tray. The condensate drawn off at the collecting tray was mixed with the acid water withdrawn from the absorption column (for the product gas stream of the partial oxidation) and recycled into the acid water quench cooled to 18° C. Excess acid water was discharged. The gas leaving the acid water quench was recycled as a further residual gas comprising propane and unconverted propylene, after compression, into reaction zone A as a further cycle gas fraction (second fraction of the (overall) residual gas) to charge the first dehydrogenation reactor.

Comparative Example 2

The procedure of Experimental Example 1 was repeated. However, the product gas mixture A leaving the third dehydrogenation reactor was divided by a flow divider into two halves of identical composition and one half was recycled into separation zone A and the other half into reaction zone A as a constituent of the starting reaction gas mixture of the first dehydrogenation reactor.

To this end, the (overall) residual gas was compressed to a pressure of 4 bar and a jet pump was operated with the thus compressed (overall) residual gas as a driving jet, and the conveying direction of the driving jet decompressed to 3 bar through a driving nozzle via a mixing zone and a diffuser pointed into the evaporator upstream of the first heater, and the sucking nozzle pointed in the direction of one half of the product mixture A flow and the "sucking nozzle—mixing zone—diffuser" connection was the sole connection between the half of product mixture A to be recycled and the evaporator upstream of the first heater.

As early as after a continuous operating time of 10 h, the dehydrogenation catalysts started to lose activity.

Comparative example 3 (all pressures, as always in this document, are absolute pressures unless explicitly mentioned otherwise)

A) Configuration of Reaction Zone A (of the Dehydrogenation Stage)

The dehydrogenation stage consisted of three identical tubular reactors which were connected in series and charged in an identical manner with dehydrogenation catalyst.

The individual tubular reactor was a steel tube (stainless steel of DIN materials no. 1.4841) of length 1300 mm, wall thickness 3.6 mm and internal diameter 53.1 mm. The tubular reactors were each flowed through by the reaction gas mixture from top to bottom.

At the lower end of each tubular reactor was disposed a support grating made of the same stainless steel. On the support grating was disposed, from bottom to top, the following charge:

| | |
|---|---|
| 175 mm | bed length of steatite spheres (diameter 4-5 mm) of Steatite C-220 from CeramTec; |
| 21 mm | bed length of steatite spheres (diameter 1.5-2.5 mm) of Steatite C-220 from CeramTec; |
| 210 mm | bed length of dehydrogenation catalyst (Pt/Sn alloy which had been promoted with the elements Cs, K and La in oxidic form and which had been applied to the outer and inner surfaces of $ZrO_2 \cdot SiO_2$ mixed oxide support extrudates (average length (having a Gaussian distribution in the range from 3 mm to 12 mm with a maximum at approx. 6 mm): 6 mm, diameter: 2 mm) in the elemental stoichiometry (mass ratios including |

| | |
|---|---|
| | support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 10 219 879). |
| 21 mm | bed length of steatite spheres (diameter 1.5-2.5 mm) of Steatite C-220 from CeramTec; and |
| | finally, the remaining length of the tubular reactor, again a bed of steatite spheres (diameter 4-5 mm) of Steatite C-220 from CeramTec. |

The exterior of each of the tubular reactors was inserted, for the purposes of a preheating zone, for the first 500 mm of tube length from top to bottom (toward the support grating) into two half-shells made of copper (coating thickness=200 mm) which ensure uniform distribution of the amount of heat supplied and were electrically heated by means of a heating sleeve (from Horst, Heidelberg, Germany, length 500 mm, internal diameter 100 mm) which fully surrounded them.

From bottom to top, each of the tubular reactors, for the purposes of an adiabatic zone, was inserted for a length of 600 mm into in each case two pairs of thermally insulating half-shells (thickness of one half-shell=25 mm) made of MPS-Super G from Microtherm in Germany, which were mounted one on top of the other offset by 90° from one another. The insulating half-shells were in turn surrounded by a cylindrical envelope made of stainless steel (external diameter=173 mm, internal diameter=167 mm), to which was applied, for the purpose of trace heating, a heating sleeve (length=675 mm, internal diameter=173 mm) from Horst, Heidelberg, Germany. In this manner, it was possible in the adiabatic zone to minimize the heat flux from the environment into the reaction tube and out of the reaction tube into the environment.

Into each reaction tube was additionally inserted centrally a 1370 mm-long thermowell (external diameter: 6 mm, internal diameter: 4 mm), into which a multithermoelement (a total of 10 measurement points every 4 cm from the lower end of the reactor upward, thickness 3.2 mm) had been inserted.

Upstream of each individual tubular reactor was connected a steel tube, filled with steatite rings (made of steatite C-220 from CeramTec and of geometry 7 mm×3 mm×3 mm=external diameter×internal diameter×height), of length 1300 mm as a heater. In this tube, the reaction gas mixture was in each case preheated to the entrance temperature of the downstream tubular reactor and simultaneously mixed in an ideal manner. For this purpose, the heater tubes (stainless steel of DIN materials no. 1.4841, wall thickness 3.6 mm, internal diameter 53.1 mm) were electrically heated along the central 1200 mm length of the tube by means of heating sleeves from Horst, Heidelberg, Germany applied to them. The connection between heaters and tubular reactors was brought about by stainless steel tubes (stainless steel of DIN materials no. 1.4841, external diameter 21.3 mm, internal diameter 16.1 mm, length approx. 700 mm) thermally insulated with customary heat insulation materials.

Upstream of the inlet of the reaction gas mixture into the particular heater was mounted a feed tap, through which compressed air could in each case be supplied to the reaction gas mixture. The steady state is described hereinbelow.

To the first dehydrogenation reactor was fed a starting reaction gas mixture composed of 300 g/h of crude propane (first feed stream comprising propane), 375 g/h of water and 3768 g/h of (overall) residual gas as cycle gas (second feed stream comprising propane) at a temperature of 400° C. and an absolute pressure of 2.6 bar (on the industrial scale, the inlet pressure was appropriately selected approx. 0.5 bar higher, in order to take account of the increased pressure drop in reaction zone A (caused by higher flow rates)).

The crude propane comprised:

|  | % by vol. |
|---|---|
| Methane | 0 |
| Ethane | 0.156 |
| Ethene | 0 |
| Propane | 96.18 |
| Propene (propylene) | 0.002 |
| $H_2$ | 0 |
| $O_2$ | 0 |
| $N_2$ | 1.70 |
| CO | 0 |
| $CO_2$ | 0 |
| Isobutane | 1.245 |
| n-Butane | 0.711 |
| trans-Butene | 0.0005 |
| Isobutene | 0 |
| cis-Butene | 0.0015 |
| 1-Butene | 0.0048 |
| Butadiene | 0 |

The (overall) residual gas (cycle gas) comprised:

|  | % by vol. |
|---|---|
| Methane | 0.009 |
| Ethane | 0.088 |
| Ethene | 0.038 |
| Propane | 29.56 |
| Propene | 0.122 |
| $H_2$ | 0.050 |
| $O_2$ | 3.35 |
| $N_2$ | 64.05 |
| CO | 0.538 |
| $CO_2$ | 1.85 |
| Isobutane | 0.234 |
| n-Butane | 0.098 |
| trans-Butene | 0.00005 |
| Isobutene | 0.00051 |
| cis-Butene | 0.00144 |
| 1-Butene | 0.00048 |
| Butadiene | 0.0087 |

The composition of the crude propane and all other gas compositions were determined by gas chromatography [HP 6890 with Chem-Station, detectors: FID, TCD, separating columns: $Al_2O_3$/KCL (Chrompak), Carboxen 1010 (Supelco)]. In the case of gas mixtures comprising steam, the steam was condensed out in a water separator by cooling and, if appropriate, decompression before the gas chromatography analysis. The uncondensed residual gas was analyzed and all data relate to this gas on a dry basis (i.e. the amount of steam present in the gas mixture which was actually to be analyzed was not taken into account).

The starting reaction gas mixture was generated in an evaporator which was connected upstream of the first heater. The evaporator itself was likewise designed as a heater. To it were fed 300 g/h of gaseous crude propane (65° C., 5 bar), 3768 g/h of (overall) residual gas (cycle gas) (50° C., 2.8 bar) and 375 g/h of water (20° C., 3 bar). The heating of the evaporator was controlled to a gas mixture outlet temperature of 200° C. The evaporator was connected to the first heater in a manner corresponding to that in which the reactors were connected to the heaters.

The heating of the first heater was controlled in such a way that the gas mixture passed from the evaporator into the first heater left the first heater at a temperature of 400° C. (the wall temperature required for this purpose was approx. 440° C.). The starting reaction gas mixture was then conducted into the first tubular reactor and heated further in the preheating zone thereof to a reaction zone inlet temperature of 460° C.

When it passed through the first tubular reactor, the temperature of the reaction gas mixture passed through a maximum (known as hotspot temperature) of 549.1° C. (the quantitative data reported here relate to the operating state after 200 operating hours; in the further course of operation, the different temperatures were adjusted such that the conversion based on single pass and the space-time yield remained substantially constant; the corresponding procedure was also used in the first 200 operating hours), which migrated in flow direction in the course of the continuous operation of the experimental plant owing to gradual catalyst deactivation (the migration rate was approx. 0.03 mm/h).

The reaction gas mixture leaving the first dehydrogenation reactor had the following contents:

|  | % by vol. |
|---|---|
| Methane | 0.045 |
| Ethane | 0.109 |
| Ethene | 0.042 |
| Propane | 30.3 |
| Propene | 2.88 |
| $H_2$ | 5.00 |
| $O_2$ | 0 |
| $N_2$ | 59.13 |
| CO | 0.06 |
| $CO_2$ | 3.24 |
| Isobutane | 0.257 |
| n-Butane | 0.116 |
| trans-Butene | 0.05 |
| Isobutene | 0.001 |
| cis-Butene | 0.004 |
| 1-Butene | 0.001 |
| Butadiene | 0.003 |

Its temperature was 509° C. and its pressure was approx. 2.56 bar.

Before it entered the downstream heater, 80 l (STP)/h of compressed air were metered to the reaction gas mixture (23° C., 4.2 bar).

The reaction gas mixture was then heated to 465° C. (2nd reaction zone inlet) by means of the electrical heating means of the heater (wall temperature approx. 540° C.) and the preheating zone of the downstream (second) reaction tube (wall temperature approx. 560° C.). The pressure of the reaction gas mixture at this point was 2.56 bar.

When it passed through the second tubular reactor, the temperature of the reaction gas mixture passed through a maximum of approx. 560° C. which migrated in flow direction in the course of the continuous operation of the experimental plant owing to gradual catalyst deactivation (the migration rate was approx. 0.1 mm/h). The reaction gas mixture leaving the second dehydrogenation reactor had the following contents:

| | % by vol. |
|---|---|
| Methane | 0.078 |
| Ethane | 0.144 |
| Ethene | 0.063 |
| Propane | 26.6 |
| Propene | 4.94 |
| $H_2$ | 6.43 |
| $O_2$ | 0 |
| $N_2$ | 58.58 |
| CO | 0.384 |
| $CO_2$ | 3.58 |
| Isobutane | 0.22 |
| n-Butane | 0.094 |
| trans-Butene | 0.063 |
| Isobutene | 0.001 |
| cis-Butene | 0.01 |
| 1-Butene | 0 |
| Butadiene | 0.004 |

Its temperature was approx. 493° C. and its pressure was approx. 2.52 bar.

Before it entered the downstream heater, 98 l (STP)/h of compressed air were metered to the reaction gas mixture (23° C., 4.2 bar).

The reaction gas mixture was then heated to 521° C. (3rd reaction zone inlet) by means of the electrical heating means of the heater (wall temperature approx. 540° C.) and the preheating zone of the downstream (third) reaction tube (wall temperature approx. 540° C.). The pressure of the reaction gas mixture at this point was 2.52 bar.

When it passed through the third tubular reactor, the temperature of the reaction gas mixture passed through a maximum of 570° C. which migrated in flow direction in the course of the continuous operation of the experimental plant owing to gradual catalyst deactivation (the migration rate was approx. 0.1 mm/h). The reaction gas mixture leaving the third dehydrogenation reactor had the following contents:

| | % by vol. |
|---|---|
| Methane | 0.1046 |
| Ethane | 0.144 |
| Ethene | 0.0743 |
| Propane | 25.22 |
| Propene | 5.51 |
| $H_2$ | 4.69 |
| $O_2$ | 0 |
| $N_2$ | 60.10 |
| CO | 0.237 |
| $CO_2$ | 3.54 |
| Isobutane | 0.201 |
| n-Butane | 0.085 |
| trans-Butene | 0.070 |
| Isobutene | 0.0013 |
| cis-Butene | 0.011 |
| 1-Butene | 0.0004 |
| Butadiene | 0.0056 |

Its temperature was 480.4° C. and its pressure was 2.48 bar.

This resulted in an overall dehydrogenation conversion of the propane over the dehydrogenation stage based on single pass of the starting reaction gas mixture, of 19.91 mol %.

In the event of advanced deactivation of the dehydrogenation catalyst beds, the process was interrupted and they were regenerated as described in DE-A 10028582. This was essentially always the case when the hotspot temperature in all three tubular reactors was approx. 580° C.

Surprisingly, the deactivation of the dehydrogenation catalyst beds progressed more slowly at elevated working pressure.

E) Configuration of Separation Zone A

Direct cooling with sprayed cooled water (T=20° C.) cooled the product gas mixture leaving the third dehydrogenation reactor (product gas mixture A) to 40° C. in a direct cooler (quench) in cocurrent (the remaining gaseous mixture was conducted out of the water quench in the opposite direction to the product gas inflow direction). About 75% by weight of the steam present in the product gas mixture (steam was added to the starting reaction gas mixture of reaction zone A and formed in the dehydrogenation stage as a result of combustion of hydrogen and also possibly hydrocarbon with atmospheric oxygen; the heat of combustion substantially maintained the reaction temperature in the reaction gas mixture in reaction zone A) condensed out in the course of direct cooling. The condensate which formed was conducted out of the water quench by means of level control and sent to its disposal. Otherwise, the water used for direct cooling was circulated (by pumping), recooled by indirect heat exchange and sprayed again for the purpose of direct cooling.

Instead of the direct cooling with water described, the product gas mixture from the dehydrogenation stage may also initially be cooled by heating the starting reaction gas mixture to be fed to the dehydrogenation stage (for example to a temperature in the range from 350 to 450° C.) with the product gas mixture in an indirect heat exchanger (for example in a tube bundle heat exchanger in cocurrent or in countercurrent). This cools the product gas mixture of the dehydrogenation stage to an appropriate degree from the high exit temperature of the dehydrogenation stage (for example from 450 to 550° C.) to from approx. 200 to 300° C.

A further cooling of the product gas mixture of the dehydrogenation stage can be effected by using it in an indirect heat exchanger for the purpose of heating the starting gas mixture for the partial oxidation, still to be described hereinbelow, of the propene generated in the dehydrogenation stage, and/or by using it for the purpose of balancing the absorber offgas cooling, still to be described below, in the preferably two-stage expansion thereof by means of expansion turbines, or for the purpose of compensating for it by advance incipient heating.

Afterward, the product gas mixture is at a temperature of about 180° C. Subsequently, it is possible to cool it to a temperature in the range from 30° C. to 60° C. by means of air and/or surface water coolers.

Droplet separators integrated into the coolers or connected downstream thereof collect the water which has condensed out in the course of cooling and feed it to disposal under level control.

The thus cooled and steam-deburdened product gas mixture of the dehydrogenation stage, having a pressure of about 2 bar, was subsequently compressed to a pressure of from 10 to 13 bar.

In an appropriate manner from an application point of view, the compression was carried out in two stages in order to avoid excessively high compression temperatures (this purpose was also served by the cooling carried out in advance; the steam separation additionally deburdens the compressor output to be expended). In the first stage, compression was effected to a pressure of from 4 to 4.5 bar. The outlet temperature of the gas mixture on leaving the compressor was about 115° C.

In a downstream indirect heat exchanger (air cooler or surface water cooler), the gas mixture was cooled again to from 40 to 60° C., in the course of which further steam condensed. Droplet separators collected the condensate and discharged it under level control.

In the second compressor stage, compression was effected starting from a pressure of about 4 bar to an end pressure of 10 bar (here, it is also possible if appropriate to condense to a pressure of up to 13 bar and more). The outlet temperature on leaving the compressor was about 126° C.

In two further downstream indirect heat exchangers (initially an air cooler (is normally a tube bundle heat exchanger; the gas to be cooled appropriately flows through the tube interior) and then a surface water cooler), the compressed gas mixture was cooled initially to from 40 to 60° C. and then to 30° C. Water which condensed out was again separated by means of droplet separators and conducted out. When it leaves the second compressor, the gas mixture only comprises approximately 0.2% by weight of water. The low water content reduces the occurrence of water and thus prevents operation problems, caused by biphasicity of the liquid, in the downstream absorption, and the high pressure reduces the amount of absorbent required for the purpose of absorption.

While turbocompressors (non-oil-lubricated, dry-running, contactless compressors) are used on the industrial scale for the purpose of compression (for example of the 12 MH 4B type from Mannesmann DEMAG, Germany), MV 3459 II membrane compressors from Sera were used here. In principle, the compressors may be driven either by electrical motors or by vapor or gas turbines. Frequently, driving by vapor turbines is the most economic. The gas mixture, cooled and compressed as described, was fed to an absorption column directly above the bottom (approx. 4650 g/h). It had the following contents:

|  | % by vol. |
| --- | --- |
| Nitrogen | 61.22 |
| Oxygen | 0.25 |
| Propane | 24.23 |
| Propene | 5.07 |
| Methane | 0.02 |
| Ethane | 0.11 |
| Ethene | 0.03 |
| n-Butane | 0.06 |
| Isobutane | 0.09 |
| n-Butenes | 0.04 |
| Isobutene | 0.10 |
| 1,3-Butadiene | 0.00 |
| Hydrogen | 5.57 |
| Carbon monoxide | 0.05 |
| Carbon dioxide | 3.15 |

The absorption column consisted of 1.4571 stainless steel. The column internal diameter was 80 mm, the wall thickness 4 mm and the column length 1.70 m.

About 70% of the volume of the absorption column was filled with Montz packing elements (Montz BSH-750, specific surface area 750 m$^2$/m$^3$) as separating internals. The packing elements were directly adjacent to one another and began at the height of 1/5 of the column length from below. The absorption column was neither cooled nor heated externally. At the top of the column, technical-grade tetradecane from Haltermann, Germany, of the PKWF 4/7 af type was introduced at an introduction temperature of 30° C. as an absorbent (gas chromatography analysis by means of FID detection gave the following GC area % composition at the start (fresh):

n-Tridecane 7.6%,
n-Tetradecane 47.3%,
n-Pentadecane 7.0%,
n-Hexadecane 3.2%,
n-Heptadecane 14.1% and
residual sum 20.7%;

this composition changed in the course (after approx. 3000 h$^{-1}$) of continuous process operation to the following values:

n-Tridecane 2.6%,
n-Tetradecane 39.5%,
n-Pentadecane 9.4%,
n-Hexadecane 4.8%,
n-Heptadecane 23.4% and
residual sum 20.3%).

The trickle density was 15 m$^3$ of absorbent per m$^2$ of free cross-sectional area and hour (=28 kg/h of tetradecane).

The offgas stream conducted out of the absorption column to incineration still comprised 950 ppm by volume of propane and 250 ppm by volume of propene. On the industrial scale, this offgas stream is conducted via an expander (for example an expansion turbine) into the combustion, in order to recover the majority of the compression output expended in the two-stage compression and to recycle it into the two-stage compression. Appropriately, the expansion is also carried out in two stages in order to prevent undesired condensation. The mechanical energy obtained in the decompression may be utilized either directly as a secondary or main drive for one of the compressors and/or to generate electricity.

Before the decompressed absorber offgas is conducted to the combustion, it may be appropriate on the industrial scale to remove the hydrogen present therein. This may be effected, for example, by passing the offgas through a membrane, generally shaped to a tube, which is permeable only to the molecular hydrogen. The thus removed molecular hydrogen may be recycled, for example, into the heterogeneously catalyzed dehydrogenation or fed to another utilization (for example in fuel cells).

In principle, the hydrogen removal may also be undertaken by partial condensation, adsorption and/or rectification (preferably under pressure). On the industrial scale, it is additionally generally appropriate to conduct the absorber offgas through the acid water, yet to be described below, in order to concentrate it.

The absorbate comprised the following contents (% by weight based on the weight of the absorbate):

|  | % by weight |
| --- | --- |
| Nitrogen | 0.147 |
| Propane | 4.58 |
| Propene | 0.915 |
| Ethane | 0.07 |
| n-Butane | 0.015 |
| Isobutane | 0.023 |
| n-Butenes | 0.009 |
| Isobutene | 0.024 |
| Carbon dioxide | 0.086 |
| Ethene | 0.000 |
| Tetradecane | approx. remainder up to 100% by weight |

Before the absorbate was conducted to the top of the downstream desorption column, it was heated to 60° C. in an indirect heat exchanger.

Subsequently, the absorbate (this may be performed, for example, in an inverse pump or by means of a valve) was decompressed to a pressure of 2.7 bar (the mechanical energy released in the case of the inverse pump is appropriately also used to recompress absorbent freed in the desorption column) and the biphasic mixture thus generated was conducted into the desorption column at the top.

Air was conducted at a pressure of 3 bar into the desorption column (internal diameter=80 mm, length=1.70 m, wall thickness=4 mm) from the bottom in countercurrent to the absorbate descending from the desorption column head (1269 l (STP)/h). The amount of absorbate introduced at the top was 33.7 l/h. The absorbent which had been conducted out of the desorption column at the bottom and had been substantially freed of desorbed components was cooled by indirect heat exchange with absorbate, compressed to the pressure required in the absorption column, cooled to 16° C. by another indirect heat exchange (on the industrial scale appropriately with surface water) and then recycled to the top of the absorption column. As separating internals, the desorption column comprised structured sheet metal packings from Montz (Montz BSH-750, specific surface area 750 m²/m³). In order to retain absorbent, the gas stream conducted out of the desorption column (if appropriate through a mechanical droplet separator) was washed with water. In other words, it was conducted through a packing element from Montz (Montz BSH-750, specific surface area 750 m²/m³), to which water (70 l/h) was introduced in countercurrent at a temperature of 18° C. Below the packing was mounted a collecting tray (chimney tray), from which the aqueous phase could be conducted out. In a phase separator, separation was effected into an aqueous phase and into an organic phase. The very small amount of organic phase was combined with the absorbent stream recycled to the top of the absorption column. The aqueous phase was recooled and introduced back to the packing element supplemented with fresh water (in order to compensate for evaporation losses). The washing was effected attached to the desorption column.

From the wash section, the washed gas stream was conducted out through mechanical droplet separators (separated liquid phase is recycled into the wash) with the following contents (when the dehydrogenation conversion selected in reaction zone A is higher, the subsequent propene content may also be from 8 to 12% by volume; for example, the washed gas stream may also have 15% by volume of propane, 10% by volume of propene and 14.5% by volume of $O_2$):

|  | % by vol. |
|---|---|
| Nitrogen | 46.69 |
| Oxygen | 11.84 |
| Propane | 32.53 |
| Propene | 6.81 |
| Ethane | 0.07 |
| n-Butane | 0.08 |
| Isobutane | 0.12 |
| n-Butenes | 0.05 |
| Isobutene | 0.13 |
| Hydrogen | 0.07 |
| Carbon monoxide | 0.00 |
| Carbon dioxide | 0.61 |
| Water | 1.00 |
| Ethene | 0.00 |

The temperature of the gas mixture was increased to 250° C. by indirect heat exchange and the gas mixture with the aforementioned composition was conducted in an amount of 2128 l (STP)/l·h and an inlet pressure of 2.1 bar as a new starting reaction gas mixture into the downstream partial oxidation apparatus.

C) Configuration of Reaction Zone B (of the Partial Oxidation Stage)

1. First Fixed Bed Reactor for the Step of Partial Oxidation of Propene (Propylene) to Acrolein

| | |
|---|---|
| Heat exchange medium used: | salt melt consisting of 53% by weight of potassium nitrate, 40% by weight of sodium nitrite and 7% by weight of sodium nitrate. |
| Dimension of the catalyst tube: | total length 4200 mm, internal diameter 26 mm, external diameter 30 mm, wall thickness 2 mm. |
| Reactor: | Consisted of a jacketed cylinder made of stainless steel (cylindrical guide tube surrounded by a cylindrical outer vessel). The wall thicknesses were universally from 2 to 5 mm.<br>The internal diameter of the outer cylinder was 168 mm. The internal diameter of the guide tube was approx. 60 mm.<br>At the top and bottom, the jacketed cylinder was concluded by a lid and bottom respectively.<br>The catalyst tube was mounted, guided by the guide tube, in the cylindrical vessel such that it projected at the top and bottom end thereof (with sealing) through the lid and bottom respectively in each case by 250 mm.<br>The heat exchange medium was enclosed in the cylindrical vessel. In order to ensure very uniform thermal boundary conditions at the outer wall of the catalyst tube over the entire catalyst tube length within the cylindrical vessel (3700 mm), the heat exchange medium was circulated by sparging of nitrogen in the cylindrical vessel.<br>By means of the ascending nitrogen, the heat exchange medium was conveyed from bottom to top in the cylindrical guide tube in order then to flow back downward in the intermediate space between cylindrical guide tube and cylindrical outer vessel (circulation of equal goodness can also be |

-continued

| | |
|---|---|
| | achieved by pumped circulation (for example propeller pumps)). Electrical heating mounted on the outer jacket might control the temperature of the heat exchange medium to the desired level. Otherwise, there was air cooling. |
| Reactor charge: | Viewed over the reactor, salt melt and reaction gas mixture were conducted in countercurrent. The reaction gas mixture entered the reactor at the top. It was conducted into each reaction tube at a temperature of 250° C. The salt melt entered the cylindrical guide tube at the bottom at a temperature $T^{in}$ = 335° C. and left the cylindrical guide tube at the top at a temperature $T^{out}$. The difference between $T^{in}$ and $T^{out}$ was about 2° C. $T^{average}$ = ($T^{in}$ + $T^{out}$)/2. |
| Catalyst tube charge: (from top to bottom) | Section A: length 50 cm Preliminary bed of steatite rings (Steatite C 220 from CeramTec) of geometry 7 mm × 7 mm × 4 mm (external diameter × length × internal diameter). Section B: length 100 cm Catalyst tube charge with a homogeneous mixture of 30% by weight of steatite rings (Steatite C 220 from CeramTec) of geometry 5 mm × 3 mm × 2 mm (external diameter × length × internal diameter) and 70% by weight of unsupported catalyst from section C. Section C: length 170 cm Catalyst charge of annular (5 mm × 3 mm × 2 mm = external diameter × length × internal diameter) unsupported catalyst according to example 1 of DE-A 10046957. Section D: length 50 cm Downstream bed of steatite rings (steatite C 220 from CeramTec) of geometry 7 mm × 7 mm × 4 mm (external diameter × length × internal diameter). |

2. Intermediate Cooling and Intermediate Oxygen Feeding

The product gas mixture leaving the first fixed bed reactor was conducted for the purpose of intermediate cooling (indirectly by means of air) through a connecting tube (length=400 mm, internal diameter=26 mm, wall thickness=2 mm, material=stainless steel) which, mounted centrally for a length of 200 mm, was charged with an inert bed of steatite spheres (Steatite from CeramTec) of diameter from 5 to 6 mm and flanged directly onto the catalyst tube of the first fixed bed reactor.

The gas mixture entered the connecting tube at a temperature of more than 310° C. and left it at a temperature of about 140° C. Subsequently, 269 l (STP)/h of compressed air as an oxygen source were mixed with the gas mixture.

The resulting charge gas mixture mixed on a static mixer was fed at a temperature of 220° C. to the fixed bed reactor for the step of partial oxidation of acrolein to acrylic acid.

3. Second Fixed Bed Reactor for the Step of Partial Oxidation of Acrolein to Acrylic Acid A fixed bed reactor was used which was of identical design to that for the first step. Salt melt and reaction gas mixture were conducted in cocurrent viewed over the reactor. The salt melt entered at the bottom, the reaction gas mixture likewise.

The catalyst tube charge (from bottom to top) was:
Section A: length 20 cm
Preliminary bed of steatite rings (Steatite C 220 from CeramTec) of geometry 7 mm×7 mm×4 mm (external diameter×length×internal diameter).
Section B: length 100 cm
Catalyst charge of a homogeneous mixture of 30% by weight of steatite rings (Steatite C 220 from CeramTec) of geometry 7 mm×3 mm×4 mm (external diameter× length×internal diameter) and 70% by weight of coated catalyst from section C.
Section C: length 200 cm
Catalyst charge of annular (7 mm×3 mm×4 mm=external diameter×length×internal diameter) coated catalyst according to preparation example 5 of DE-A 10046928 (at this point, it is also possible to use analogous coated catalysts and those prepared in a corresponding manner, but whose active composition has a stoichiometry of $Mo_{12}V_{2.8}W_{1.2}Cu_{2.4}O_x$ or of $Mo_{12}V_{3.5}W_{1.3}Cu_{2.4}O_x$.
Section D: length 50 cm
Downstream bed of steatite rings (Steatite C 220 from CeramTec) of geometry 7 mm×7 mm×4 mm (external diameter×length×internal diameter).

The second reactor was charged with approx. 3607 g/h of charge gas mixture. $T^{average}$ is as defined for the first fixed bed reactor and was 284° C.

The propene conversion in the first reactor was 98.0 mol % and the acrolein conversion in the second reactor was approx. 99.8 mol %.

The contents of the product gas mixture leaving the second fixed bed reactor (product gas mixture B) at a temperature of 281° C. and a pressure of 1.8 bar were:

| | % by vol. |
|---|---|
| Nitrogen | 51.54 |
| Oxygen | 2.3 |
| Propane | 29.20 |
| Propene | 0.110 |
| Methane | 0 |
| Ethane | 0.077 |
| n-Butane | 0.101 |
| Isobutane | 0.236 |
| n-Butenes | 0 |
| Isobutene | 0.001 |
| 1,3-Butadiene | 0.009 |

-continued

|  | % by vol. |
|---|---|
| Hydrogen | 0.05 |
| Carbon monoxide | 0.596 |
| Carbon dioxide | 1.72 |
| Water | 8.21 |
| Acrolein | 0.009 |
| Acrylic acid | 5.28 |
| Acetic acid | 0.240 |
| Propionic acid | 0.002 |
| Formic acid | 0.019 |
| Formaldehyde | 0.198 |
| Benzaldehyde | 0.005 |
| Maleic anhydride | 0.047 |
| Methacrolein | 0.020 |
| Methacrylic acid | 0.011 |
| Ethene | 0.032 |

The catalysts used in the two reaction stages may also be replaced by the catalysts used in the examples of DE-A 10351269. The catalyst of the first reaction stage may also be replaced by the catalysts of the examples and comparative examples of DE-A 10344149. The catalyst of the second reaction stage may also be replaced by the catalysts of the examples of DE-A 10360057 and DE-A 10360058. In addition, the partial oxidation may be carried out as a high-load method, as described in DE-A 10313210, DE-A 10313213, DE-A 10313212, DE-A 10313211, DE-A 10313208, DE-A 10313209 and DE-A 10313214, and the prior art acknowledged in these documents.

D) Configuration of Separation Zone B (Removal of the Acrylic Acid Target Product from the Product Gas Mixture of the Partial Oxidation)

In a direct cooler, the hot product gas mixture stream (product gas mixture B) was cooled to approx. 180° C. in cocurrent (after combination with the laden stripping gas stream described below) by spraying in a quench liquid (comprising 57.4% by weight of diphenyl ether, 20.7% by weight of diphenyl, 20% by weight of dimethyl o-phthalate (DMP) and, as the remainder of up to 100% by weight, phenothiazine (up to 1% by weight) and high boilers (e.g. acrylic acid oligomers)) of temperature from 140 to 150° C., which was also used as the absorbent. In the lower section of the direct cooler, the unevaporated quench liquid was collected, withdrawn and, via a heat exchanger in which it was brought back to input temperature, resprayed into the upper section of the quench vessel. The product gas mixture stream B (combined with the laden stripping gas) and the quench liquid which has been sprayed to give jets were fed in parallel to the direct cooler. The cooled product gas mixture stream B then flowed into the downstream absorption column. In the quench circuit, high-boiling by-products then accumulated and had to be discharged. From the quench circuit, a portion of 1 kg of quench liquid was therefore discharged discontinuously once per day into a vessel which was worked up discontinuously with the aid of a rotary evaporator (8 mbar, 180° C.). The purified absorbent condensate obtained in this way was fed to the buffer vessel described below for the bottom effluent from the residual gas stainless steel pressure wash column, and the losses of absorbent of about 2.9 g/h which was suffered in the course of workup in the rotary evaporator were replaced once per week by addition of fresh mixture consisting of diphenyl ether (21.2% by weight), diphenyl (58.8% by weight) (both together=Diphyle®) and dimethyl o-phthalate (20% by weight) to the condensate.

The cooled product gas mixture B was conducted into the absorption column above the bottom and below the first packing element. The absorption column (without the bottom) wars 5420 mm long, had an internal diameter of 50 mm and contained Kuehni (CH) Rhombopak 9M packings for a total length of 3.3 m.

The absorption column was manufactured from glass and, for reasons of heating, had a segmented glass jacket. Immediately above the second packing element, viewed from below, was installed a pressure decoupling valve (an adjustable throttle), with the aid of which a pressure drop over the absorption column (as would occur on the industrial scale) of from 100 to 300 mbar could be simulated. The absorption column was operated at a top pressure of 1.30 bar and a bottom pressure of 1.40 bar. The bottom temperature was approx. 113° C. The glass jacket was divided into five successive, separately operated segments which were used to impose the temperature profile below on the absorption column. This segmentation was also followed by the inner structure of the absorption column.

The segments had, from bottom to top the following temperatures (they were each thermostatted by means of water pumped in circulation, or with heat carrier oil of corresponding temperature in the 1st segment) and were configured as follows:

| | |
|---|---|
| 1st segment: | length 1020 mm (upward starting from the feed point of product gas mixture B), 113° C., 0.4 m of Rhombopak between the feed point of product gas mixture B disposed directly above the bottom of the absorption column and the feed point of bottoms liquid which is continuously withdrawn from the column bottom and recirculated into the column (at approx. 113° C., in an amount of approx. 200 l/h) and 0.6 m of Rhombopak above this introduction point. The distance between the two Rhombopaks was approx. 2 cm. |
| 2nd segment: | length 1250 mm, 75° C., at the lower end was disposed the pressure decoupling valve and above the pressure decoupling valve up to the feed point of the low boiler condensate stream from the purifying distillation described below was disposed 0.5 m of Rhombopak. |
| 3rd segment: | length 950 mm, 60° C., 0.6 m of Rhombopak which begins directly above the low boiler condensate introduction point of the 2nd segment. |
| 4th segment: | length 950 mm, 50-55° C., 0.6 m of Rhombopak which ends directly below the introduction point of the main absorbent stream described below. |

-continued

5th segment: length 1250 mm, 20° C., 0.6 m of Rhombopak between the collecting tray mounted directly above the absorbent introduction in the 4th segment for the efflux of the acid water (described below) and the introduction point of recirculated acid water at the top of the absorption column.

From the aforementioned collecting tray disposed in the 5th segment, water-rich condensate (acid water) was drawn off continuously (approx. 70.2 l/h). It was cooled indirectly to 20° C. using a heat exchanger and recycled back into the absorption column predominantly above the uppermost Rhombopak packing (70 liters/h). The nonrecycled proportion of the acid water withdrawn (the reaction water) was discharged under level control and sent to an acid water extraction stage. In this stage, the discharged acid water was combined and mixed at ambient pressure with the smaller substream of the absorbent (described below) having a low loading (of acrylic acid and secondary components) in a stirred glass vessel kept at ambient temperature (volume 1 liter, diameter 80 mm). The resulting mixture was discharged continuously into a glass phase separation vessel (volume 7.5 liters, diameter 150 mm) likewise kept at ambient temperature by free overflow. There, the liquid mixture which had overflowed was separated into two liquid phases, short-chain acidic secondary components (for example acetic acid) being transferred preferentially into the aqueous phase having lower specific gravity and acrylic acid preferentially into the organic phase having higher specific gravity. The organic phase is combined with the larger substream of the absorbent having a low loading by means of a forced-conveyance membrane metering pump and this overall stream (approx. 3.0 l/h, 40° C.) was fed as already described directly below the acid water collecting tray as the main absorbent stream to the absorption column.

The (main) residual gas leaving the absorption column at the top (T=20° C., P=1.30 bar) had the following contents:

|  | % by volume |
| --- | --- |
| Nitrogen | 59.9 |
| Oxygen | 2.67 |
| Propane | 33.93 |
| Propene | 0.128 |
| Methane | 0 |
| Ethane | 0.09 |
| n-Butane | 0.118 |
| Isobutane | 0.274 |
| n-Butenes | 0 |
| Isobutene | 0.001 |
| Butadienes | 0.010 |
| Hydrogen | 0.058 |
| Carbon monoxide | 0.693 |
| Carbon dioxide | 1.97 |
| Acrolein | 0.009 |
| Ethene | 0.037 |
| All contents above are calculated without water |  |
| Water | 1.78 (based on all) |

The (main) residual gas was heated to 40° C. by indirect heat exchange (in order to rule out undesired condensation), compressed to 2.70 bar by means of a membrane compressor (on the industrial scale, a turbocompressor driven by means of electrical motor, for example of the 12 MH4B type from Mannesmann DEMAG, Germany) and about 78% by volume were recycled as cycle gas (total residual gas) into reaction zone A to charge the first dehydrogenation reactor.

About 22% by volume of the compressed (main) residual gas were branched off with decompression to 1.6 bar and washed in a stainless steel pressure wash column (material 1.4571, internal diameter 30 mm, charge: 2 m of Rhombopak 9M) in countercurrent at approx. 1.6 bar and approx. 51° C. with the total stream, described below, of absorbent having very low loading (the absorbent having very low loading was introduced at the top and the gas was conducted into the column at the bottom).

In a further stainless steel pressure column (material 1.4571, internal diameter 30 mm, charge: 3 m of Rhombopak 9M, jacket heated with oil=stripping column), this washed gas stream at approx. 1.5 bar and from approx. 119 to 125° C. was utilized in order to strip low-boiling components out of the laden absorbent stream which was drawn off continuously from the bottom of the absorption column (approx. 3.5 l/h, approx. 113° C.) (for example as described in DE-A 10336386). The resulting gas stream (laden stripping gas) laden with low boilers (more volatile than acrylic acid) was heated in a jacketed line (diameter 15 mm, outer jacket: corrugated stainless steel tube) heated at 170° C. and combined with the hot product gas mixture stream B at the inlet of the quench vessel.

At the lower end of the stainless steel pressure wash column, the absorbent stream with a low loading was discharged under level control into the buffer vessel already mentioned (glass, volume 5 liters) (the absorbent condensate obtained in the rotary evaporator is also passed into this vessel as already described).

From the buffer vessel, a larger substream of 2.5 l/h of absorbent having low loading was conducted by means of a membrane pump to the absorption column and introduced there as already described as a constituent of the main absorbent stream directly below the collecting tray for the acid water discharge in segment 4. The smaller substream of 460 ml/h of absorbent having low loading was, as likewise already described, passed by means of a further membrane pump into the stirred glass vessel of the acid water extraction stage.

From the bottoms circulation system (approx. 100 l/h, compressed air membrane pump) of the stripping column, approx. 3.5 kg of bottoms liquid were drawn off under level control through a stainless steel fabric filter and a regulating valve and fed to the vacuum distillation unit for the purpose of purifying distillation.

The vacuum distillation unit consisted of a metallized and vacuum-insulated glass column (purifying column) with internal diameter 50 mm and length 4000 mm. By means of forced-evaporation bottoms circulation (approx. 250 l/h, peripheral wheel centrifugal pump), a bottom temperature of 191° C. was maintained (p=4 bar). The absolute pressure in the bottom was approx. 230 mbar; the top pressure was 100 mbar. For the purpose of polymerization inhibition, 52 l (STP)/h of air were fed in above the level of the bottoms.

Between the bottom of the vacuum distillation column and the influx of the product-laden stream from the bottom circuit of the stripping column into the vacuum distillation column were mounted first 6 bubble-cap trays (tray separation: 5 cm) and above the influx a further 15 bubble-cap trays (tray separation: 5 cm), above which the possibility of sampling by means of a miniature membrane metering pump existed.

Above this sampling point, 10 sieve trays (6 equidistant holes of diameter 6.5 mm per tray) were mounted (tray separation: 5 cm) which extended upward up to a collecting tray, from which approx. 364 g/h of purified acrylic acid were discharged continuously as the target product and stored after cooling in a stock vessel.

Secondary component contents of the target product were:

| | |
|---|---|
| Acrylic acid (purity: without inhibitor content) All secondary component fractions below are reported here as weights based on the acrylic acid present | 99.54% by weight |
| Acetic acid | 0.186% |
| Propionic acid | 269 ppm |
| Maleic anhydride | 406 ppm |
| Formaldehyde | 344 ppm |
| Benzaldehyde | 186 ppm |
| Methacrylic acid | 1597 ppm |
| Water | 342 ppm |

A further amount (732 ml/h) of acrylic acid discharged from the collecting tray was recycled into the distillation column while maintaining its withdrawal temperature of approx. 75° C. to the uppermost of the sieve trays disposed below the target product draw.

Above the target product discharge were disposed a further 10 sieve trays (6 holes of diameter 5.5 mm per tray, tray separation: 5 cm) which permitted low boilers which were still present to accumulate toward the top of the column. Above these sieve trays was mounted a further collecting tray in order to collect the low boiler condensate which occurs as a result of condensation caused by indirect cooling in the top of the column (26° C., absolute pressure 100 mbar). The temperature at the collecting tray was 73° C. The low boiler condensate comprised:

| | |
|---|---|
| Acrylic acid | 98.42% by weight |
| Acetic acid | 1.02% by weight |
| Water | 0.427% by weight |
| Methacrolein | 0.012% by weight |
| Methacrylic acid | 0.021% by weight |
| Diphyl | 0.009% by weight |
| Propionic acid | 0.024% by weight |
| Furan-2-aldehyde | 0.010% by weight |
| Allyl acrylate | 0.009% by weight |
| Acrolein | 0.002% by weight |

From the total low boiler condensate stream withdrawn from the collecting tray, a main stream of 570 ml/h was fed as reflux back into the distillation column below the low boiler condensate collecting tray. The residual low boiler condensate stream of 190 ml/h which remained was cooled to 40° C. and fed to the acrylic acid absorption column above the 2nd segment thereof. To wet the walls for inhibition, a target product stream of 51 ml/h stabilized with 0.5% by weight of phenothiazine and having a temperature of 25° C. was sprayed in through a 4-hole full-jet nozzle in the uppermost region of the purifying column head.

The gas stream drawn off by means of a membrane vacuum pump at the top of the purifying column consisted mainly of inert gases and low boilers. In a cold trap cooled to 8° C., it was possible to remove from it another 4.6 g/h of condensable low boiler residual components. This residual component condensate separated in liquid form comprised:

| | |
|---|---|
| Acrylic acid | 89.65% by weight |
| Acetic acid | 2.45% by weight |
| Water | 7.24% by weight |
| Methacrolein | 0.197% by weight |
| Methacrylic acid | 0.029% by weight |
| Diphyl | 0.059% by weight |
| Propionic acid | 0.020% by weight |
| Furan-3-aldehyde | 0.021% by weight |
| Allyl acrylate | 0.007% by weight |
| Acrolein | 0.037% by weight |

The "inert gas" stream remaining minus the residual component condensate had the following composition:

| | % by volume |
|---|---|
| Nitrogen | remainder to 100% |
| Oxygen | 1.20 |
| Propane | 18.8 |
| Propene | 0.08 |
| Methane | 0.004 |
| Ethane | 0.052 |
| n-Butane | 0.069 |
| Isobutane | 0.146 |
| n-Butenes | 0 |
| Isobutene | 0.0 |
| Butadienes | 0.010 |
| Carbon monoxide | 0.372 |
| Carbon dioxide | 1.88 |
| Ethene | 0.022 |

It was recycled into the 2nd segment of the absorption column above the pressure decoupling valve and below the Rhomopak packing disposed above it.

At the bottom of the purifying column, the absorbent freed substantially of acrylic acid was drawn off under level control and passed as the total absorbent stream having very low loading to the stainless steel pressure wash column already described, and the pressure increase of the bottoms circulation pump of the purifying column was utilized for discharge from the vacuum.

The absorbent having very low loading comprised:

| | % by weight |
|---|---|
| Acetic acid | 0.012 |
| Furan-2-aldehyde | 0.0000 |
| Propionic acid | 0.0000 |
| Benzaldehyde | 0.097 |
| Acrylic acid | 0.056 |
| Methacrylic acid | 0.017 |
| Diphyl | 77.5 |
| DMP | 20.0 |
| Benzoic acid | 0.642 |
| Diacrylic acid | 0.910 |
| Water | 0.0283 |

To reduce reactant losses and to achieve a high yield, all analysis gas streams laden with reactant or target product were combined in a glass vessel (0.5 liter) and fed by means of a small membrane pump to the first compressor stage of the separation zone A and combined with the cooled product gas mixture of the dehydrogenation stage upstream of the compressor there and subsequently compressed. Based on converted propane, a yield of acrylic acid of 78.9 mol % was thus achieved.

The crude acrylic acid obtained as the target product may be further purified by crystallization or rectification as described in the document EP-A 616998 (with regard to the teaching of EP-A 912486) or as described in the document DE-A 19606877 (the mother liquor may be recycled into the absorption and/or into the purifying column) or as described in the document EP-A 648732 to obtain glacial acrylic acid which may then be free-radically polymerized in a manner known per se to prepare water-superabsorbent polymers. Both the crude acrylic acid obtained and the glacial acrylic acid obtained are outstandingly suitable for preparing esters of acrylic acid, for example for preparing alkyl acrylates.

Comparative Example 4

Similarly to the procedure in comparative examples 1 and 3, in a reaction zone A including downstream separation zone A, a starting reaction gas mixture for a reaction zone B is generated and has the following contents:

| Constituent | % by wt. (based on total amount) |
|---|---|
| Water | 1.10 |
| Tetradecane | 0.0101 |
| n-Butane | 0.091 |
| Isobutane | 0.47 |
| 1-Butene | 0.054 |
| Isobutene | 0.176 |
| Propane | 40.04 |
| Propene | 8.56 |
| $CO_2$ | 1.44 |
| $N_2$ | 36.9 |
| $O_2$ | 10.92 |
| Methane | 0.002 |
| Ethane | 0.204 |
| Ethylene | 0.034 |
| Hydrogen | 0 |

Reaction zone B consists of two tandem reactor systems operated in parallel (reactor lines) of which each is constructed in the same way as the tandem reactor system from the working example of DE-A 103 51 269 and is charged with catalyst. Each of the two reaction lines is charged with 61022 m³ (STP)/h of the aforementioned starting reaction gas mixture. The intermediate air feed between the two partial oxidation stages is 11200 m³ (STP)/h per line. In both partial oxidation stages, reaction gas and salt melt are conducted in countercurrent viewed over the reactor.

The hourly space velocity on the first reaction stage of propylene is about 110 l (STP)/l·h. The entrance temperature of the salt bath in the first reaction stage is 346° C.; the exit temperature of the salt bath from the first reaction stage is 349° C. The entrance temperature of the salt bath into the second reaction stage is 272° C. The exit temperature of the salt bath from the second reaction stage is 275° C. The starting reaction gas mixture is fed to the first-stage reactor at 300° C. The gas entrance temperature into the second reaction stage is 230° C. The salt melt pump outputs are as specified in DE-A 103 51 269. The entrance pressure into the first reaction stage is 1.9 bar. The entrance pressure into the second reaction stage is 1.4 bar. The propylene conversion in the first reaction stage is 97 mol % (based on single pass).

The acrolein conversion in the second reaction stage is 99.3 mol % (based on single pass).

The two product gas mixtures leave the two second partial oxidation stages with a temperature of 275° C. They are combined to give an overall stream of 145 000 m³ (STP)/h which has the following contents based on its total amount:

| | |
|---|---|
| Nitrogen | 42.75% by weight, |
| Oxygen | 3.0% by weight, |
| Carbon oxides | 3.11% by weight, |
| Water | 4.87% by weight, |
| Acrylic acid | 10.84% by weight, |
| Acetic acid | 0.30% by weight, |
| Acrolein | 0.06% by weight, |
| Diphyl | 0% by weight, |
| Formic acid | 0.03% by weight, |
| Formaldehyde | 0.09% by weight, |
| Propionic acid | 0.004% by weight, |
| Furfurals | 0.003% by weight, |
| Allyl acrylate | 0.001% by weight, |
| Benzaldehyde | 0.009% by weight, |
| Maleic anhydride | 0.127% by weight, |
| Benzoic acid | 0.015% by weight, |
| Methacrylic acid | 0.01% by weight, |
| Methacrolein | 0.015% by weight, |
| Phthalic anhydride | 0.001% by weight, |
| Methane | 0.001% by weight, |
| Hydrogen | 0% by weight, |
| Ethane | 0.17% by weight, |
| Ethene | 0.03% by weight, |
| Butanes | 0.47% by weight, |
| Butenes | 0.14% by weight, |
| Propane | 33.8% by weight and |
| Propene | 0.14% by weight. |

Cooling of Product Gas Mixture B

Product gas mixture B is conducted into a direct cooler of customary design with a diameter of 2.6 m and a height of 14.5 m, which is manufactured from austenitic steel (material 1.4571). Partial evaporation of the absorbent which is withdrawn from the bottom of the absorption column cools the product gas mixture to a temperature of 165.5° C. This is done by conducting the cooling medium in cocurrent to the cooling product gas mixture B and introducing it into the direct condenser via an impingement plate nozzle.

The cooled product gas mixture B is conducted into the bottom of the downstream absorption unit together with the unevaporated absorbent.

Absorption Unit

The absorption unit is designed as a tray column having 45 valve trays (the valve lids of the individual valves not being mounted) and 3 chimney trays, and is operated with a top pressure of 1.2 bar. A design with sieve trays or dual-flow trays as separating internals in the tray column is likewise conceivable.

The lowermost tray of the absorption column is designed as a double-walled chimney tray. Below this tray, the gas mixture leaving the product gas direct cooling is removed from the absorbent unevaporated in the cooling apparatus.

The mixture of unevaporated absorbent and product gas mixture leaving the direct cooling is introduced into the absorption column with a tangential impulse. A cyclone ring prevents direct entrainment of drops into the chimney of the lowermost tray.

The bottom temperature of the absorption unit is 162.7° C. From the bottom of the absorption unit, 1067 m³/h of bottoms liquid having the following composition are drawn off:

| | |
|---|---|
| Diphyl (mixture of diphenyl and diphenyl ether in a weight ratio of 2.8:1) | 54.27% by weight, |
| Dimethyl phthalate | 36.97% by weight, |
| Diacrylic acid | 0.95% by weight, |
| Acrylic acid | 4.75% by weight, |
| Phenothiazine | 0.65% by weight, |
| Phthalic anhydride | 0.1% by weight, |
| Benzoic acid | 1.87% by weight, |
| Maleic anhydride | 0.24% by weight, |
| Benzaldehyde | 0.11% by weight, |
| Formic acid | 0.005% by weight, |
| Acrolein | 0.002% by weight, |
| Water | 0.01% by weight, |
| Acetic acid | 0.04% by weight and |
| Furfurals | 0.003% by weight. |

The bottoms liquid (liquid effluent of the absorption unit) is predominantly recycled as coolant with the aid of a centrifugal pump into the direct cooling of product gas mixture B. A portion of 0.3% based on the total amount is withdrawn and sent to a distillation unit.

The feed of fresh absorbent and of absorbent having low loading into the absorption column is at the 34th tray counted from the bottom, directly below the 3rd chimney tray. This feed of absorbent having low loading consists of a polymerization inhibitor-containing substream of 86.6% by weight based on the total amount of feed, which stems from the scrubbing unit which is used for cycle gas scrubbing and is still to be described below, and of a substream of 13.4% by weight based on the total amount of feed from the acid water extraction. The temperature of the feed stream is 51.9° C.

From the lowermost tray of the absorption unit, which is designed as a collecting tray (chimney tray), 1728 m³/h of the absorbent laden with acrylic acid (of the absorbate) are withdrawn (as a further liquid effluent of the absorption column). The withdrawal temperature is 119.6° C. The absorbate drawn off via a centrifugal pump comprises the following constituents (the proportions are based on the total amount):

| | |
|---|---|
| Diphyl | 52.55% by weight, |
| Dimethyl phthalate | 12.11% by weight, |
| Diacrylic acid | 1.38% by weight, |
| Acrylic acid | 30.1% by weight, |
| Phenothiazine | 0.03% by weight, |
| Phthalic anhydride | 0.08% by weight, |
| Benzoic acid | 1.22% by weight, |
| Maleic anhydride | 1.06% by weight, |
| Benzaldehyde | 0.61% by weight, |
| Formic acid | 0.03% by weight, |
| Acrolein | 0.007% by weight, |
| Water | 0.20% by weight, |
| Acetic acid | 0.28% by weight, |
| Propane | 0.19% by weight, |
| Propionic acid | 0.01% by weight, |
| Formaldehyde | 0.001% by weight, |
| Allyl acrylate | 0.005% by weight, |
| Furfurals | 0.02% by weight and |
| Methacrylic acid | 0.07% by weight. |

11.4% by weight based on the total amount of the absorbate is fed to a desorption unit, 3.1% by weight based on the total amount is fed directly to the bottom of the absorption column and 85.5% by weight is recycled into the absorption unit via series-connected heat exchangers in which it is cooled by 15 K to the sixth tray counted from the bottom.

The heat removed in the first heat exchanger designed as a tube bundle heat exchanger is used to partially evaporate the acid water obtained in the condensation unit which is still to be described. The exit temperature of the absorbate leaving this heat exchanger is 113.3° C. The absorbate is further cooled to the feed temperature of the recycling in air coolers.

The trays between the first chimney tray up to this feed tray are designed as 4-flow valve trays (VV12 steel without lids). The distance between two trays is 0.7 m. The trays above this feed tray up to the 13th tray, counted from the bottom, are designed as two-flow valve trays (VV12 steel without lids) and are mounted in a separation of 0.5 m.

Above the 13th tray, counted from the bottom, is mounted a further collecting tray designed as a double-walled chimney tray and a liquid draw stream with a temperature of 71.8° C. is withdrawn via a centrifugal pump. 9% by weight of the total amount withdrawn at this point is directly introduced as reflux below this second collecting tray, while from 1% by weight to 10% by weight based on this amount of reflux are utilized for spraying the second collecting tray via nozzles. The remaining amount drawn off is cooled to 59.4° C. with the aid of air coolers and introduced to the 19th tray counted from the bottom. The trays between the second collecting tray up to the 19th tray, counted from the bottom, are designed as 4-flow valve trays (VV12 steel without lids), and the distance between the trays is 0.6 m.

The acrylic acid-containing low boiler stream withdrawn via the top of the rectification unit which is still to be described below is also fed into the draw stream of the second collecting tray. In addition, this point is also suitable on the industrial scale for the feeding of acrylic acid-containing streams, for example off-spec crude acrylic acid or acrylic acid-containing streams from other process stages, for example from glacial acrylic acid preparation by distillation or crystallization.

The trays above the 19th tray, counted from the bottom, to the feed point of the fresh absorbent or absorbent having low loading into the absorption column are designed as 2-flow valve trays (VV12 steel without lids) with a distance between the trays of in each case 0.5 m. Above the 34th tray counted from the bottom is disposed a third collecting tray designed as a double-walled chimney tray.

The remaining residual product gas mixture which has not been absorbed into the absorbent and comprises in particular low boilers and noncondensables is cooled in a condensation unit which is attached above the third collecting tray. The condensation unit is designed as direct cooling and contains ten 2-flow valve trays (VV12 steel without lids) which have a separation from one another of 0.5 m. For direct cooling, aqueous low boiler fraction which has already been condensed is drawn off at the third collecting tray. 2% by weight based on the entire amount of acid water condensate drawn off at the third collecting tray is discharged at a temperature of 45° C. and sent to an acid water extraction. The acid water discharged has substantially the following contents:

| | |
|---|---|
| Acrylic acid | 4.02% by weight, |
| Acetic acid | 5.04% by weight, |
| Water | 69.84% by weight, |
| Diphyl | 12.95% by weight, |
| Dimethyl phthalate | 2.51% by weight, |
| Formaldehyde | 0.02% by weight, |
| Diacrylic acid | 0.2% by weight, |
| Allyl acrylate | 0.004% by weight, |
| Furfurals | 0.02% by weight, |

-continued

| | |
|---|---|
| Propionic acid | 0.0015% by weight, |
| Formic acid | 0.62% by weight, |
| Benzaldehyde | 0.84% by weight, |
| Maleic anhydride | 0.05% by weight, |
| Benzoic acid | 0.25% by weight, |
| Maleic acid | 1.40% by weight, |
| Phthalic anhydride | 0.01% by weight, |
| Phenothiazine | 0.007% by weight, |
| Acrolein | 0.02% by weight, |
| Methacrylic acid | 0.05% by weight, |
| Methacrolein | 0.005% by weight, |
| Butanes | 0.21% by weight and |
| Butenes | 0.08% by weight. |

The undischarged acid water condensate is cooled to 33° C. in a tube bundle heat exchanger. 79% by weight based on the amount of acid water condensate cooled to 33° C. are introduced at the 40th tray counted from the bottom. The remaining amount of acid water condensate is cooled to 16° C. in a further heat exchanger. This heat exchanger is coupled energetically to the evaporator unit needed for the evaporation of the liquid propane. The residual gas mixture remaining in gaseous form in the acid water condensation leaves the absorption unit at a temperature of 29° C. and comprises substantially the following constituents:

| | |
|---|---|
| Nitrogen | 50.40% by weight, |
| Oxygen | 3.57% by weight, |
| Carbon oxides | 3.65% by weight, |
| Water | 1.46% by weight, |
| Acetic acid | 0.058% by weight, |
| Acrylic acid | 0.041% by weight, |
| Acrolein | 0.067% by weight, |
| Diphyl | 0.008% by weight, |
| Formic acid | 0.003% by weight, |
| Ethane | 0.20% by weight, |
| Ethene | 0.03% by weight, |
| Butenes | 0.15% by weight, |
| Butanes | 0.55% by weight, |
| Propane | 39.62% by weight and |
| Propene | 0.17% by weight. |

The residual gas stream remaining in the acid water condensation (cycle gas) is conducted out of the column via a demister and superheated by 6 K in a tube bundle heat exchanger. This prevents a possible condensation in the offgas gas lines. This residual gas stream is compressed to a pressure of 3.3 bar by an electrically driven turbocompressor.

Of this residual gas stream, 20% by volume based on the total amount of the residual gas stream are used as stripping gas in a wash column which has yet to be described. The remaining residual gas stream is recycled into reaction zone A for heterogeneously catalyzed propane dehydrogenation.

Desorption Unit

The absorbate effectively discharged from the lowermost collecting tray of the absorption unit is fed to a desorption unit in order to free it of low boilers still present therein. The absorbate is initially heated to 130° C. in a steam-heated tube bundle heat exchanger and then fed to a desorption column at the top thereof. As this is done, 5% by weight of absorbate sprayed in via nozzles, based on the total amount of the absorbate sent to the desorption column, is utilized for moistening the column walls, the manhole and the column hood.

The column internals used in the desorption column are 38 dual-flow trays on which baffles are mounted. The hole diameter of the trays is 30 mm from tray 1, counted from the bottom, up to tray 9, 25 mm on tray 10 and 20 mm from tray 11 up to the top of the column. The tray separation between the individual trays is 0.5 m. The top pressure of the desorption column is 1.83 bar.

The heat is supplied in the bottom of the column via two evaporators with forced circulation operated in parallel.

The stripping gas fed directly in the bottom of the desorption column is a substream of the residual gas stream from the top of the absorption unit after it has been scrubbed in the scrubbing column which is still to be described. Before it enters the desorption column, the stripping gas is mixed with a substream of the bottoms liquid withdrawn at the bottom of the desorption column and heated in the evaporator, and preheated to 120° C. in a tube bundle heat exchanger. The substream of the bottoms liquid which is mixed with the stripping gas is 9% by weight based on the total amount of bottoms liquid drawn off. If desired, this mixing with heated bottoms liquid may also be dispensed with.

The acrylic acid-laden absorbent obtained in the bottom of the desorption column comprises:

| | |
|---|---|
| Diphyl | 62.8% by weight, |
| Dimethyl phthalate | 14.7% by weight, |
| Diacrylic acid | 1.8% by weight, |
| Acrylic acid | 17.1% by weight, |
| Acetic acid | 0.04% by weight, |
| Formic acid | 0.004% by weight, |
| Propionic acid | 0.006% by weight, |
| Phenothiazine | 0.04% by weight, |
| Phthalic anhydride | 0.1% by weight, |
| Benzoic acid | 1.5% by weight, |
| Maleic anhydride | 1.1% by weight, |
| Methacrylic acid | 0.06% by weight, |
| Benzaldehyde | 0.62% by weight and |
| Furfural | 0.02% by weight. |

The bottoms liquid withdrawn from the bottom of the column is fed to the forced-circulation evaporators with a temperature of 131.5° C. and heated to 150° C. A substream of 63% by weight based on the total amount of bottoms liquid withdrawn is recycled into the desorption column to the 8th tray counted from the bottom.

The stripping gas which is laden with low boilers and is obtained at the top of the desorption column is recycled into the direct cooler utilized for cooling of the product gas mixture B. The recycled laden stripping gas also includes the liquid entrainment of the uppermost tray of the desorption column and comprises substantially the following constituents:

| | |
|---|---|
| Nitrogen | 26.75% by weight, |
| Oxygen | 1.89% by weight, |
| Carbon oxides | 1.94% by weight, |
| Acrylic acid | 36.84% by weight, |
| Diphyl | 7.57% by weight, |
| Water | 0.95% by weight, |
| Acetic acid | 0.56% by weight, |
| Dimethyl phthalate | 1.39% by weight, |
| Formaldehyde | 0.0% by weight, |
| Acrolein | 0.01% by weight, |
| Formic acid | 0.05% by weight, |
| Propionic acid | 0.01% by weight, |
| Allyl acrylate | 0.01% by weight, |

-continued

| | |
|---|---|
| Diacrylic acid | 0.16% by weight, |
| Phthalic anhydride | 0.0% by weight, |
| Benzoic acid | 0.15% by weight, |
| Maleic anhydride | 0.47% by weight, |
| Benzaldehyde | 0.27% by weight, |
| Furfurals | 0.01% by weight, |
| Ethane | 0.1% by weight, |
| Propane | 20.4% by weight, |
| Propene | 0.1% by weight, |
| Butenes | 0.06% by weight and |
| Butanes | 0.23% by weight. |

Rectification Unit

The substream which is withdrawn from the desorption unit after the forced-circulation evaporators and consists mainly of acrylic acid, Diphyl and dimethyl phthalate is conducted into a rectification unit comprising a rectifying section and a stripping section.

The rectification unit consists of 43 dual-flow trays on which baffles are mounted, the trays having different hole diameters: 50 mm from the 1st tray, counted from the bottom, up to the 10th tray, 25 mm from the 11th tray up to the 13th tray, and 14 mm from the 14th tray up to the uppermost tray. The distance between the individual trays is in each case 0.4 m. The distance between 8th and 9th tray, counted from the bottom, is 1 m.

The column is operated with a top pressure of 106 mbar. The laden absorbent freed partly of low boilers in the desorption unit is fed via a ring line having several nozzles to the 8th tray counted from the bottom.

Below the 1st tray, 430 m$^3$ (STP)/h of air are fed to the column via a ring line having several feed points.

The heat is supplied in the bottom of the columns via two external circulation evaporators with forced circulation operated in parallel. The bottom temperature of the rectification unit is typically 188° C. The high boiler fraction which condenses into the bottom of the rectification column comprises substantially the following constituents:

| | |
|---|---|
| Diphyl | 75.6% by weight, |
| Dimethyl phthalate | 17.7% by weight, |
| Diacrylic acid | 1.85% by weight, |
| Acrylic acid | 0.79% by weight, |
| Phenothiazine | 0.05% by weight, |
| Phthalic anhydride | 0.1% by weight, |
| Benzoic acid | 1.75% by weight, |
| Maleic anhydride | 1.3% by weight, |
| Methacrylic acid | 0.06% by weight, |
| Benzaldehyde | 0.74% by weight and |
| Furfurals | 0.015% by weight. |

The bottoms liquid which is withdrawn from the rectification unit and comprises the high-boiling absorbent in condensed form is discharged to an extent of 83% by weight based on the feed into the rectification unit and recycled partly via a heat exchanger into the bottom region of the rectification column. The discharged low boiler fraction is sent to the scrubbing unit via a solids separator (cyclone) and supplemented if appropriate by fresh absorbent (Diphyl and dimethyl phthalate). A small substream of 1.2% by weight based on the total amount of bottoms liquid discharged is sent to the bottom region of the absorption.

Crude acrylic acid is withdrawn via side draw removal from 27 trays above the feed into the rectification column. The crude acrylic acid is withdrawn via a dual-flow tray with integrated central draw cup. The withdrawn crude acrylic acid comprises substantially the following constituents:

| | |
|---|---|
| Acrylic acid | 99.66% by weight, |
| Acetic acid | 0.135% by weight, |
| Water | 0.007% by weight, |
| Formic acid | 0.002% by weight, |
| Propionic acid | 0.036% by weight, |
| Furfurals | 0.022% by weight, |
| Allyl acrylate | 0.011% by weight, |
| Benzaldehyde | 0.008% by weight, |
| Maleic anhydride | 0.008% by weight, |
| Methacrylic acid | 0.06% by weight, |
| Diacrylic acid | 0.02% by weight and |
| Phenothiazine | 0.025% by weight. |

The withdrawn crude acrylic acid is cooled to 25° C. by means of two heat exchangers connected in series. Of the withdrawn crude acrylic acid, 15.5% by weight, based on the feed into the rectification column, is discharged and a smaller substream is used as solvent for the polymerization inhibitor.

The low boiler stream removed at the top of the rectification column is cooled in two stages by two direct coolers. Both stages are designed as a cocurrent quench, the condensate of the first stage having a temperature of 52° C. and the condensate of the second stage having a temperature of 24.5° C. The vapor line of the second condensation stage leads to the vacuum unit. Two liquid-ring pumps are operated in parallel, and the barrier liquid used is, according to DE-A-10143565, the condensate from the second condensation stage. In a downstream vessel, the liquid phase, primarily the ring liquid, is separated from the uncondensable fractions which form the offgas of the rectification unit. This has substantially the following composition:

| | |
|---|---|
| Nitrogen | 48% by weight, |
| Oxygen | 14.5% by weight, |
| Acrylic acid | 2.3% by weight, |
| Acetic acid | 0.09% by weight, |
| Water | 0.25% by weight, |
| Acrolein | 0.001% by weight, |
| Formic acid | 0.04% by weight, |
| Allyl acrylate | 0.004% by weight, |
| Carbon oxides | 0.03% by weight, |
| Propane | 33.65% by weight, |
| Propene | 0.03% by weight, |
| Butanes | 0.85% by weight and |
| Butenes | 0.21% by weight. |

The offgas of the rectification unit is incinerated together with other production residues. However, it is also conceivable at high propane contents of this vacuum offgas to recycle this stream into the absorption.

The low boiler stream removed via the top of the rectification column comprises substantially the following components:

| | |
|---|---|
| Acrylic acid | 98.44% by weight, |
| Acetic acid | 0.94% by weight, |
| Water | 0.35 by weight, |
| Phenothiazine | 0.028% by weight, |
| Diacrylic acid | 0.027% by weight, |
| Allyl acrylate | 0.05% by weight, |
| Furfurals | 0.006% by weight, |
| Propionic acid | 0.034% by weight, |

| | |
|---|---|
| Methacrylic acid | 0.01% by weight, |
| Formic acid | 0.07% by weight and |
| Acrolein | 0.001% by weight. |

A substream of the liquid withdrawn as low boiler fraction of 47.6% by weight based on the feed into the rectification column is used as reflux which is introduced via several nozzles. A small portion is also utilized to spray the column hood and the vapor line with inhibitor-containing condensate by means of nozzles. 1.3% by weight of the low boiler fraction based on the feed into the rectification column is discharged and recycled into the absorption unit as described there.

The polymerization inhibitor used is phenothiazine. The inhibitor is made up as a solution with an inhibitor concentration of 1.1% by weight in the crude acrylic acid removed via side draw removal as described and added continuously to the condensed low boiler reflux and the condensates of the two direct cooling stages of the rectification unit. The solid stabilizer is metered in in the form of flakes or pellets via conveying screws into the stabilizer mixture vessel.

Scrubbing Unit

The scrubbing column is operated with a top pressure of 3 bar. The separating internals used are dual-flow trays having a hole diameter of 30 mm. 30 of these trays are mounted with a tray separation of 0.4 m.

The scrubbing liquid used is the bottoms liquid from the rectification unit. The scrubbing liquid is introduced at the top of the scrubbing column with a temperature of 50° C. Below the lowermost tray, the cycle gas coming from the absorption unit is fed in after it has been cooled beforehand to the entrance temperature of 50° C. The amount of cycle gas fed is 37% by weight of the amount of scrubbing liquid fed.

The liquid obtained in the column bottom comprises substantially the following components:

| | |
|---|---|
| Diphyl | 75% by weight, |
| Dimethyl phthalate | 17.6% by weight, |
| Diacrylic acid | 1.9% by weight, |
| Acrylic acid | 0.8% by weight, |
| Maleic anhydride | 1.3% by weight, |
| Phenothiazine | 0.05% by weight, |
| Phthalic anhydride | 0.1% by weight, |
| Benzoic acid | 1.7% by weight, |
| Acrolein | 0.02% by weight, |
| Water | 0.17% by weight, |
| Acetic acid | 0.02% by weight, |
| Benzaldehyde | 0.74% by weight, |
| Furfurals | 0.015% by weight, |
| Methacrylic acid | 0.06% by weight and |
| Propane | 0.5% by weight. |

The bottoms liquid obtained in the scrubbing unit is discharged and divided into two portions in a weight ratio of 7.2 to 1. The larger substream is introduced into the absorption column as described, while the small substream is sent to the acid water extraction.

The scrubbed cycle gas still comprises substantially the following constituents:

| | |
|---|---|
| Nitrogen | 51.62% by weight, |
| Oxygen | 3.66% by weight, |
| Carbon oxides | 3.73% by weight, |
| Water | 1.01% by weight, |
| Acrylic acid | 0.02% by weight, |
| Diphyl | 0.03% by weight, |
| Benzaldehyde | 0.01% by weight, |
| Maleic anhydride | 0.015% by weight, |
| Propane | 38.96% by weight, |
| Propene | 0.16% by weight, |
| Butanes | 0.42% by weight, |
| Butenes | 0.11% by weight and |
| Ethane | 0.2% by weight. |

The scrubbed cycle gas is passed as stripping gas into the desorption unit described.

Acid Water Extraction

The acid water condensate from the absorption unit is extracted in an extraction unit using a portion of the liquid effluent from the scrubbing unit which is sent to it. The extraction unit consists of a stirred vessel with a two-stage impeller stirrer and a horizontal settling vessel. Inlet and outlet in the settling vessel are separated from one another by internals at right angles to the flow direction. The entrance temperature of the acid water condensate into the extraction unit is 45° C. The mass ratio of amount of bottom effluent of the scrubbing unit and acid water from the acid water condensation is 0.8 to 1.

The aqueous extract obtained in the extraction unit takes up polar constituents such as diacrylic acid (Michael adduct) and maleic anhydride from the bottom effluent of the scrubbing unit, and the latter is hydrolyzed at the same time. It comprises substantially the following components:

| | |
|---|---|
| Water | 70-95% by weight, |
| Acetic acid | 2-10% by weight, |
| Acrylic acid | 1-5% by weight, |
| Formaldehyde | 2-10% by weight, |
| Maleic acid | 1-5% by weight, |
| Diacrylic acid | 1-5% by weight, |
| Diphyl | 0.01-0.05% by weight, |
| Dimethyl phthalate | 0.1-1% by weight, |
| Allyl acrylate | 0.0005-0.002% by weight, |
| Furfurals | 0.001-0.001% by weight, |
| Formic acid | 0.2-2% by weight, |
| Benzaldehyde | 0.01-0.05% by weight, |
| Benzoic acid | 0.05-0.2% by weight, |
| Maleic acid | 0.5-3% by weight and |
| Phthalic anhydride | 0.01-0.1% by weight. |

The discharged aqueous phase is incinerated together with the other production residues. Before it is incinerated, the acid water is partly evaporated. The heat required for this purpose is withdrawn from the absorption unit via tube bundle heat exchangers, which cools condensate obtained there as described on the first collecting tray.

The organic phase obtained in the extraction unit (the raffinate) comprises substantially the following components:

| | |
|---|---|
| Diphyl | 76.3% by weight, |
| Dimethyl phthalate | 17.2% by weight, |
| Acrylic acid | 1.1% by weight, |
| Maleic anhydride | 0.35% by weight, |
| Diacrylic acid | 0.85% by weight, |
| Phenothiazine | 0.05% by weight, |

-continued

| | |
|---|---|
| Phthalic anhydride | 0.1% by weight, |
| Benzoic acid | 1.55% by weight, |
| Methacrylic acid | 0.03% by weight, |
| Propionic acid | 0.02% by weight, |
| Benzaldehyde | 1.16% by weight, |
| Formic acid | 0.05% by weight, |
| Acrolein | 0.04% by weight, |
| Water | 0.7% by weight, |
| Acetic acid | 0.41% by weight and |
| Furfurals | 0.02% by weight. |

The discharged organic phase is sent in the absorption unit as described there.

High Boiler Distillation

The described portion of the bottom effluent of the absorption unit is sent to a distillation unit and separated therein by heating into a high boiler fraction and a low boiler fraction. The distillation unit is designed with one stage and is operated at a pressure of 90 mbar. However, an industrial design in a distillation column with the separating internals known to those skilled in the art is also conceivable.

The heat is supplied via an external forced-circulation evaporator. The superheating of the circulating liquid there is 5 K. In the distillation unit, a temperature of 188° C. is established.

From the amount circulated in the forced-circulation evaporator, a portion is withdrawn and, after dilution with a suitable diluent (for example dimethylformamide or methanol), incinerated together with other production residues.

The high boiler fraction comprises substantially the following components:

| | |
|---|---|
| Diphyl | 25.8% by weight, |
| Dimethyl phthalate | 43.2% by weight, |
| Phenothiazine | 29.1% by weight, |
| Acrylic acid | 0.13% by weight, |
| Diacrylic acid | 0.6% by weight, |
| Phthalic anhydride | 0.3% by weight, |
| Benzoic acid | 1% by weight, |
| Maleic anhydride | 0.02% by weight and |
| Benzaldehyde | 0.01% by weight. |

Of the high boiler fraction, 1.7% by weight based on the feed amount sent to the distillation unit is discharged and incinerated.

The low boiler fraction converted to the vapor phase in the distillation unit is cooled and condensed by a combination of direct and indirect cooling. To this end, the already condensed low boiler fraction is sprayed within the vapor of the distillation unit and cooled together with the uncondensed vapor by means of a tube bundle heat exchanger, and the cooled liquid is sprayed within the vapor above the heat exchanger. The stream leaving the cooler has a temperature of 52° C. and is separated in a vessel into gas and liquid phase. The liquid low boiler fraction obtained in the distillation unit comprises substantially the following components:

| | |
|---|---|
| Acrylic acid | 4.5% by weight, |
| Diphyl | 54.8% by weight, |
| Dimethyl phthalate | 36.7% by weight, |
| Diacrylic acid | 1.25% by weight, |
| Acetic acid | 0.04% by weight, |
| Water | 0.01% by weight, |
| Formic acid | 0.005% by weight, |
| Phenothiazine | 0.165% by weight, |
| Benzaldehyde | 0.12% by weight, |
| Maleic anhydride | 0.24% by weight, |
| Benzoic acid | 1.89% by weight, |
| Phthalic anhydride | 0.14% by weight, |
| Furfurals | 0.003% by weight and |
| Acrolein | 0.002% by weight. |

A centrifugal pump is used to spray the liquid low boiler fraction as described above the tube bundle heat transferer as described. 98.2% of the liquid withdrawn as low boiler fraction based on the feed amounts sent to the distillation unit is discharged and recycled into the absorption unit below the first chimney tray.

The offgas leaving the distillation unit in gaseous form comprises substantially the following components:

| | |
|---|---|
| Acrylic acid | 4.8% by weight, |
| Acetic acid | 0.2% by weight, |
| Water | 2.2% by weight, |
| Diphyl | 0.8% by weight, |
| Dimethyl phthalate | 0.1% by weight, |
| Formaldehyde | 0.13% by weight, |
| Acrolein | 0.13% by weight, |
| Propionic acid | 0.002% by weight, |
| Furfurals | 0.003% by weight, |
| Benzaldehyde | 0.07% by weight, |
| Maleic anhydride | 0.1% by weight, |
| Benzoic acid | 0.01% by weight, |
| Phthalic anhydride | 0.01% by weight, |
| Diacrylic acid | 0% by weight, |
| Formic acid | 0.02% by weight, |
| Allyl acrylate | 0.003% by weight, |
| Butanes | 1.1% by weight, |
| Butenes | 0.3% by weight and |
| Propane | 89.9% by weight. |

This offgas is incinerated together with the other production residues.

The crude acrylic acid obtained may be further processed in a manner known per se in further process stages to give pure acrylic acid. Suitable processes for this purpose are a one-stage process or, in the case of crude acrylic acid having significant fractions of low-boiling secondary components, at two-stage distillative process with preceding aldehyde treatment by a compound containing at least one primary amino group (such as hydrazine or aminoguanidine hydrogencarbonate) according to the teachings of EP-A 270 999, EP-A 648 732, and also a crystallizative process according to the teachings of EP-A 616 998, EP-A 792 867, EP-A 1 189 861 and WO 98/01404.

When the pure acrylic acid is obtained in a crystallizative process stage such as a layer crystallization, not only the pure acrylic acid but also an acrylic acid-containing mother liquor/acid stream is obtained, which can be recycled as described above into the absorption unit for obtaining the crude acrylic acid.

EXAMPLE 1

The procedure of Comparative Example 1 was repeated. However, the (overall) residual gas was not conducted into the evaporator upstream of the first heater, but rather, compressed to the appropriate pressure together with the 195 l (STP)/h of compressed air, into the heater upstream of the third dehydrogenation reactor.

The $CO_2$ content of the reaction gas mixture leaving the third dehydrogenation reactor subsequently fell from 3.25% by volume to 1.6% by volume.

This demonstrates that the inventive procedure is associated with a full combustion of the $C_3$ hydrocarbons involved reduced to less than half.

In addition, it was possible to operate this inventive procedure over a period of 7500 operating hours substantially without significant impairments.

EXAMPLE 2

Here too, the steady operating state is described.

A shaft furnace reactor which is designed as a tray reactor and configured adiabatically has, as a first section of a reaction zone A, two catalyst beds arranged in series in flow direction, each of which is charged as a fixed bed with a dehydrogenation catalyst according to Comparative Example 1. Upstream of each fixed bed is disposed a static gas mixer.

To the first catalyst bed in flow direction is fed a starting reaction gas mixture which has the following composition:
 a) recycled product gas mixture A which has a temperature of 617° C. and a pressure of 2.75 bar in an amount of 132 872 m³ (STP)/h, containing
  26.4% by volume of propane,
  6.6% by volume of propene (propylene),
  0.1% by volume of $H_2$,
  8.8% by volume of $H_2O$ and
  0% by volume of $O_2$ and
 b) 8758 m³ (STP)/h of crude propane according to Comparative Example 1.

The temperature of the crude propane is such that the temperature of the starting reaction gas mixture is 560° C.

The amount of starting reaction gas mixture is 141 630 m³ (STP)/h, with the following contents:
 31.0% by volume of propane,
 6.2% by volume of propene,
 0.1% by volume of $H_2$,
 8.2% by volume of $H_2O$ and
 0% by volume of $O_2$.

The pressure of the starting reaction gas mixture before entry into the first catalyst bed is 2.75 bar.

The bed height of the first catalyst bed flowed through by the starting reaction gas mixture is such that the reaction gas mixture leaves this fixed catalyst bed with the following contents:
 26.4% by volume of propane,
 9.5% by volume of propene,
 3.6% by volume of $H_2$,
 7.9% by volume of $H_2O$ and
 0% by volume of $O_2$.

The leaving amount is 146 533 m³ (STP)/h. The leaving temperature is 500° C. and the leaving pressure is 2.65 bar. The propane conversion which is established in the first catalyst bed is 11.8 mol % of the propane fed.

6250 m³ (STP)/h of air are metered to the reaction gas mixture leaving the first fixed catalyst bed as described. The air is preheated to 500° C. and its pressure is such that the pressure of the reaction gas mixture resulting after the air metering is 2.65 bar.

When it flows through the second fixed catalyst bed, half of the molecular hydrogen present in the reaction gas mixture is initially combusted with the molecular oxygen metered in the form of air to give water. This heats the reaction gas mixture to 550° C. In the further course of the flow through the second fixed catalyst bed, there is heterogeneously catalyzed dehydrogenation of the propane. The bed height of the second fixed catalyst bed is such that the reaction gas mixture leaves the second fixed catalyst bed at a temperature of 513° C. and a pressure of 2.55 bar with the following contents in an amount of 154 746 m³ (STP)/h:
 22.9% by volume of propane,
 11.9% by volume of propene,
 3.9% by volume of $H_2$,
 9.2% by volume of $H_2O$ and
 0% by volume of $O_2$.

To this product gas mixture A* are initially fed 761.6 m³ (STP)/h of molecular hydrogen. Subsequently, 112 792 m³ (STP)/h of overall residual gas from separation zone B are added at a temperature of 567° C. The overall residual gas has the following contents:
 31.1% by volume of propane,
 0% by volume of propene,
 0% by volume of $H_2$,
 1.9% by volume of $H_2O$ and
 3.0% by volume of $O_2$.

The overall residual gas is fed by the principle of a jet pump operated with this overall residual gas as a driving jet, and the conveying direction of the driving jet decompressed through a driving nozzle via a mixing zone and a diffuser points into the second section of reaction zone A and the sucking direction of the sucking nozzle points in the direction of the mixture of molecular hydrogen and product gas mixture A*.

The resulting reaction gas mixture A* flows in an amount of 267 538 m³ (STP)/h and at a temperature of 536° C. and a pressure of 2.85 bar into a second shaft furnace reactor which forms the second section of reaction zone A, is likewise configured adiabatically and comprises a fixed catalyst bed which is likewise charged with the dehydrogenation catalyst according to Comparative Example 1. It has the following contents:
 26.3% by volume of propane,
 6.4% by volume of propene,
 2.6% by volume of $H_2$,
 6.1% by volume of $H_2O$ and
 1.3% by volume of $O_2$.

When it flows through this third fixed catalyst bed, the molecular oxygen present in reaction gas mixture A* is initially combusted substantially fully with the molecular hydrogen present therein to give water, which heats the reaction gas mixture to 620° C.

The bed height of the third fixed catalyst bed is such that there is still a small degree of heterogeneously catalyzed propane dehydrogenation in the reaction gas mixture until it leaves the third fixed catalyst bed.

As a result, 265 745 m³ (STP)/h of product gas mixture A leave the third fixed catalyst bed at a temperature of 617° C. and a pressure of 2.75 bar. It contains the following contents:
 26.4% by volume of propane,
 6.6% by volume of propene,
 0.1% by volume of $H_2$,
 8.8% by volume of $H_2O$ and
 0% by volume of $O_2$.

Product gas mixture A is divided into two halves of identical composition.

Of this, one half is recycled into the first section of reaction zone A as a constituent of the starting reaction gas mixture therefor.

The other half is fed via an indirect heat exchanger W for gases to separation zone A. In the heat exchanger, the residual gas from separation zone B which is recycled into reaction zone A is heated to 567° C.

In separation zone B, the propane and propene present in the second half of product gas mixture A are removed absorptively therefrom as in Comparative Example 1 and subjected as in Comparative Example 1 to the two-stage heterogeneously catalyzed partial oxidation of propene to acrylic acid in reaction zone B.

From the resulting product gas mixture B, the acrylic acid is removed as in Comparative Example 1 in separation zone B, and the remaining overall residual gas is compressed (to approx. 4 bar) and fed as described via the heat exchanger W to the jet pump operated with the overall residual gas as a driving jet and combined with the product gas mixture A* supplemented with molecular hydrogen. The amount of acrylic acid removed in separation zone B amounts to 332 kmol/h. The amount of residual gas in the above-described gas mixtures consists substantially of molecular nitrogen and of small amounts of carbon oxides. The process described can be operated over a prolonged period substantially without reduction.

EXAMPLE 3

Here too, the steady operating state is described.

A shaft furnace reactor which is designed as a tray reactor and configured adiabatically has, as a first section of a reaction zone A, two catalyst beds arranged in series in flow direction, each of which is charged as a fixed bed with a dehydrogenation catalyst according to Comparative Example 1. Upstream of each fixed bed is disposed a static gas mixer.

To the first catalyst bed in flow direction is fed a starting reaction gas mixture which has the following composition:
a) recycled product gas mixture A which has a temperature of 676° C. and a pressure of 1.75 bar in an amount of 106 510 m$^3$ (STP)/h, containing
   12.3% by volume of propane,
   8.2% by volume of propene (propylene),
   2.2% by volume of H$_2$,
   7.7% by volume of H$_2$O and
   0% by volume of O$_2$ and
b) 8758 m$^3$ (STP)/h of crude propane according to Comparative Example 1.

The temperature of the crude propane is such that the temperature of the starting reaction mixture is 652° C.

The amount of starting reaction gas mixture is 115 268 m$^3$ (STP)/h, with the following contents:
   19.0% by volume of propane,
   7.6% by volume of propene,
   2.0% by volume of H$_2$,
   7.1% by volume of H$_2$O and
   0% by volume of O$_2$.

The pressure of the starting reaction gas mixture before entry into the first catalyst bed is 1.75 bar.

The bed height of the first catalyst bed flowed through by the starting reaction gas mixture is such that the reaction gas mixture leaves this fixed catalyst bed with the following contents:
   15.1% by volume of propane,
   10.6% by volume of propene,
   5.1% by volume of H$_2$,
   6.9% by volume of H$_2$O and
   0.0% by volume of O$_2$.

The leaving amount is 119 308 m$^3$ (STP)/h. The leaving temperature is 590° C. and the leaving pressure is 1.65 bar.

The propane conversion which is established in the first catalyst bed is 17.5 mol % of the propane fed.

2598 m$^3$ (STP)/h of air are metered to the reaction gas mixture leaving the first fixed catalyst bed as described. The air is preheated to 590° C. and its pressure is such that the pressure of the reaction gas mixture resulting after the air metering is 1.65 bar.

When it flows through the second fixed catalyst bed, approximately 18% of the molecular hydrogen present in the reaction gas mixture is initially combusted with the molecular oxygen metered in the form of air to give water. This heats the reaction gas mixture to 618° C. In the further course of the flow through the second fixed catalyst bed, there is heterogeneously catalyzed dehydrogenation of the propane. The bed height of the second fixed catalyst bed is such that the reaction gas mixture leaves the second fixed catalyst bed at a temperature of 546° C. and a pressure of 1.55 bar with the following contents in an amount of 124 387 m$^3$ (STP)/h:
   12.0% by volume of propane,
   12.6% by volume of propene,
   6.6% by volume of H$_2$,
   7.5% by volume of H$_2$O and
   0% by volume of O$_2$.

To this product gas mixture A* are subsequently fed 89 715 m$^3$ (STP)/h of overall residual gas from separation zone B at a temperature of 627° C. The overall residual gas has the following contents:
   14.6% by volume of propane,
   0% by volume of propene,
   0% by volume of H$_2$,
   1.9% by volume of H$_2$O and
   3.0% by volume of O$_2$.

The overall residual gas is fed by the principle of a jet pump operated with this overall residual gas as a driving jet, and the conveying direction of the driving jet decompressed through a driving nozzle via a mixing zone and a diffuser points into the second section of reaction zone A, and the sucking direction of the sucking nozzle points in the direction of the mixture of molecular hydrogen and product gas mixture A*.

The resulting reaction gas mixture A* flows in an amount of 214 102 m$^3$ (STP)/h and at a temperature of 580° C. and a pressure of 1.85 bar into a second shaft furnace reactor which forms the second section of reaction zone A, is likewise configured adiabatically and comprises a fixed catalyst bed which is likewise charged with the dehydrogenation catalyst according to Comparative Example 1. It has the following contents:
   13.1% by volume of propane,
   7.3% by volume of propene,
   3.8% by volume of H$_2$,
   5.2% by volume of H$_2$O and
   1.3% by volume of O$_2$.

When it flows through this third fixed catalyst bed, the molecular oxygen present in reaction gas mixture A* is initially combusted substantially fully with the molecular hydrogen present therein to give water, which heats the reaction gas mixture to 692° C.

The bed height of the third fixed catalyst bed is such that there is still a small degree of heterogeneously catalyzed propane dehydrogenation in the reaction gas mixture until it leaves the third fixed catalyst bed.

As a result, 213 021 m$^3$ (STP)/h of product gas mixture A leave the third fixed catalyst bed at a temperature of 677° C. and a pressure of 1.75 bar. It contains the following contents:

12.3% by volume of propane,
8.2% by volume of propene,
2.2% by volume of $H_2$,
7.7% by volume of $H_2O$ and
0% by volume of $O_2$.

Product gas mixture A is divided into two halves of identical composition.

Of this, one half is recycled into the first section of reaction zone A as a constituent of the starting reaction gas mixture therefor.

The other half is fed via an indirect heat exchanger W for gases to separation zone A. In the heat exchanger, the residual gas from separation zone B which is recycled into reaction zone A is heated to 627° C.

In separation zone B, the propane and propene present in the second half of product gas mixture A are removed absorptively therefrom as in Comparative Example 1 and subjected as in Comparative Example 1 to the two-stage heterogeneously catalyzed partial oxidation of propene to acrylic acid in reaction zone B.

From the resulting product gas mixture B, the acrylic acid is removed as in Comparative Example 1 in separation zone B, and the remaining overall residual gas is compressed (to approx. 4 bar) and fed as described via the heat exchanger W to the jet pump operated with the overall residual gas as a driving jet and combined with product gas mixture A*. The amount of acrylic acid removed in separation zone B amounts to 332 kmol/h. The amount of residual gas in the above-described gas mixtures consists substantially of molecular nitrogen and of small amounts of carbon oxides. The process described can be operated over a prolonged period substantially without reduction.

U.S. Provisional Patent Application No. 60/584,469 (filed on Jul. 1, 2004) and 60/662,804 (filed on Mar. 18, 2005) are incorporated into the present application by literature reference. With regard to the abovementioned teachings, numerous alterations and deviations from the present invention are possible. It can therefore be assumed that the invention, within the scope of the appended claims, may be performed differently to the way specifically described herein.

What is claimed is:

1. A process for preparing acrolein or acrylic acid or a mixture thereof from propane, by
   A) feeding to a first reaction zone A at least two gaseous, propane-containing feed streams, at least one of which comprises fresh propane, and, in reaction zone A, subjecting their propane fed in this way to a heterogeneously catalyzed dehydrogenation to obtain a product gas mixture A comprising propane and propylene,
   B) conducting product gas mixture A out of reaction zone A and, in a first separation zone A, removing at least a portion of the constituents, other than propane and propylene, present in product gas mixture A, and using remaining product gas mixture A' comprising propane and propylene
   C) in a second reaction zone B to charge at least one oxidation reactor and, in the at least one oxidation reactor, subjecting the propylene present in product gas mixture A' to a heterogeneously catalyzed gas phase partial oxidation with molecular oxygen to give a product gas mixture B comprising acrolein or acrylic acid or a mixture thereof as the target product and also excess molecular oxygen,
   D) conducting product gas mixture B out of reaction zone B and, in a second separation zone B, removing target product present in product gas mixture B, and, of the remaining residual gas comprising unconverted propane, molecular oxygen and any unconverted propylene, recycling at least a portion comprising unconverted propane, molecular oxygen and any unconverted propylene as one of the at least two propane-containing feed streams into reaction zone A, wherein this recycling into reaction zone A along the reaction path of the heterogeneously catalyzed dehydrogenation of propane in reaction zone A is effected such that, at the feed point, at least 5 mol % of the propane fed to reaction zone A via the other feed streams has already been converted under dehydrogenating conditions in reaction zone A.

2. The process according to claim 1, wherein at least half of the residual gas which remains in separation zone B and comprises unconverted propane, molecular oxygen and any unconverted propylene is recycled into reaction zone A.

3. The process according to claim 1, wherein the entire amount of the residual gas which remains in separation zone B and comprises unconverted propane, molecular oxygen and any unconverted propylene is recycled into reaction zone A.

4. The process according to claim 1, wherein residual gas which remains in separation zone B and comprises unconverted propane, molecular oxygen and any unconverted propylene is recycled into reaction zone A only at one point in reaction zone A.

5. The process according to claim 1, wherein residual gas which remains in separation zone B and comprises unconverted propane, molecular oxygen and any unconverted propylene is recycled into reaction zone A distributed over a plurality of feed points arranged in senes.

6. The process according to claim 1, wherein residual gas which remains in separation zone B and comprises unconverted propane, molecular oxygen and any unconverted propylene is recycled into reaction zone A such that, at the feed point, at least 20 mol % of the propane which is fed to reaction zone A via the other feed streams has been converted under dehydrogenating conditions in reaction zone A.

7. The process according to claim 1, wherein residual gas which remains in separation zone B and comprises unconverted propane, molecular oxygen and any unconverted propylene is recycled into reaction zone A such that, at the feed point, at least 30 mol % of the propane which is fed to reaction zone A via the other feed streams has been converted under dehydrogenating conditions in reaction zone A.

8. The process according to claim 1, wherein the molecular oxygen content of the residual gas which remains in separation zone B, comprises unconverted propane, molecular oxygen and any unconverted propylene and is recycled into reaction zone A is from 0.5 to 10% by volume.

9. The process according to claim 1, wherein the molecular oxygen content of the residual gas which remains in separation zone B, comprises unconverted propane, molecular oxygen and any unconverted propylene and is recycled into reaction zone A is from 2 to 5% by volume.

10. The process according to claim 1, wherein the ratio of the amount of propane which is fed to reaction zone A via recycled residual gas stemming from separation zone B to the total amount of propane which is fed to reaction zone A via other feed streams is from 0.1 to 10.

11. The process according to claim 1, wherein only residual gas stemming from separation zone B and crude propane as fresh propane are fed as propane-containing feed streams to reaction zone A.

12. The process according to claim 1, wherein the reaction gas mixture in reaction zone A, at the feed point for the residual gas stemming from separation zone B, based on the molar amount of propane contained therein, has a higher molar hydrogen content than the starting reaction gas mixture fed to reaction zone A.

13. The process according to claim 1, wherein the reaction gas mixture which forms in reaction zone A at the feed point for the residual gas, stemming from separation zone B, composed of this fed residual gas and the reaction gas mixture present at the feed point in reaction zone A upstream of this residual gas feed, based on the molar amount of propane contained therein, has a higher molar hydrogen content than the starting reaction gas mixture fed to reaction zone A.

14. The process according to claim 1, wherein the reaction temperatures in reaction zone A are from 300° to 800° C.

15. The process according to claim 1, wherein dehydrogenation catalysts are also used in reaction zone A which contain from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group, of the Periodic Table of the Elements, lanthanum and/or tin, with the proviso that the sum of the percentages by weight is 100% by weight.

16. The process according to claim 1, wherein the catalysts used in reaction zone A are catalyst extrudates and/or catalyst rings.

17. The process according to claim 1, wherein the reaction zone A used is a tray reactor.

18. The process according to claim 1, wherein the conversion of propane achieved in reaction zone A, based on the total amount of propane fed to reaction zone A and based on single pass through reaction zone A, is from 30 to 60 mol %.

19. The process according to claim 1, wherein the conversion of propane achieved in reaction zone A, based on the total amount of propane fed to reaction zone A and based on single pass through reaction zone A, is from 40 to 50 mol %.

20. The process according to claim 1, wherein the product gas mixture A formed in reaction zone A is divided into two portions of identical composition, one of the two portions is recycled into reaction zone A as one of the propane-containing feed streams and of the other portion is conducted out of reaction zone A into the first separation zone A.

21. The process according to claim 20, wherein the portion of product gas mixture A recycled into reaction zone A, based on the total amount of product gas mixture A formed in reaction zone A, is from 30 to 70% by volume.

22. The process according to claim 20, wherein the portion of product gas mixture A recycled into reaction zone A, based on the total amount of product gas mixture A formed in reaction zone A, is from 40 to 60% by volume.

23. The process according to claim 20, wherein the portion of product gas mixture A recycled into reaction zone A is recycled into reaction zone A as a constituent of the starting reaction gas mixture fed to reaction zone A.

24. The process according to claim 1, wherein reaction zone A is configured and operated with the proviso that it consists of a first and of a second section, by
  I. feeding to the first section of reaction zone A at least one feed stream comprising gaseous propane, which comprises fresh propane, and, in this first section of reaction zone A, subjecting the propane fed to it in such a way to a heterogeneously catalyzed dehydrogenation to obtain a product gas mixture A* comprising propane, propylene and molecular hydrogen and which has been obtained by converting under dehydrogenating conditions at least 5 mol % of the propane fed to the first section of reaction zone A in this first section of reaction zone A and which, based on the molar amount of propane contained therein, contains a larger molar amount of molecular hydrogen than the starting reaction gas mixture fed to the first section of reaction zone A;
  II. subsequently feeding residual gas, comprising molecular oxygen, unconverted propane and any unconverted propylene, from separation zone B to product gas mixture A* and feeding the resulting reaction gas mixture A* to the second section of reaction zone A, and
  III. in this second section of reaction zone A, with formation of product gas mixture A comprising propane and propylene, combusting molecular oxygen present in reaction gas mixture A* with molecular hydrogen present in reaction gas mixture A* under heterogeneous catalysis to give water and dehydrogenating propane present in reaction gas mixture A*, if appropriate under heterogeneous catalysis, to give propylene.

25. The process according to claim 24, wherein the first section of reaction zone A is configured adiabatically.

26. The process according to claim 24, wherein the second section of reaction zone A is configured adiabatically.

27. The process according to claim 24, wherein both the first and the second section of reaction zone A are configured adiabatically, with the proviso that
  the gross thermal character based on single pass of the starting reaction gas mixture fed to the first section of reaction zone A through the first section of reaction zone A is endothermic to autothermic, and
  the gross thermal character based on single pass of the reaction gas mixture A* fed to the second section of reaction zone A through the second section of reaction zone A is exothermic.

28. The process according to claim 24, wherein the first section of the reaction zone has tray structure.

29. The process according to claim 24, wherein product gas mixture A contains less than 5% by volume of molecular hydrogen.

30. The process according to claim 24, wherein the first and the second section of reaction zone A are accommodated in one reactor.

31. The process according to claim 24, wherein product gas mixture A is divided into two portions of identical composition and one of the two portions is recycled into the first section of reaction zone A.

32. The process according to claim 24, wherein the residual gas, comprising unconverted propane, molecular oxygen and any unconverted propylene, from separation zone B is fed to product gas mixture A* by the principle of a jet pump operated with this residual gas as the driving jet, and the conveying direction of the driving jet decompressed through a driving nozzle via a mixing zone and a diffuser points into the second section of reaction zone A, and the sucking action of the sucking nozzle points in the direction of the first section of reaction zone A, and the sucking nozzle-mixing zone-diffuser connection forms the sole connection between the two sections of reaction zone A.

33. The process according to claim 32, wherein the pressure of the driving jet is selected such that the pressure of the product gas mixture A which forms in the second section of reaction zone A is above the pressure of the product gas mixture A* which forms in the first section of reaction zone A.

34. The process according to claim 33, wherein product gas mixture A is divided into two portions of identical composition and one of the two portions is recycled into the first section of reaction zone A in a kind of natural circulation following the pressure gradient between product gas mixture A and product gas mixture A*.

35. The process according to claim 1, wherein the product gas mixture conducted into separation zone A is conducted into separation zone A via an indirect heat exchanger in order to heat the fresh propane and/or the residual gas from separation zone B in this indirect heat exchanger.

36. The process according to claim 1, wherein no external steam is fed to either of the two reaction zones A, B or either of the two separation zones A, B.

37. The process according to claim 1, wherein product gas mixture A is contacted in separation zone B with an organic solvent in which propane and propylene are absorbed.

38. The process according to claim 1, wherein reaction zone B is configured as a two-stage heterogeneously catalyzed gas phase partial oxidation of propylene to acrylic acid.

39. The process according to claim 1, wherein the target product removal in reaction zone B is effected by absorption of the target product in an absorbent or by fractional condensation of product gas mixture B.

40. The process according to claim 1, wherein the residual gas which remains in separation zone B and is recycled into reaction zone A has the following constituents with the following contents:

from 10 to 40% by volume of propane,
from 0 to 1% by volume of propene,
from >0 to 5% by volume of molecular oxygen,
from 1 to 10% by volume of steam and
from 0 to 0.5% by volume of molecular hydrogen.

41. The process according to claim 1, wherein the molar ratio of propylene present in the reaction gas mixture to molecular hydrogen present in the reaction gas mixture in reaction zone A does not at any point exceed the value of 10.

* * * * *